(12) United States Patent
McCray et al.

(10) Patent No.: US 7,297,786 B2
(45) Date of Patent: Nov. 20, 2007

(54) RNA INTERFERENCE IN RESPIRATORY EPITHEIAL CELLS

(75) Inventors: Paul B. McCray, Iowa City, IA (US); Beverly L. Davidson, North Liberty, IA (US); Anthony J. Fischer, Iowa City, IA (US); Hong P. Jia, Iowa City, IA (US); Maureen D. Donovan, Swisher, IA (US); Patrick L. Sinn, Iowa City, IA (US); Mark Aaron Behlke, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 11/179,848

(22) Filed: Jul. 11, 2005

(65) Prior Publication Data

US 2006/0084620 A1  Apr. 20, 2006

Related U.S. Application Data

(60) Provisional application No. 60/586,554, filed on Jul. 9, 2004, provisional application No. 60/622,758, filed on Oct. 28, 2004.

(51) Int. Cl.
  *C07H 21/04* (2006.01)
  *C12N 15/00* (2006.01)
  *C12N 5/00* (2006.01)
  *C12N 1/20* (2006.01)

(52) U.S. Cl. .............. 536/24.5; 435/320.1; 435/252.3; 435/325; 536/24.1; 424/484; 424/494

(58) Field of Classification Search .................... None
See application file for complete search history.

(56) References Cited

U.S. PATENT DOCUMENTS

| | | | |
|---|---|---|---|
| 5,350,674 A | 9/1994 | Boenisch et al. | |
| 5,585,362 A | 12/1996 | Wilson et al. | |
| 5,705,188 A | 1/1998 | Junichi et al. | |
| 5,808,041 A * | 9/1998 | Padhye et al. | 536/25.4 |
| 5,831,069 A | 11/1998 | Barik | |
| 6,153,431 A * | 11/2000 | Beretta et al. | 435/372.3 |
| 6,342,251 B1 | 1/2002 | Illum et al. | |
| 6,514,947 B2 * | 2/2003 | Rolland et al. | 514/44 |
| 6,593,130 B1 | 7/2003 | Sen et al. | |
| 6,610,667 B1 | 8/2003 | Dettmar et al. | |
| 6,632,423 B2 | 10/2003 | Jafari et al. | |
| 6,652,874 B2 | 11/2003 | Ragavan et al. | |
| 6,855,549 B1 | 2/2005 | McCray et al. | |
| 2002/0086356 A1 | 7/2002 | Tuschl et al. | |
| 2004/0091457 A1 | 5/2004 | John et al. | |
| 2004/0203145 A1 | 10/2004 | Zamore et al. | |
| 2004/0242518 A1 | 12/2004 | Chen et al. | |
| 2005/0008617 A1 | 1/2005 | Chen et al. | |
| 2005/0054598 A1 | 3/2005 | McSwiggen | |
| 2005/0244858 A1 | 11/2005 | Rossi et al. | |
| 2006/0089323 A1* | 4/2006 | Barik | 514/44 |
| 2006/0089324 A1 | 4/2006 | Barik | |
| 2006/0160759 A1 | 7/2006 | Chen et al. | |
| 2006/0287267 A1 | 12/2006 | Vaish et al. | |

FOREIGN PATENT DOCUMENTS

| | | |
|---|---|---|
| EP | 166 596 | 1/1986 |
| WO | WO 95/03357 | 2/1995 |
| WO | WO 97/30731 | 8/1997 |
| WO | WO 03/080807 | 10/2003 |
| WO | WO 03/099298 | 12/2003 |
| WO | WO 2004/011647 | 2/2004 |
| WO | WO 2004/013280 | 2/2004 |
| WO | WO 2005/056021 | 6/2005 |
| WO | WO 2006/062596 | 6/2006 |
| WO | WO 2006/110688 | 10/2006 |

OTHER PUBLICATIONS

Collins et al (Proc. Nat. Acad. Sci. USA (Jun. 1983) vol. 80, No. 11, pp. 3208-3212).*
Grosfeld et al (J. Virol. 69(9): 5677-5686, 1995).*
Altschul et al., JMB, 215, 403 (1990).
Amarzguioui et al., Biochem Biophys Res Commun., 316(4):1050 (2004).
Bitko et al., BMC Microbiology 1:34 (2001).
Bitko et al., Nat. Med. 11:50 (2005).
Bondensgaard et al., Chem Eur J, 6:2687 (2000).
Bosher et al., Nat Cell Biol 2:E31 (2000).
Braasch et al., Chem and Biol. 8:1 (2001).
Cao et al., Cell Res. 15:111 (2005).
Carmichael et al., Nature, 418, 379 (2002).
Corpet et al., Nucl. Acids Res., 16, 10881 (1988).
Crinelli et al., Nucl. Acids Res. 30:2435 (2002).
Dean et al., Gene Ther., 10:1608 (2003).
Deng et al., J. Polymer Sci. Part C Polymer letters, 24, 411 (1988).
Donzé et al., Nucleic Acid Res. 30:e46, 1 (2002).
Elbashir et al., Genes Dev. 15:188 (2001).
Elbashir et al., Nature 411:494 (2001).
Elmén et al., Nuc. Acids Res. 33:439 (2005).
Fire et al., Trends Genet. 15:358 (1999).
Fire et al., Nature 391:806 (1998).
Ge et al., Proc. Natl. Acad. Sci. USA, 100(5):2718 (2003).
Ge et al., Proc. Natl. Acad. Sci. USA, 101(23):8676 (2004).

(Continued)

*Primary Examiner*—Richard Schnizer
(74) *Attorney, Agent, or Firm*—Viksnins Harris & Padys PLLP

(57) ABSTRACT

The present invention is directed to small interfering RNA molecules targeted against a gene of interest in respiratory epithelial cells, and methods of using these RNA molecules.

57 Claims, 36 Drawing Sheets
(9 of 36 Drawing Sheet(s) Filed in Color)

OTHER PUBLICATIONS

Gitlin et al., J. Virol. 77:7159 (2003).
Gönczy et al., Nature 408:331 (2000).
Gref et al., Science, 263, 1600 (1994).
Grishok et al., Cell 106:23 (2001).
Hannon, Nature 418:244 (2002).
Higgins et al., Gene, 73, 237 (1988).
Higgins et al., CABIOS, 5, 151 (1989).
Holen et al., Nucl. Acids Res 30:1757 (2002).
Huang et al., CABIOS, 8, 155 (1992).
Ji et al., FEBS Lett 552:247 (2003).
Karlin et al., Proc. Natl. Acad. Sci. USA, 87, 2264 (1990).
Karlin et al., Proc. Natl. Acad. Sci. USA 90, 5873 (1993).
Kennerdell et al., Cell 95:1017 (1998).
Khvorova et al., Cell 115:209 (2003).
Kim et al., Nature Biotech 23:222 (2005).
Knight et al., Science 293:2269 (2001).
Kurreck et al., Nucl. Acids Res. 30:1911 (2002).
Lagos-Quintana et al., Science 294:853 (2001).
Lau et al. Science 294:858 (2001).
Lee et al., Science 294:862 (2001).
Lee et al., Nat. Biotechnol. 19:500 (2002).
Lipardi et al., Cell 107:297 (2001).
McCaffrey et al., Nat. Biotechnol. 21:639 (2003).
Meinkoth et al., Anal. Biochem., 138, 267 (1984).
Miller, et al., Mol. Cell. Biol., 10, 4239 (1990).
Myers et al., CABIOS, 4, 11 (1988).
Needleman et al., JMB, 48, 443 (1970).
Pearson et al., Meth. Mol. Biol., 24, 307 (1994).
Pearson et al., Proc. Natl. Acad. Sci. USA, 85, 2444 (1988).
Platz et al., Oligonucleotides 15:132 (2005).
Reynolds et al., Nat Biotechnol., 22(3):326 (2004).
Rose et al., Nucleic Acids Res. 33(13):4140 (2005).
Scherer et al., Nat. Biotechnology 21:1457 (2003).
Schwarz et al., Cell 115:199 (2003).
Seiler et al., Am J. Respir. Cell Mol. Biol. 27:133 (2002).
Shah et al., AAPS PharmSci 5(4), R6144 (2003).
Sinn et al. Am J Respir Cell Mol Biol. 32:404 (2005).
Smith et al., Adv. Appl. Math., 2, 482 (1981).
Sontheimer, Nature Reviews, 6, 127 (2005).
Tompkins et al., Proc. Natl. Acad. Sci. USA, 101(23):8682 (2004).
Ui-Tei et al., Nucl. Acids Res 32:936 (2004).
Wahlestedt et al., PNAS 97:5633-5638 (2000).
Wang et al., J Clin Invest. 104(11):R55 (1999).
Waterhouse et al., Nature 411:834 (2001).
Xia et al., Nat. Biotechnol., 19:640 (2001).
Xia et al., Nat Biotechnol 20:1006 (2002).
Zabner et al., Am J Physiol Lung Cell Mol Physiol. 284(5):L844 (2003).
Zamore et al., Cell 101:25 (2000).
Zhang et al., Nature Medicine 11(1):56 (2004).
Zhu et al., J. Polym. Sci. Polm. Chem., 27:2151 (1989).
Partial International Search for International Application No. PCT/US2005/024626 (2006).
Braasch et al., "RNA interference in mammalian cells by chemically-modified RNA", *Biochemistry*, 42(26), 7967-7975 (2003).

\* cited by examiner

Fig. 3A | Fig. 3B | Fig. 3C siRNA oligonucleotide sequences targeting the SARS-CoV

5' UTR

| Position | Sense | T7 | Antisense | T7 | SEQ ID |
|---|---|---|---|---|---|
| 27 | aaccaccaacctcgatctc | TATAGTGAGTCGTATTA SEQ ID No:9 | aagagatcgaggttggtgc | TATAGTGAGTCGTATTA | SEQ ID No:10 |
| 48 | ttgtagatctgttcctaaac | TATAGTGAGTCGTATTA | tcgtttagagaacagatctac | TATAGTGAGTCGTATTA | SEQ ID No:11 |
| 83 | gttagctgtctcggctgc | TATAGTGAGTCGTATTA | atgcagccgagcgacagctac | TATAGTGAGTCGTATTA | SEQ ID No:12 |
| 96 | tcggctgcatgcctagtgca | TATAGTGAGTCGTATTA | aggtgcactagcatgcagcc | TATAGTGAGTCGTATTA | SEQ ID No:13 |
| 111 | gtgcactacgcagtataaac | TATAGTGAGTCGTATTA | ttgtttatactgcgtaggtgc | TATAGTGAGTCGTATTA | SEQ ID No:14 |
| 152 | ttgacaagaacgagtaactc | TATAGTGAGTCGTATTA | acgagttactcgttttcttgtc | TATAGTGAGTCGTATTA | SEQ ID No:15 |
| 201 | tcgtccgtgttcgtcagtgatc | TATAGTGAGTCGTATTA | atgatcgactgcaacacggac | TATAGTGAGTCGTATTA | SEQ ID No:16 |
| 233 | taggttcgtccggtgtgac | TATAGTGAGTCGTATTA | cggtcacaccccggacgaaacc | TATAGTGAGTCGTATTA | SEQ ID No:17 |

Leader

| Position | Sense | T7 | Antisense | T7 | SEQ ID |
|---|---|---|---|---|---|
| 32 | tcggctgcatcctagtgcac | TATAGTGAGTCGTATTA | aggtgcactaggcatgcagcc | TATAGTGAGTCGTATTA | SEQ ID No:28 |
| 121 | cagactgcttacgtttcgtc | TATAGTGAGTCGTATTA | cggacgaaacctaagcagtc | TATAGTGAGTCGTATTA | SEQ ID No:29 |
| 189 | ccgaaggtaagacgtagagc | TATAGTGAGTCGTATTA | aggctctccatcttaccttc | TATAGTGAGTCGTATTA | SEQ ID No:30 |
| 265 | aggttagagacgtgctagtgc | TATAGTGAGTCGTATTA | acgcactagcacgtctctaac | TATAGTGAGTCGTATTA | SEQ ID No:31 |
| 318 | tcggaggcactgaacactc | TATAGTGAGTCGTATTA | ttgaggtgttcacgtgcctc | TATAGTGAGTCGTATTA | SEQ ID No:32 |
| 381 | ctgcccagctgacacagccc | TATAGTGAGTCGTATTA | taggctgttcaagctgggc | TATAGTGAGTCGTATTA | SEQ ID No:33 |
| 459 | gagctgttcagaaatggac | TATAGTGAGTCGTATTA | ccgtccattttctgcaaccagc | TATAGTGAGTCGTATTA | SEQ ID No:34 |
| 547 | ttgcataccccaatgttcttc | TATAGTGAGTCGTATTA | aagaagaacattgcggtatgc | TATAGTGAGTCGTATTA | SEQ ID No:35 |
| 621 | aagcttatgacttaggtgac | TATAGTGAGTCGTATTA | tcgtcacttaagtcataagac | TATAGTGAGTCGTATTA | SEQ ID No:36 |
| 690 | aagcatgcagtggtgcactc | TATAGTGAGTCGTATTA | cggagtgcaccactgcatgc | TATAGTGAGTCGTATTA | SEQ ID No:37 |

Polymerase

| Position | Sense | T7 | Antisense | T7 | SEQ ID |
|---|---|---|---|---|---|
| 41 | aagtgcagcccgtcttacacc | TATAGTGAGTCGTATTA | acggtgtaagacgggctgcac | TATAGTGAGTCGTATTA | SEQ ID No:60 |
| 168 | caggagaggatgaggaagc | TATAGTGAGTCGTATTA | ttgccttcctcatcctcctcc | TATAGTGAGTCGTATTA | SEQ ID No:61 |
| 313 | gagtagatggtgacatggtac | TATAGTGAGTCGTATTA | tggtaccatgtcaccatctac | TATAGTGAGTCGTATTA | SEQ ID No:62 |
| 415 | gtatacattaaagagaatac | TATAGTGAGTCGTATTA | gagtatttctttaatgtatc | TATAGTGAGTCGTATTA | SEQ ID No:63 |
| 533 | aggtgagcgtgtacgccaatc | TATAGTGAGTCGTATTA | atgattggcgtacacgctcac | TATAGTGAGTCGTATTA | SEQ ID No:64 |
| 645 | tggtacgattcggtgattc | TATAGTGAGTCGTATTA | acgaaatcaccgaaatcgtac | TATAGTGAGTCGTATTA | SEQ ID No:65 |
| 744 | agggcattggctgctgagtcc | TATAGTGAGTCGTATTA | tgggactcagcagccaatgcc | TATAGTGAGTCGTATTA | SEQ ID No:66 |
| 867 | tgggaccagacataccatccc | TATAGTGAGTCGTATTA | tggatgtgtatgtctggtcc | TATAGTGAGTCGTATTA | SEQ ID No:67 |
| 1007 | ggtgttccttttgttgttc | TATAGTGAGTCGTATTA | ttgaacaacaaaaggaacac | TATAGTGAGTCGTATTA | SEQ ID No:68 |

Fig. 3A siRNA oligonucleotide sequences targeting the SARS-CoV

| S Protein Position | Sense | | | | T7 |
|---|---|---|---|---|---|
| 39 | tagtgaccttgaccggtgcac | SEQ ID No:47 | | | TATAGTGAGTCGTATTA |
| 200 | cagggtttcatactattaatc | SEQ ID No:48 | | | TATAGTGAGTCGTATTA |
| 396 | gtgtacaacccttcttttgc | SEQ ID No:49 | | | TATAGTGAGTCGTATTA |
| 527 | caggtaattaccaagagcaac | SEQ ID No:50 | | | TATAGTGAGTCGTATTA |
| 661 | aagttgccctcttgtattac | SEQ ID No:51 | | | TATAGTGAGTCGTATTA |
| 824 | ctgttgatttgttctcaaaatc | SEQ ID No:52 | | | TATAGTGAGTCGTATTA |
| 1017 | atgggagagacattggagagc | SEQ ID No:53 | | | TATAGTGAGTCGTATTA |
| 1131 | ttgctctccaatgtctatgc | SEQ ID No:54 | | | TATAGTGAGTCGTATTA |
| 1241 | atgattcatgggtgtgtc | SEQ ID No:55 | | | TATAGTGAGTCGTATTA |
| 1356 | gagagacatactaaatgcc | SEQ ID No:56 | | | TATAGTGAGTCGTATTA |
| 1487 | ttgtagtactttctttgaac | SEQ ID No:57 | | | TATAGTGAGTCGTATTA |
| 1656 | ccgtatgtttctgattcac | SEQ ID No:58 | | | TATAGTGAGTCGTATTA |
| 1811 | ctgttcttctcacagcaattc | SEQ ID No:59 | | | TATAGTGAGTCGTATTA |

(S Protein Position | Sense sequence | SEQ ID)

| S Protein Position | Sense | | | | T7 |
|---|---|---|---|---|---|
| 1120 | atgctgctgatccagctatgc | SEQ ID No:47 | | | TATAGTGAGTCGTATTA |
| 1288 | aggaggaagttctgttgaac | SEQ ID No:48 | | | TATAGTGAGTCGTATTA |
| 1453 | gtggctgtattaatgccaacc | SEQ ID No:49 | | | TATAGTGAGTCGTATTA |
| 1600 | atgtcatcccactataactc | SEQ ID No:50 | | | TATAGTGAGTCGTATTA |
| 1790 | ctgcataatatgttaaaaac | SEQ ID No:51 | | | TATAGTGAGTCGTATTA |
| 1897 | tggcctctcttgttcttgctc | SEQ ID No:52 | | | TATAGTGAGTCGTATTA |
| 1992 | gagatggtcatgtggcggc | SEQ ID No:53 | | | TATAGTGAGTCGTATTA |
| 2146 | ctgacaagtatgtccgcaatc | SEQ ID No:54 | | | TATAGTGAGTCGTATTA |
| 2265 | atgatttctgatgatgcc | SEQ ID No:55 | | | TATAGTGAGTCGTATTA |
| 2407 | ctgaccttactaagaggacctc | SEQ ID No:56 | | | TATAGTGAGTCGTATTA |
| 2539 | ttgtcaaaacagatgtacac | SEQ ID No:57 | | | TATAGTGAGTCGTATTA |
| 2698 | tggacatgtattccgtaatgc | SEQ ID No:58 | | | TATAGTGAGTCGTATTA |
| 2769 | atgtacacaccacatacagtc | SEQ ID No:59 | | | TATAGTGAGTCGTATTA |

| | Antisense | | | | T7 |
|---|---|---|---|---|---|
| | tggtgcaccgtcaaggtcac | SEQ ID No:106 | | | TATAGTGAGTCGTATTA |
| | atgattaatagtgaaaccc | SEQ ID No:107 | | | TATAGTGAGTCGTATTA |
| | cagcaaaagaaagggttgtcac | SEQ ID No:108 | | | TATAGTGAGTCGTATTA |
| | tcgtagtgtttaaaattacc | SEQ ID No:109 | | | TATAGTGAGTCGTATTA |
| | atgttaataccaagagcaac | SEQ ID No:110 | | | TATAGTGAGTCGTATTA |
| | tggatttgagaacaatcaac | SEQ ID No:111 | | | TATAGTGAGTCGTATTA |
| | tagaaattttttctctccc | SEQ ID No:112 | | | TATAGTGAGTCGTATTA |
| | ctgcatagacattggagagc | SEQ ID No:113 | | | TATAGTGAGTCGTATTA |
| | aaggcaccaaccctagaaatc | SEQ ID No:114 | | | TATAGTGAGTCGTATTA |
| | aagttcaaaagaaagtactac | SEQ ID No:115 | | | TATAGTGAGTCGTATTA |
| | cagtgaaatcagaaacatcac | SEQ ID No:116 | | | TATAGTGAGTCGTATTA |
| | atgaattgctgtagaaacatc | SEQ ID No:117 | | | TATAGTGAGTCGTATTA |
| | atgtaactagcacaaatgcc | SEQ ID No:118 | | | TATAGTGAGTCGTATTA |
| | gagaagcaaattagcacattc | SEQ ID No:119 | | | TATAGTGAGTCGTATTA |
| | aagccagcatcagcagtgtc | SEQ ID No:120 | | | TATAGTGAGTCGTATTA |
| | caccagcaccaaatgcc | SEQ ID No:121 | | | TATAGTGAGTCGTATTA |
| | cagcgccagcaccaaatgtcc | SEQ ID No:122 | | | TATAGTGAGTCGTATTA |
| | tggttaacaacgtcttgcagc | SEQ ID No:123 | | | TATAGTGAGTCGTATTA |
| | ctgtcaatttgtacctccgcc | SEQ ID No:124 | | | TATAGTGAGTCGTATTA |

Fig. 3B siRNA oligonucleotide sequences targeting the SARS-CoV

| Position | Sense | | | T7 |
|---|---|---|---|---|
| 3094 | atgtccttccacaagcagcc | SEQ ID No:101 | ggggctgcttgtggaaggac SEQ ID No:125 | TATAGTGAGTCGTATTA |
| 3194 | atgaaggcaaagcatacttcc | SEQ ID No:102 | aggaagtatgctttgccttc SEQ ID No:126 | TATAGTGAGTCGTATTA |
| 3359 | atgatccctgcaacctgagc | SEQ ID No:103 | aagctcaggttgcagaggatc SEQ ID No:127 | TATAGTGAGTCGTATTA |
| 3586 | tggtatgtttggctcggcttc | SEQ ID No:104 | atgaagccgagccaaacatac SEQ ID No:128 | TATAGTGAGTCGTATTA |
| 3744 | gggtgtcaaattacattacac | SEQ ID No:105 | atgtgtaatgtaatttgacac SEQ ID No:129 | TATAGTGAGTCGTATTA |

Nucleocapsid protein

| Position | Sense | | Antisense | T7 |
|---|---|---|---|---|
| 11 | atggacccaatcaaaccaac | SEQ ID No:130 | acgttggtttgattgggtcc SEQ ID No:142 | TATAGTGAGTCGTATTA |
| 120 | gcgccgaccgtcaagtttacc | SEQ ID No:131 | tgggtaaacttgacctgcgc SEQ ID No:143 | TATAGTGAGTCGTATTA |
| 245 | atgaccaaattggctactacc | SEQ ID No:132 | tcggtagccaatttggtc SEQ ID No:144 | TATAGTGAGTCGTATTA |
| 342 | aggaactggccagaagcttc | SEQ ID No:133 | gtgaagcttctgggccagttc SEQ ID No:145 | TATAGTGAGTCGTATTA |
| 464 | atgctgccacgtgctacaac | SEQ ID No:134 | aagttgtagcacgtggcagc SEQ ID No:146 | TATAGTGAGTCGTATTA |
| 576 | cgtaattcaagaaattcaac | SEQ ID No:135 | gagttgaatttcttgaattac SEQ ID No:147 | TATAGTGAGTCGTATTA |
| 701 | aagttttggtaaaggccaac | SEQ ID No:136 | tgttggcctttaccagaaac SEQ ID No:148 | TATAGTGAGTCGTATTA |
| 818 | aagcattgggagtcacacttc | SEQ ID No:137 | tgaccacgtctcccaaatgc SEQ ID No:149 | TATAGTGAGTCGTATTA |
| 963 | tggcatgaagctcagccttgc | SEQ ID No:138 | cgcaaggctgacttccatgc SEQ ID No:150 | TATAGTGAGTCGTATTA |
| 1130 | ctgatgattctccagacacc | SEQ ID No:139 | cgcaaagctgagcttcatc SEQ ID No:151 | TATAGTGAGTCGTATTA |
| 1202 | tggatgattctctgcttg | SEQ ID No:140 | aagttgtctgagaatcatc SEQ ID No:152 | TATAGTGAGTCGTATTA |
| 1241 | gagcttctgctgattcaactc | SEQ ID No:141 | ctgagttgaatcagcagaagc SEQ ID No:153 | TATAGTGAGTCGTATTA |

3' UTR

| Position | Sense | | Antisense | T7 |
|---|---|---|---|---|
| 1 | atggacccaatcaaaccaac | SEQ ID No:154 | acgttggtttgattgggtcc SEQ ID No:160 | TATAGTGAGTCGTATTA |
| 32 | ccgcattacattggtggacc | SEQ ID No:155 | tgggtccaccaaatgtaatgc SEQ ID No:161 | TATAGTGAGTCGTATTA |
| 82 | gaggacgcaatgggcaaggc | SEQ ID No:156 | tggccttgcccattgcgtcc SEQ ID No:162 | TATAGTGAGTCGTATTA |
| 122 | agtttaccaatatactc | SEQ ID No:157 | accagtatattgggtaaac SEQ ID No:163 | TATAGTGAGTCGTATTA |
| 201 | cagggcgttccaatcaacacc | SEQ ID No:158 | ttgtgttgattggaacgccc SEQ ID No:164 | TATAGTGAGTCGTATTA |
| 235 | atgacccaattggctactacc | SEQ ID No:159 | tcggtagtagccaattggtc SEQ ID No:165 | TATAGTGAGTCGTATTA |

Fig. 3C

Fig. 4 Sequence of shRNAs targeting the RSV A2 strain

| L Gene | Termination | siRNA sense | Loop | siRNA antisense | 23 nt mU6 |
|---|---|---|---|---|---|
| 8 | ctcgagaaaaa (SEQ ID NO:166) | AAGTTACATATTCAATGGTCC (SEQ ID NO:167) | tgacaggaag (SEQ ID NO:174) | GGACCATTGAATATGTAACTT (SEQ ID NO:175) | caaaacaaggcttttctccaagg (SEQ ID NO:182) |
| 72 | ctcgagaaaaa | AATGCAACATCCTCCATCATG (SEQ ID NO:168) | tgacaggaag | CATGATGGAGATGTTGCATT (SEQ ID NO:176) | caaaacaaggcttttctccaagg |
| 236 | ctcgagaaaaa | AACTGCATGGTGTACAATCTC (SEQ ID NO:169) | tgacaggaag | GAGATTGTACACCATGCAGTT (SEQ ID NO:177) | caaaacaaggcttttctccaagg |
| 276 | ctcgagaaaaa | AACGGTGTATATTACCCAGCT (SEQ ID NO:170) | tgacaggaag | AGCTGGGTAATATACACCGTT (SEQ ID NO:178) | caaaacaaggcttttctccaagg |
| 352 | ctcgagaaaaa | AACAGATATTGATAGAGCCAC (SEQ ID NO:171) | tgacaggaag | GTGGCTCTATCAATATCTGTT (SEQ ID NO:179) | caaaacaaggcttttctccaagg |
| 405 | ctcgagaaaaa | AATTCCCTGCATCAATACCAG (SEQ ID NO:172) | tgacaggaag | CTGGTATTGATGCAGGGAATT (SEQ ID NO:180) | caaaacaaggcttttctccaagg |
| 614 | ctcgagaaaaa | AAAGAGTGTTGTTAGTGGAGA (SEQ ID NO:173) | tgacaggaag | TCTCCACTAACAACACTCTTT (SEQ ID NO:181) | caaaacaaggcttttctccaagg |

| N Gene | Termination | siRNA sense | Loop | siRNA antisense | 23 nt mU6 |
|---|---|---|---|---|---|
| 8 | ctcgagaaaaa | AACGGAGCACAGGATAGTA (SEQ ID NO:183) | tgacaggaag | TACTATCTCCTGTGCTCCGTT (SEQ ID NO:190) | caaaacaaggcttttctccaagg |
| 21 | ctcgagaaaaa | AAATACTCAGAGATGCGGGAT (SEQ ID NO:184) | tgacaggaag | ATCCCGCATCTCTGAGTATTT (SEQ ID NO:191) | caaaacaaggcttttctccaagg |
| 50 | ctcgagaaaaa | AATACAGGCATGACTCTCCTG (SEQ ID NO:185) | tgacaggaag | CAGGAGAGTCATGCCTGTATT (SEQ ID NO:192) | caaaacaaggcttttctccaagg |
| 63 | ctcgagaaaaa | AAGGACATAGCCAACAGCTTC (SEQ ID NO:186) | tgacaggaag | GAAGCTGTTGGCTATGTCCTT (SEQ ID NO:193) | caaaacaaggcttttctccaagg |
| 68 | ctcgagaaaaa | AATCTTCTACCAGAGGTGGCA (SEQ ID NO:187) | tgacaggaag | TGCCACCTCTGGTAGAAGATT (SEQ ID NO:194) | caaaacaaggcttttctccaagg |
| 88 | ctcgagaaaaa | AATTTCCTCACTTCTCCAGTG (SEQ ID NO:188) | tgacaggaag | CACTGGAGAAGTGAGGAAATT (SEQ ID NO:195) | caaaacaaggcttttctccaagg |
| 90 | ctcgagaaaaa | AATGGGAGAGTACAGAGGTAC (SEQ ID NO:189) | tgacaggaag | GTACCTCTGTACTCTCCCATT (SEQ ID NO:196) | caaaacaaggcttttctccaagg |

| | Termination | siRNA sense | Loop | siRNA antisense | 23 nt mU6 |
|---|---|---|---|---|---|
| P-Gene | ctcgagaaaaa | AACGATAATATAACACAAGA (SEQ ID NO:197) | tgacaggaag | TCTTGCTGTTATATTATCGTT (SEQ ID NO:198) | caaaacaaggcttttctccaagg | siRNA oligos designed to the HCoV-229E gene sequences

3' UTR

| Position | Sense | T7 | Antisense | T7 |
|---|---|---|---|---|
| 26 | aggctttagttggaattttgc SEQ ID No:199 | TATAGTGAGTCGTATTA SEQ ID No:203 | aagcaaaattccaactaaagc | TATAGTGAGTCGTATTA |
| 90 | gagatttggcgccttggtgcc SEQ ID No:200 | TATAGTGAGTCGTATTA SEQ ID No:204 | acggcaccaaggcgccaaatc | TATAGTGAGTCGTATTA |
| 192 | tggcttgacaaggatctagtc SEQ ID No:201 | TATAGTGAGTCGTATTA SEQ ID No:205 | aagactagatccttgtcaagc | TATAGTGAGTCGTATTA |
| 347 | tggaagagccagtcatttgtc SEQ ID No:202 | TATAGTGAGTCGTATTA SEQ ID No:206 | aagacaaatgactggctcttc | TATAGTGAGTCGTATTA |

Leader

| Position | Sense | T7 | Antisense | T7 |
|---|---|---|---|---|
| 2 | tggcctgcaaccgtgtgacac SEQ ID No:207 | TATAGTGAGTCGTATTA SEQ ID No:211 | aagtgtcacacggttgcaggc | TATAGTGAGTCGTATTA |
| 60 | ctgttctactattgcgcaagc SEQ ID No:208 | TATAGTGAGTCGTATTA SEQ ID No:212 | cggcttgcgcaatagtagaac | TATAGTGAGTCGTATTA |
| 189 | gggtctgcatggcaatcagac SEQ ID No:209 | TATAGTGAGTCGTATTA SEQ ID No:213 | acgtctgattgccatgcagac | TATAGTGAGTCGTATTA |
| 295 | gaggaatttgatgttgtcttc SEQ ID No:210 | TATAGTGAGTCGTATTA SEQ ID No:214 | ccgaagacaacatcaaattcc | TATAGTGAGTCGTATTA |

Polymerase

| Position | Sense | T7 | Antisense | T7 |
|---|---|---|---|---|
| 27 | tagaaaagttgctttttagac SEQ ID No:215 | TATAGTGAGTCGTATTA SEQ ID No:223 | aagtctaaaaagcaacttttc | TATAGTGAGTCGTATTA |
| 150 | tggaagcaagtgctgtgtgtc SEQ ID No:216 | TATAGTGAGTCGTATTA SEQ ID No:224 | aggacacacagcacttgcttc | TATAGTGAGTCGTATTA |
| 760 | ttggcttactaagcgtaagcc SEQ ID No:217 | TATAGTGAGTCGTATTA SEQ ID No:225 | agggcttacgcttagtaagcc | TATAGTGAGTCGTATTA |
| 3498 | ttgatggtgactatgctatgc SEQ ID No:218 | TATAGTGAGTCGTATTA SEQ ID No:226 | ctgcatagcatagtcaccatc | TATAGTGAGTCGTATTA |
| 6441 | ttggttaccaagagttaagtc SEQ ID No:219 | TATAGTGAGTCGTATTA SEQ ID No:227 | ttgacttaactcttggtaacc | TATAGTGAGTCGTATTA |
| 10230 | ttgttgctttgtcactctgtc SEQ ID No:220 | TATAGTGAGTCGTATTA SEQ ID No:228 | aagacagagtgacaaagcaac | TATAGTGAGTCGTATTA |
| 12851 | tggatttgtgcttcgctctgc SEQ ID No:221 | TATAGTGAGTCGTATTA SEQ ID No:229 | acgcagagcgaagcacaaatc | TATAGTGAGTCGTATTA |
| 19861 | gtgttacacttgggtgctggc SEQ ID No:222 | TATAGTGAGTCGTATTA SEQ ID No:230 | gagccagcacccaagtgtaac | TATAGTGAGTCGTATTA |

Nucleocapsid protein

| Position | Sense | T7 | Antisense | T7 |
|---|---|---|---|---|
| 13 | tagaaaagttgctttttagac SEQ ID No:231 | TATAGTGAGTCGTATTA SEQ ID No:236 | aagtctaaaaagcaacttttc | TATAGTGAGTCGTATTA |
| 80 | atgggctgatgcatctgaacc SEQ ID No:232 | TATAGTGAGTCGTATTA SEQ ID No:237 | gtggttcagatgcatcagccc | TATAGTGAGTCGTATTA |
| 580 | gtgacagaaaccataacagtc SEQ ID No:233 | TATAGTGAGTCGTATTA SEQ ID No:238 | ctgactgttatggtttctgtc | TATAGTGAGTCGTATTA |
| 1042 | ctgtgcccaaagaccatccac SEQ ID No:234 | TATAGTGAGTCGTATTA SEQ ID No:239 | gtgtggatggtctttgggcac | TATAGTGAGTCGTATTA |
| 1492 | ttgctactatgttactgaacc SEQ ID No:235 | TATAGTGAGTCGTATTA SEQ ID No:240 | taggttcagtaacatagtagc | TATAGTGAGTCGTATTA |

5' UTR

| Position | Sense | T7 | Antisense | T7 |
|---|---|---|---|---|
| 27 | tagaaaagttgctttttagac SEQ ID No:241 | TATAGTGAGTCGTATTA SEQ ID No:244 | aagtctaaaaagcaacttttc | TATAGTGAGTCGTATTA |
| 111 | tcgtagtgtaattgaaatttc SEQ ID No:242 | TATAGTGAGTCGTATTA SEQ ID No:245 | atgaaatttcaattacactac | TATAGTGAGTCGTATTA |
| 199 | gagattccattctacaaacgc SEQ ID No:243 | TATAGTGAGTCGTATTA SEQ ID No:246 | aggcgtttgtagaatggaatc | TATAGTGAGTCGTATTA |

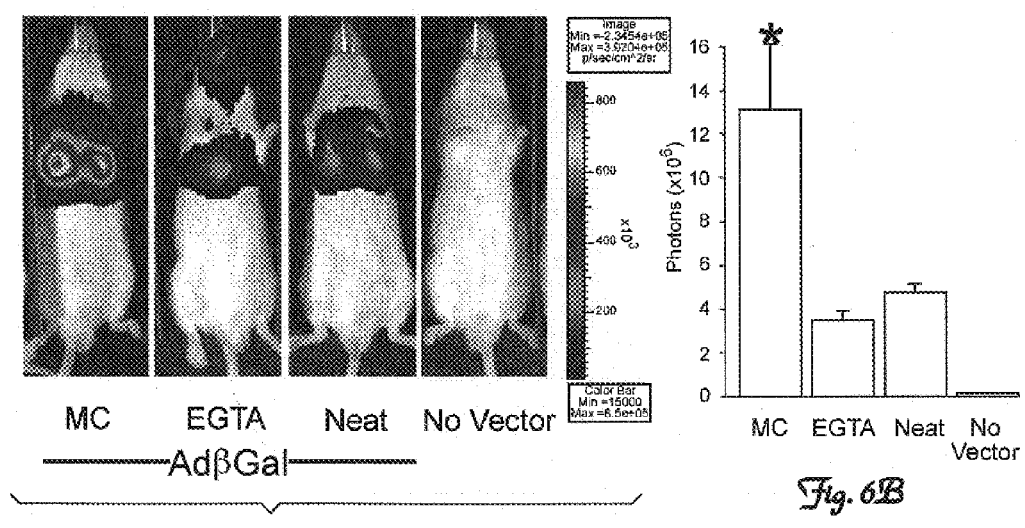

In vivo delivery of Cy3 labeled siRNA complexed with viscoelastic gel to murine airways 1% Methylcellulose / 600uM cy3-labelled oligo

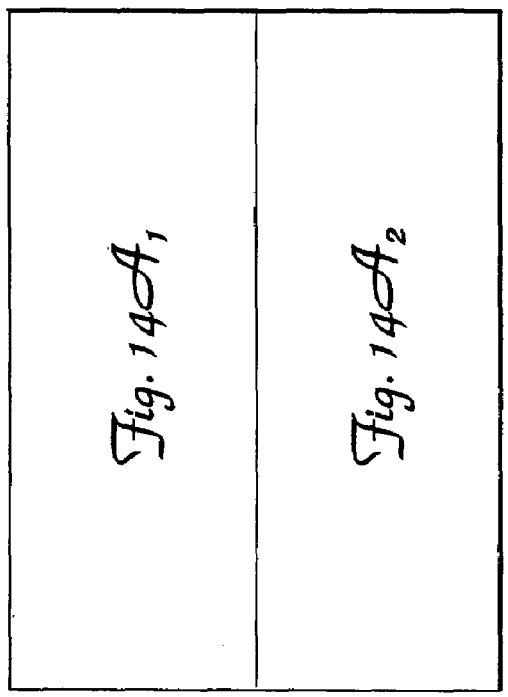

IL-8 NM_000584

LOCUS       NM_000584               1666 bp    mRNA    linear   PRI 26-OCT-2004
DEFINITION  Homo sapiens interleukin 8 (IL8), mRNA.
ACCESSION   NM_000584
VERSION     NM_000584.2  GI:28610153
SOURCE      Homo sapiens (human)

ctccataaggcacaaactttcagagacgcagagcacacaagcttctaggacaagagccaggaagaaacca
ccggaaggaaccatctcactgtgtgtaaacatgacttccaagctggccgtggctctcttggcagccttcctgatttc
tgcagctctgtgaaggtgcagttttgccaaggagtgctaaagaacttagatgtcagtgcataagacatctcca
accttccaccccaaattatcaaagaactgagagtgattgagagtgaccacactgcgccaacacagaaattatt
gtaaagctttctgatgaagagagctctgtctgacccaaggaaaactggtgcagagggtgtgtgagaagttttt
gaagagggctgagaattcataaaaaattcattctctgtggtatccaagaatcagtgaagatgccagtgaagttca
agcaaatctacttcaacacttcatgtatttgtgtggttttcattgtaccatgaaatatccagaacatacttatggtaaagta
aatttgaattcagtaaacaatgaatagttttcattgtaccatgaaatatccagaacatacttatatgtaaagta
ttatttattgaatctacaaaaacaacaaataattttaaatataaggattttctagatatattgcacggagaata
tacaaatagcaaaattggccaaggccaagggccaagagaatatccgaacttaatttcaggaattgaatggtttgctaga
atgtgatatttgaagcatcacataaaaatgatggacaataaatttgccataaagtcaaattagctgaaatcct
ggattttttctgtaaatctgcaacctagtctgctagccaggatccacaagtcctgttccactgtgcctgt
ttctcctttatttctaagtggaaaaagtattagccaccatcttacctcacagtgatgttgtgggacatgtggaagc
acttaagttttttcatcataacataataatttcaagtgtaacttattattactagtaaccatattttaataagtgttata
taagcatcaaatatttgtcaagaattgcaagaattgaaaatagaagatgaatcattgattgaatagttataaagatgttata
gtaaattatttatttttagatattaaatgatgttttaaatgatgtttcattaagcaacaacaataattttagtataagtacattattgttt
aaacaattggtaccagttaaatttcatttcagataaacaacaacaataattttagtataagtacattattgttt
atctgaaatttaattgaactaacatccagtttgatactccccagtctcttgtcattgccagctgtgttggtagtgct
gtgttgaattacgaataatgagttagaactattagaacagccaaactccacagtcaatattgactgcattttaaatacaaggctt
ggttgaaactgttttattatgtacaaatagattcttataatatttttttactgttttctgattgtatgaaataaaa
tatattttaactttaagatgttttatgtctctccaaatttttttttactgtttctgattgtatgaaataaaa
gtaaatatgaaacattaaaatataattttgtcaaagtaaagtaaaaaaaaaaaa  (SEQ ID NO:247)

Fig. 14A 193 (27-mer #193 in Fig 11)
gcagttttgccaaggagtgctaagaacttagatgtcagtg (SEQ ID NO:248)

5'   CCAAGGAGUGCUAAAGAACUUAGat  (SEQ ID NO:249)
3'   ACGGUUCCUCACGAUUUCUUGAAUCUA (SEQ ID NO:250)

717 (27-mer #717 in Fig 11)
aagggccaagagaatatccgaactttaatttcaggaattga (SEQ ID NO:251)

5'   GAGAAUAUCCGAACUUUAAUUUCag  (SEQ ID NO:252)
3'   UUCUCUUAUAGGCUUGAAAUUAAAGUC (SEQ ID NO:253)

880 (27-mer #880 in Fig 11)
gtctgctagccaggatccacaagtccttgttccactgtgcc (SEQ ID NO:254)

5'   CCAGGAUCCACAAGUCCUUGUUCca  (SEQ ID NO:255)
3'   UCGGUCCUAGGUGUUCAGGAACAAGGU (SEQ ID NO:256)

Fig. 14A₂

RSV strain A2

1: M74568. Human respiratory syncytial virus (RSV). [gi:333959]
LOCUS       RSHSEQ                 15222 bp ss-RNA     linear   VRL 03-AUG-1993
DEFINITION  Human respiratory syncytial virus nonstructural protein 1,
            nonstructural protein 2, nucleocapsid protein,
            phosphoprotein, matrix protein, small hydrophobic protein,
            glycoprotein, fusionglycoprotein, 22K/M2 protein and L protein
            mRNA, complete cds.
ACCESSION   M74568
VERSION     M74568.1  GI:333959
KEYWORDS    22K/M2 protein; L protein; fusion glycoprotein;
glycoprotein; matrix protein; nonstructural protein 1; nonstructural protein
2; nucleocapsid protein; phosphoprotein; small hydrophobic protein.
    SOURCE    Human respiratory syncytial virus

NS1 gene

ATG*GGCAGCAATTCATTGAGTATG*ATAAAAGTTAGATTACAAAATTTGTTTGACAATGATGAAGTAGCATT
GTTAAAAATAACATGCTATACTGATAAATTAATACATTTAACTAATGCTTTGGCTAAGGCAGTGATACA**TACAATCA
AATTGAATGGCATT**GTGTTTGTGCATGTTATTACAAGTAGTGATATTTGCCCTAATAATAATATTGTAGTAAAATCC
AATTTCACAACAATGCCAGTACTACAAAATGGAGGTTATATATGGGAAATGATGGAATTAACACATTGCTCTCAACC
TAATGGTCTACTAGATGACAATTGTGAAATTAAATTCTCCAAAAAACTAAGTGATTCAACAATGACCAATTATATGA
ATCAATTATCTGAATTACTTGGATTTGATCTTAATCCATAA   (SEQ ID NO:257)

Italics = NS1-002 derived from Mohapatra, Nat Med 11:56 (2005)

002 (NS1-002)
    ATG*GGCAGCAATTCATTGAGTATG*ATAAAA   (SEQ ID NO:258)

5'   GGCAGCAAUUCAUUGAGUAUGAUaa   (SEQ ID NO:259)
3'   ACCCGUCGUUAAGUAACUCAUACUAUU   (SEQ ID NO:260)

141 (NS1-141)
TACATACAATCAAATTGAATGGCATTGTGTTTGTGC   (SEQ ID NO:261)

5'   CAAUCAAAUUGAAUGGCAUUGUGUtt   (SEQ ID NO:262)

*Fig. 14B₁*

3' AUGUUAGUUUAACUUACCGUAACACAA (SEQ ID NO:263)

347 (NS1-347)
AAAAAACTAAGTGATTCAACAATGACCAATTATAT (SEQ ID NO:264)

5' CUAAGUGAUUCAACAAUGACCAAtt (SEQ ID NO:265)
3' UUGAUUCACUAAGUUGUUACUGGUUAA (SEQ ID NO:266)

391 (NS1-391)
TTATCTGAATTACTTGGATTTGATCTTAATCCATA (SEQ ID NO:267)

5' GAAUUACUUGGAUUUGAUCUUAAtc (SEQ ID NO:268)
3' UUCUUAAUGAACCUAAACUAGAAUUAG (SEQ ID NO:269)

NS2 gene

ATGGACACAACCCACAATGATAATACACCACAAAGACTGATGATCACAGACATGAGACCGTTGTCACTTGA
GACCATAATAACATCACTAACCAGAGACATCATAACACACAAATTTATATACTTGATAAATCATGAATGCATAGTGA
GAAAACTTGATGAAAGACAGGCCACATTTACATTCCTGGTCAACTATGAAATGAAACTATTACACAAAGTAGGAAGC
ACTAAATATAAAAAATATACTGAATACAACACAAAATATGGCACTTTCCCTATGCCAATATTCATCAATCATGATGG
GTTCTTAGAATGCATTGGCATTAAGCCTACAAAGCATACTCCCATAATATACAAGTATGATCTCAATCCATAA
(SEQ ID NO:270)

N gene

ATGGCTCTTAGCAAAGTCAAGTTGAATGATACACTCAACAAAGATCAACTTCTGTCATCCAGCAAATACAC
CATCCAACGGAGCACAGGAGATAGTATTGATACTCCTAATTATGATGTGCAGAAACACATCAATAAGTTATGTGGCA
TGTTATTAATCACAGAAGATGCTAATCATAAATTCACTGGGTTAATAGGTATGTTATATGCGATGTCTAGGTTAGGA
AGAGAAGACACCATAAAAATACTCAGAGATGCGGGATATCATGTAAAAGCAAATGGAGTAGATGTAACAACACATCG
TCAAGACATTAATGGAAAAGAAATGAAATTTGAAGTGTTAACATTGGCAAGCTTAACAACTGAAATTCAAATCAACA
TTGAGATAGAATCTAGAAAATCCTACAAAAAAATGCTAAAAGAAATGGGAGAGGTAGCTCCAGAATAC**AGGCATGAC
TCTCCTGATTGTGG**GATGATAATATTATGTATAGCAGCATTAGTAATAACTAAATTAGCAGCAGGGGACAGATCTGG
TCTTACAGCCGTGATTAGGAGAGCTAATAATGTCCTAAAAAATGAAATGAAACGTTACA**AAGGCTTACTACCCAAGG
ACATA**GCCAACAGCTTCTATGAAGTGTTTGAAAAACATCCCCACTTTATAGATGTTTTTGTTCATTTTGGTATAGCA
CAATCTTCTACCAGAGGTGGCAGTAGAGTTGAAGGGATTTTTGCAGGATTGTTTATGAATGCCTATGGTGCAGGGCA
AGTGATGTTACGGTGGGGAGTCTTAGCAAAATCAATTAAAAATATTATGTTAGGACATGCTAGTGTGCAAGCAGAA**A
TGGAACAAGTTGTTGAGGTTTA**TGAATATGCCCAAAAATTGGGTGGTGAAGCAGGATTCTACCATATATTGAACAAC

*Fig. 14B₂*

CCAAAAGCATCATTATTATCTTTGACTCAATTTCCTCACTTCTCCAGTGTAGTATTAGGCAATGCTGCTGGCCTAGG
CATAATGGGAGAGTACAGAGGTACACCGAGGAATCAAGATCTATATGATGCAGCAAAGGCATATGCTGAACAACTCA
AAGAAAATGGTGTGATTAACTACAGTGTACTAGACTTGACAGCAGAAGAACTAGAGGCTATCAAACATCAGCTTAAT
CCAAAAGATAATGATGTAGAGCTTTGA  (SEQ ID NO:271)

448 (N-448)

ATACAGGCATGACTCTCCTGATTGTGGGATGATAATATTA  (SEQ ID NO:272)

5'    GCAUGACUCUCCUGAUUGUGGGAtg    (SEQ ID NO:273)
3'    UCCGUACUGAGAGGACUAACACCCUAC  (SEQ ID NO:274)

593 (N-563)
TACAAAGGCTTACTACCCAAGGACATAGCCAACAGCTTCTA  (SEQ ID NO:275)

5'    GGCUUACUACCCAAGGACAUAGCca    (SEQ ID NO:276)
3'    UUCCGAAUGUAGGGUUCCUGUAUCGGU  (SEQ ID NO:277)

841 (N-841)
AGAAATGGAACAAGTTGTTGAGGTTTATGAATATGCCCAAA  (SEQ ID NO:278)

5'    GGAACAAGUUGUUGAGGUUUAUGaa    (SEQ ID NO:279)
3'    UACCUUGUUCAACAACUCCAAAUACUU  (SEQ ID NO:280)

P gene

ATGGAAAAGTTTGCTCCTGAATTCCATGGAGAAGATGCAAACAACAGGGCTACTAAATTCCTAGAATCAAT
AAAGGGCAAATTCACATCACCCAAAGATCCCAAGAAAAAAGATAGTATCATATCTGTCAACTCAATAGATATAGAAG
TAACCAAAGAAAGCCCTATAACATCAAATTCAACTATTATCAACCCAACAAATGAGACAGATGATACTGCAGGGAAC
AAGCCCAATTATCAAAGAAAACCTCTAGTAAGTTTCAAAGAAGACCCTACACCAAGTGATAATCCCTTTTCTAAACT
ATACAAAGAAACCATAGAAACATTTGATAACAATGAAGAAGAATCCAGCTATTCATACGAAGAAATAAATGATCAGA
CAAACGATAATATAACAGCAAGATTAGATAGGATTGATGAAAAATTAAGTGAAATACTAGGAATGCTTCACACATTA
GTAGTGGCAAGTGCAGGACCTACATCTGCTCGGGATGGTATAAGAGATGCCATGGTTGGTTTAAGAGAAGAAATGAT
AGAAAAAATCAGAACTGAAGCATTAATGACCAATGACAGATTAGAAGCTATGGCAAGACTCAGGAATGAGGAAAGTG
AAAAGATGGCAAAAGACACATCAGATGAAGTGTCTCTCAATCCAACATCAGAGAAATTGAACAACCTATTGGAAGGG
AATGATAGTGACAATGATCTATCACTTGAAGATTTCTGA  (SEQ ID NO:281)

*Fig. 14B₃*

381 = RSV-p P-381 from Barik et al, Nat Med 11:50

26 (P-26)
TTCCATGGAGAAGATGCAAACAACAGGGCTACTAAA    (SEQ ID NO:282)

5'    GGAGAAGAUGCAAACAACAGGGCta    (SEQ ID NO:283)
3'    UACCUCUUCUACGUUUGUUGUCCCGUA  (SEQ ID NO:284)

266 (P-266)
AAAGAAGACCCTACACCAAGTGATAATCCCTTTTC    (SEQ ID NO:285)

5'    GACCCUACACCAAGUGAUAAUCCct    (SEQ ID NO:286)
3'    UUCUGGGAUGUGGUUCACUAUUAGGGA  (SEQ ID NO:287)

381 (P-381)
GACAAACGATAATATAACAGCAAGATTAGATAGGA    (SEQ ID NO:288)

5'    CGAUAAUAUAACAGCAAGAUUAGat    (SEQ ID NO:289)
3'    UUGCUAUUAUAUUGUCGUUCUAAUCUA  (SEQ ID NO:290)

551 (P-551)
ACTGAAGCATTAATGACCAATGACAGATTAGAAG    (SEQ ID NO:291)

5'    GCAUUAAUGACCAAUGACAGAUUag    (SEQ ID NO:292)
3'    UUCGUAAUUACUGGUUACUGUCUAAUC  (SEQ ID NO:293)

L gene
    ATGGATCCCATTATTAATGGAAATTCTGCTAATGTTTATCTAACCGATAGTTATTTAAAAGGTGTTATCTC
TTTCTCAGAGTGTAATGCTTTAGGAAGTTACATATTCAATGGTCCTTATCTCAAAAATGATTATACCAACTTAATTA
GTAGACAAAATCCATTAATAGAACACATGAATCTAAAGAAACTAAATATAACACAGTCCTTAATATCTAAGTATCAT
AAAGGTGAAATAAAATTAGAAGAACCTACTTATTTTCAGTCATTACTTATGACATACAAGAGTATGACCTCGTCAGA
ACAGATTGCTACCACTAATTTACTTAAAAAGATAATAAGAAGAGCTATAGAAATAAGTGATGTCAAAGTCTATGCTA
TATTGAATAAACTAGGGCTTAAAGAAAAGGACAAGATTAAATCCAACAATGGACAAGATGAAGACAACTCAGTTATT
ACGACCATAATCAAAGATGATATACTTTCAGCTGTTAAAGATAATCAATCTCATCTTAAAGCAGACAAAAATCACTC
TACAAAACAAAAAGACACAATCAAAACAACACTCTTGAAGAAATTGATGTGTTCAATGCAACATCCTCCATCATGGT
TAATACATTGGTTTAACTTATACACAAAATTAAACAACATATTAACACAGTATCGATCAAATGAGGTAAAAAACCAT

*Fig. 14B₄*

```
GGGTTTACATTGATAGATAATCAAACTCTTAGTGGATTTCAATTTATTTTGAACCAATATGGTTGTATAGTTTATCA
TAAGGAACTCAAAAGAATTACTGTGACAACCTATAATCAATTCTTGACATGGAAAGATATTAGCCTTAGTAGATTAA
ATGTTTGTTTAATTACATGGATTAGTAACTGCTTGAACACATTAAATAAAAGCTTAGGCTTAAGATGCGGATTCAAT
AATGTTATCTTGACACAACTATTCCTTTATGGAGATTATATACTAAAGCTATTTCACAATGAGGGGTTCTACATAAT
AAAAGAGGTAGAGGGATTTATTATGTCTCTAATTTTAAATATAACAGAAGAAGATCAATTCAGAAAACGATTTTATA
ATAGTATGCTCAACAACATCACAGATGCTGCTAATAAAGCTCAGAAAAATCTGCTATCAAGAGTATGTCATACATTA
TTAGATAAGACAGTGTCCGATAATATAATAAATGGCAGATGGATAATTCTATTAAGTAAGTTCCTTAAATTAATTAA
GCTTGCAGGTGACAATAACCTTAACAATCTGAGTGAACTATATTTTTTGTTCAGAATATTTGGACACCCAATGGTAG
ATGAAAGACAAGCCATGGATGCTGTTAAAATTAATTGCAATGAGACCAAATTTTACTTGTTAAGCAGTCTGAGTATG
TTAAGAGGTGCCTTTATATATAGAATTATAAAAGGGTTTGTAAATAATTACAACAGATGGCCTACTTTAAGAAATGC
TATTGTTTTACCCTTAAGATGGTTAACTTACTATAAACTAAACACTTATCCTTCTTTGTTGGAACTTACAGAAAGAG
ATTTGATTGTGTTATCAGGACTACGTTTCTATCGTGAGTTTCGGTTGCCTAAAAAAGTGGATCTTGAAATGATTATA
AATGATAAAGCTATATCACCTCCTAAAAATTTGATATGGACTAGTTTCCCTAGAAATTACATGCCATCACACATACA
AAACTATATAGAACATGAAAAATTAAAATTTTCCGAGAGTGATAAATCAAGAAGAGTATTAGAGTATTATTTAAGAG
ATAACAAATTCAATGAATGTGATTTATACAACTGTGTAGTTAATCAAAGTTATCTCAACAACCCTAATCATGTGGTA
TCATTGACAGGCAAAGAAAGAGAACTCAGTGTAGGTAGAATGTTTGCAATGCAACCGGGAATGTTCAGACAGGTTCA
AATATTGGCAGAGAAAATGATAGCTGAAAACATTTTACAATTCTTTCCTGAAAGTCTTACAAGATATGGTGATCTAG
AACTACAAAAAATATTAGAATTGAAAGCAGGAATAAGTAACAAATCAAATCGCTACAATGATAATTACAACAATTAC
ATTAGTAAGTGCTCTATCATCACAGATCTCAGCAAATTCAATCAAGCATTTCGATATGAAACGTCATGTATTTGTAG
TGATGTGCTGGATGAACTGCATGGTGTACAATCTCTATTTTCCTGGTTACATTTAACTATTCCTCATGTCACAATAA
TATGCACATATAGGCATGCACCCCCCTATATAGGAGATCATATTGTAGATCTTAACAATGTAGATGAACAAAGTGGA
TTATATAGATATCACATGGGTGGCATCGAAGGGTGGTGTCAAAAACTATGGACCATAGAAGCTATATCACTATTGGA
TCTAATATCTCTCAAAGGGAAATTCTCAATTACTGCTTTAATTAATGGTGACAATCAATCAATAGATATAAGCAAAC
CAATCAGACTCATGGAAGGTCAAACTCATGCTCAAGCAGATTATTTGCTAGCATTAAATAGCCTTAAATTACTGTAT
AAAGAGTATGCAGGCATAGGCCACAAATTAAAAGGAACTGAGACTTATATATCACGAGATATGCAATTTATGAGTAA
AACAATTCAACATAACGGTGTATATTACCCAGCTAGTATAAAGAAAGTCCTAAGAGTGGGACCGTGGATAAACACTA
TACTTGATGATTTCAAAGTGAGTCTAGAATCTATAGGTAGTTTGACACAAGAATTAGAATATAGAGGTGAAAGTCTA
TTATGCAGTTTAATATTTAGAAATGTATGGTTATATAATCAGATTGCTCTACAATTAAAAAATCATGCATTATGTAA
CAATAAACTATATTTGGACATATTAAAAGGTTCTGAAACACTTAAAAACCTTTTTTAATCTTGATAATATTGATACAG
CATTAACATTGTATATGAATTTACCCATGTTATTTGGTGGTGGTGATCCCAACTTGTTATATCGAAGTTTCTATAGA
AGAACTCCTGACTTCCTCACAGAGGCTATAGTTCACTCTGTGTTCATACTTAGTTATTATACAAACCATGACTTAAA
AGATAAACTTCAAGATCTGTCAGATGATAGATTGAATAAGTTCTTAACATGCATAATCACGTTTGACAAAAACCCTA
ATGCTGAATTCGTAACATTGATGAGAGATCCTCAAGCTTTAGGGTCTGAGAGACAAGCTAAAATTACTAGCGAAATC
AATAGACTGGCAGTTACAGAGGTTTTGAGTACAGCTCCAAACAAAATATTCTCCAAAAGTGCACAACATTATACTAC
TACAGAGATAGATCTAAATGATATTATGCAAAATATAGAACCTACATATCCTCATGGGCTAAGAGTTGTTTATGAAA
GTTTACCCTTTTATAAAGCAGAGAAAATAGTAAATCTTATATCAGGTACAAAATCTATAACTAACATACTGGAAAAA
.ACTTCTGCCATAGACTTAACAGATATTGATAGAGCCACTGAGATGATGAGGAAAAACATAACTTTGCTTATAAGGAT
ACTTCCATTGGATTGTAACAGAGATAAAAGAGAGATATTGAGTATGGAAAACCTAAGTATTACTGAATTAAGCAAAT
```

*Fig. 14B₅*

```
ATGTTAGGGAAAGATCTTGGTCTTTATCCAATATAGTTGGTGTTACATCACCCAGTATCATGTATACAATGGACATC
AAATATACTACAAGCACTATATCTAGTGGCATAATTATAGAGAAATATAATGTTAACAGTTTAACACGTGGTGAGAG
AGGACCCACTAAACCATGGGTTGGTTCATCTACACAAGAGAAAAAAACAATGCCAGTTTATAATAGACAAGTCTTAA
CCAAAAAACAGAGAGATCAAATAGATCTATTAGCAAAATTGGATTGGGTGTATGCATCTATAGATAACAAGGATGAA
TTCATGGAAGAACTCAGCATAGGAACCCTTGGGTTAACATATGAAAAGGCCAAGAAATTATTTCCACAATATTTAAG
TGTCAATTATTTGCATCGCCTTACAGTCAGTAGTAGACCATGTGAATTCCCTGCATCAATACCAGCTTATAGAACAA
CAAATTATCACTTTGACACTAGCCCTATTAATCGCATATTAACAGAAAAGTATGGTGATGAAGATATTGACATAGTA
TTCCAAAACTGTATAAGCTTTGGCCTTAGTTTAATGTCAGTAGTAGAACAATTTACTAATGTATGTCCTAACAGAAT
TATTCTCATACCTAAGCTTAATGAGATACATTTGATGAAACCTCCCATATTCACAGGTGATGTTGATATTCACAAGT
TAAAACAAGTGATACAAAAACAGCATATGTTTTTACCAGACAAAATAAGTTTGACTCAATATGTGGAATTATTCTTA
AGTAATAAAACACTCAAATCTGGATCTCATGTTAATTCTAATTTAATATTGGCACATAAAATATCTGACTATTTTCA
TAATACTTACATTTTAAGTACTAATTTAGCTGGACATTGGATTCTGATTATACAACTTATGAAAGATTCTAAAGGTA
TTTTTGAAAAAGATTGGGGAGAGGGATATATAACTGATCATATGTTTATTAATTTGAAAGTTTTCTTCAATGCTTAT
AAGACCTATCTCTTGTGTTTCATAAAGGTTATGGCAAAGCAAAGCTGGAGTGTGATATGAACACTTCAGATCTTCT
ATGTGTATTGGAATTAATAGACAGTAGTTATTGGAAGTCTATGTCTAAGGTATTTTTAGAACAAAAAGTTATCAAAT
ACATTCTTAGCCAAGATGCAAGTTTACATAGAGTAAAAGGATGTCATAGCTTCAAATTATGGTTTCTTAAACGTCTT
AATGTAGCAGAATTCACAGTTTGCCCTTGGGTTGTTAACATAGATTATCATCCAACACATATGAAAGCAATATTAAC
TTATATAGATCTTGTTAGAATGGGATTGATAAATATAGATAGAATACACATTAAAAATAAACACAAATTCAATGATG
AATTTTATACTTCTAATCTCTTCTACATTAATTATAACTTCTCAGATAATACTCATCTATTAACTAAATATATAAGG
ATTGCTAATTCTGAATTAGAAAATAATTACAACAAATTATATCATCCTACACCAGAAACCCTAGAGAATATACTAGC
CAATCCGATTAAAAGTAATGACAAAAAGACACTGAATGACTATTGTATAGGTAAAAATGTTGACTCAATAATGTTAC
CATTGTTATCTAATAAGAAGCTTATTAAATCGTCTGCAATGATTAGAACCAATTACAGCAAACAAGATTTGTATAAT
TTATTCCCTATGGTTGTGATTGATAGAATTATAGATCATTCAGGCAATACAGCCAAATCCAACCAACTTTACACTAC
TACTTCCCACCAAATATCTTTAGTGCACAATAGCACATCACTTTACTGCATGCTTCCTTGGCATCATATTAATAGAT
TCAATTTTGTATTTAGTTCTACAGGTTGTAAAATTAGTATAGAGTATATTTAAAAGATCTTAAAATTAAAGATCCC
AATTGTATAGCATTCATAGGTGAAGGAGCAGGGAATTTATTATTGCGTACAGTAGTGGAACTTCATCCTGACATAAG
ATATATTTACAGAAGTCTGAAAGATTGCAATGATCATAGTTTACCTATTGAGTTTTTAAGGCTGTACAATGGACATA
TCAACATTGATTATGGTGAAAATTTGACCATTCCTGCTACAGATGCAACCAACAACATTCATTGGTCTTATTTACAT
ATAAAGTTTGCTGAACCTATCAGTCTTTTTGTCTGTGATGCCGAATTGTCTGTAACAGTCAACTGGAGTAAAATTAT
AATAGAATGGAGCAAGCATGTAAGAAAGTGCAAGTACTGTTCCTCAGTTAATAAATGTATGTTAATAGTAAAATATC
ATGCTCAAGATGATATTGATTTCAAATTAGACAATATAACTATATTAAAAACTTATGTATGCTTAGGCAGTAAGTTA
AAGGGATCGGAGGTTTACTTAGTCCTTACAATAGGTCCTGCGAATATATTCCCAGTATTTAATGTAGTACAAAATGC
TAAATTGATACTATCAAGAACCAAAAATTTCATCATGCCTAAGAAAGCTGATAAAGAGTCTATTGATGCAAATATTA
AAAGTTTGATACCCTTTCTTTGTTACCCTATAACAAAAAAAGGAATTAATACTGCATTGTCAAAACTAAAGAGTGTT
GTTAGTGGAGATATACTATCATATTCTATAGCTGGACGTAATGAAGTTTTCAGCAATAAACTTATAAATCATAAGCA
TATGAACATCTTAAAATGGTTCAATCATGTTTTAAATTTCAGATCAACAGAACTAAACTATAACCATTTATATATGG
TAGAATCTACATATCCTTACCTAAGTGAATTGTTAAACAGCTTGACAACCAATGAACTTAAAAAACTGATTAAAATC
ACAGGTAGTCTGTTATACAACTTTCATAATGAATAA (SEQ ID NO:294)
```

*Fig. 14B6*

1647 (L-1647)
TGATATGGACTAGTTTCCCTAGAAATTACATGCCATC  (SEQ ID NO:295)

5'    GGACUAGUUUCCCUAGAAAUUACat  (SEQ ID NO:296)
3'  UACCUGAUCAAAGGGAUCUUUAAUGUA  (SEQ ID NO:297)

2021 (L-2021)
TTGAAAGCAGGAATAAGTAACAAATCAAATCGCTACAATG  (SEQ ID NO:298)

5'    GCAGGAAUAAGUAACAAAUCAAAtc  (SEQ ID NO:299)
3'  UUCGUCCUUAUUCAUUGUUUAGUUUAG  (SEQ ID NO:300)

5277 (L-5277)
TTAGAACCAATTACAGCAAACAAGATTTGTATAATTT  (SEQ ID NO:301)

5'    CCAAUUACAGCAAACAAGAUUUGta  (SEQ ID NO:302)
3'  UUGGUUAAUGUCGUUUGUUCUAAACAU  (SEQ ID NO:303)

Fig. 14B₇ shRNA sequences designed against Influenza strain A/Puerto rico/8/34, H1N1.

| Name | | Sequences for shRNAs targeting Influenza A virus genes | | | |
|---|---|---|---|---|---|
| | Termination | siRNA sense | Loop | siRNA antisense | 23 nt mU6 |
| PB1-a | ctcgagaaaaa | AAGACCAGTCGGGATATCCAG (SEQ ID NO:304) | tgacaggaag | CTGGATATCCCGACTGGTCTT (SEQ ID NO:313) | caaaacaaggctttctccaagg |
| PB1-b | ctcgagaaaaa | AAAGAGGAGTTCACTGAGATC (SEQ ID NO:305) | tgacaggaag | GATCTCAGTGAACTCCTCTTT (SEQ ID NO:314) | caaaacaaggctttctccaagg |
| PB2-a | ctcgagaaaaa | AACTGAAGACCCAGATGAAGG (SEQ ID NO:306) | tgacaggaag | CCTTCATCTGGGTCTTCAGTT (SEQ ID NO:315) | caaaacaaggctttctccaagg |
| PB2-b | ctcgagaaaaa | AATTGGGCAAGGAGACGTGGT (SEQ ID NO:307) | tgacaggaag | ACCACGTCTCCTTGCCCAATT (SEQ ID NO:316) | caaaacaaggctttctccaagg |
| m-37 | ctcgagaaaaa | AACCGAGGTCGAAACGTACGT (SEQ ID NO:308) | tgacaggaag | ACGTACGTTTCGACCTCGGTT (SEQ ID NO:317) | caaaacaaggctttctccaagg |
| m-598 | ctcgagaaaaa | AAATGGCTGGATCGAGTGAGC (SEQ ID NO:309) | tgacaggaag | GCTCACTCGATCCAGCCATTT (SEQ ID NO:318) | caaaacaaggctttctccaagg |
| m-c | ctcgagaaaaa | AACAGCAGAATGCTGTGGATG (SEQ ID NO:310) | tgacaggaag | CATCCACAGCATTCTGCTGTT (SEQ ID NO:319) | caaaacaaggctttctccaagg |
| PA-2078 | ctcgagaaaaa | AAGCAATTGAGGAGTGCCTGA (SEQ ID NO:311) | tgacaggaag | TCAGGCACTCCTCAATTGCTT (SEQ ID NO:320) | caaaacaaggctttctccaagg |
| PA-b | ctcgagaaaaa | AACTCCTTCCTCACACATGCA (SEQ ID NO:312) | tgacaggaag | TGCATGTGTGAGGAAGGAGTT (SEQ ID NO:321) | caaaacaaggctttctccaagg |

PB=basic polymerase; PA=acidic polymerase; m=matrix.

Fig. 15

Fig. 16 shRNA designed against human angiotensin converting enzyme 2 (ACE2)

| hACE2 | Termination | siRNA sense | Loop | siRNA antisense | 23 nt mU6 |
|---|---|---|---|---|---|
| 65 | ctcgagaaaaa | AAGTCATTCAGTGGATGTGATCT (SEQ ID NO:322) | tgacaggaag | AGATCACATCCACTGAATGACTT (SEQ ID NO:327) | caaaacaaggctttctccaagg |
| 690 | ctcgagaaaaa | ATGAGGACTATGGGGATTATTGG (SEQ ID NO:323) | tgacaggaag | CCAATAATCCCCATAGTCCTCAT (SEQ ID NO:328) | caaaacaaggctttctccaagg |
| 1338* | ctcgagaaaaa | CAGCCACACCTAAGCATTTAAAA (SEQ ID NO:324) | tgacaggaag | TTTTAAATGCTTAGGTGTGGCTG (SEQ ID NO:329) | caaaacaaggctttctccaagg |
| 2001 | ctcgagaaaaa | ATGAATGGAACGACAATGAAATG (SEQ ID NO:325) | tgacaggaag | CATTTCATTGTCGTTCCATTCAT (SEQ ID NO:330) | caaaacaaggctttctccaagg |
| 2798 | ctcgagaaaaa | GGCTGTTCAGGGATAATCTAAAT (SEQ ID NO:326) | tgacaggaag | ATTTAGATTATCCCTGAACAGCC (SEQ ID NO:331) | caaaacaaggctttctccaagg |

RNA INTERFERENCE IN RESPIRATORY EPITHEIAL CELLS

CROSS-REFERENCE TO RELATED APPLICATION

This application is related to and claims priority under 35 U.S.C. § 119(e) to U.S. Provisional Application No. 60/586,554 filed on Jul. 9, 2004, and U.S. Provisional Application No. 60/622,758 filed on Oct. 28, 2004, both of which are incorporated by reference herein.

STATEMENT REGARDING FEDERALLY SPONSORED RESEARCH AND DEVELOPMENT

The present invention was made in part with Government support under Grant Number 1PO1 AI060699-01 awarded by the National Institutes of Health. The Government may have certain rights in this invention.

FIELD OF THE INVENTION

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

The present invention pertains to compositions and methods for gene-specific inhibition of gene expression by double-stranded ribonucleic acid (dsRNA) effector molecules. The compositions and methods are useful in modulating gene expression in a variety of applications, including therapeutic, diagnostic, target validation, and genomic discovery.

BACKGROUND OF THE INVENTION

Post-transcription gene silencing occurs when double stranded RNA (dsRNA) is introduced or naturally expressed in cells. RNA interference (RNAi) has been described in plants, nematodes, and *Drosophila*. This process serves at least two roles. It is used as an innate defense mechanism, and it is also used during development. RNAi may regulate developmental expression of genes via the processing of small, temporally expressed RNAs. Harnessing this ability to respond specifically to dsRNA for target mRNA degradation has been a major advance, allowing for the rapid evaluation of gene function.

Despite the attention given to RNAi research recently, the field is still in the early stages of development. Not all siRNA molecules are capable of targeting the destruction of their complementary RNAs in a cell. As a result, complex sets of rules have been developed for designing RNAi molecules that will be effective. Those having skill in the art expect to test multiple siRNA molecules to find functional compositions. (Ji et al., 2003) Some artisans pool several siRNA preparations together to increase the chance of obtaining silencing in a single study (Ji et al., 2003). Such pools typically contain 20 nM of a mixture of siRNA oligonucleotide duplexes or more (Ji et al., 2003), despite the fact that a siRNA molecule can work at concentrations of 1 nM or less (Holen et al., 2002). This technique can lead to artifacts caused by interactions of the siRNA sequences with other cellular RNAs ("off target effects") (Scherer et al., 2003). Off target effects can occur when the RNAi oligonucleotides have homology to unintended targets or when the RISC complex incorporates the unintended strand from and RNAi duplex (Scherer et al., 2003). Generally, these effects tend to be more pronounced when higher concentrations of RNAi duplexes are used (Scherer et al., 2003).

In addition, the duration of the effect of an effective RNAi treatment is limited to about four days (Holen et al., 2002). Thus, researchers must carry out siRNA experiments within 2-3 days of transfection with an siRNA duplex or work with plasmid or viral expression vectors to obtain longer term silencing.

SUMMARY OF THE INVENTION

RNAi targets the specific degradation of messenger RNAs (mRNAs) in the cell cytoplasm. Alternatively, RNAi can inhibit the expression of proteins through inhibition of protein expression (e.g., microRNAs). Thus, any disease state that involves changes in mRNA expression may be targeted. For example, an mRNA encoding a deleterious protein could be targeted for degradation.

The present invention is directed to compositions and methods for selectively reducing the expression of a gene product from a desired target gene in a eukaryotic cell, as well as for treating diseases caused by the expression of the gene. More particularly, the invention is directed to compositions that contain double stranded RNA ("dsRNA"), and methods for preparing them, that are capable of reducing the expression of target genes in eukaryotic cells.

Thus, the present invention provides novel compositions for RNA interference. The compositions comprise dsRNA that is a precursor molecule, i.e., the dsRNA of the present invention is processed in vivo to produce an active siRNA. The dsRNA is processed by Dicer to an active siRNA that is incorporated into the RISC complex for RNA interference of a target gene. The precursor molecule is also termed a precursor RNAi molecule herein.

The present invention presents a method to specifically target the degradation of mRNA in the respiratory epithelium as a means to treat a variety of disorders. For the purpose of this invention, the respiratory epithelium refers to tissues including the epithelial cells lining the sinuses, the nasal airways, the conducting airways and the alveolar epithelium. The delivery of RNAi to the airway epithelium has utility in the prevention or treatment of a number of disease states. Specifically, methods are presented for the delivery of inhibitory nucleic acids to pulmonary epithelia. In certain embodiments, RNAi is delivered to the nasal or intrapulmonary epithelia by direct topical application, aerosol, dry powder, electroporation, in a polymer or excipient, or other methods.

In certain embodiments of the present invention, the RNAi targets pro-inflammatory processes, viral pathogens, and other agents involved in airway diseases. Examples of such target diseases include asthma, cystic fibrosis, or interstitial lung disease. The specificity of the RNAi for the targeted mRNA is enabled through the use of complementary sequences.

These methods are used in the treatment of a variety of pulmonary diseases primarily or secondarily involving the pulmonary epithelium. Examples of pro-inflammatory diseases include asthma, cystic fibrosis, chronic obstructive pulmonary disease (COPD), and interstitial lung disease. In one embodiment, the mRNAs of proteins involved in pathways of inflammation, such as NF-Kappa B, are targeted. In addition these methods are used in targeting the destruction of RNAs of respiratory pathogens, including viruses, and thereby preventing or treating a variety of respiratory infections. The invention further provides methods of delivery of this RNAi to the respiratory epithelium in vitro and in vivo.

In one embodiment, the dsRNA, i.e., the precursor RNAi molecule, has several properties that enhance its processing by Dicer. According to this embodiment, the dsRNA has a length sufficient such that it is processed by Dicer to produce an siRNA and at least one of the following properties: (i) the dsRNA is asymmetric, e.g., has a 3' overhang on the antisense strand and (ii) the dsRNA has a modified 3' end on the sense strand to direct orientation of Dicer binding and processing of the dsRNA to an active siRNA. In certain embodiments, the sense strand has 22-28 nucleotides and the antisense strand has 24-30 nucleotides. In one embodiment, the dsRNA has an overhang on the 3' end of the antisense strand. In another embodiment, the sense strand is modified for Dicer binding and processing by suitable modifiers located at the 3' end of the sense strand. Suitable modifiers include nucleotides such as deoxyribonucleotides, acyclonucleotides and the like, and sterically hindered molecules, such as fluorescent molecules and the like. When nucleotide modifiers are used, they replace ribonucleotides in the dsRNA such that the length of the dsRNA does not change. In another embodiment, the dsRNA has an overhang on the 3' end of the antisense strand and the sense strand is modified for Dicer processing. In another embodiment, the 5' end of the sense strand has a phosphate. The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are in the 21-nucleotide region adjacent to the 3' end of the antisense strand and are sufficiently complementary to a nucleotide sequence of the RNA produced from the target gene. Further in accordance with this embodiment, the dsRNA, i.e., the precursor RNAi molecule, may also have one or more of the following additional properties: (a) the antisense strand has a right shift from the typical 21-mer (i.e., the antisense strand includes nucleotides on the right side of the molecule when compared to the typical 21-mer), (b) the strands may not be completely complementary, i.e., the strands may contain simple mismatch pairings and (c) base modifications such as locked nucleic acid(s) may be included in the 5' end of the sense strand.

In another embodiment, the dsRNA, i.e., the precursor RNAi molecule, has several properties that enhance its processing by Dicer. According to this embodiment, the dsRNA has a length sufficient such that it is processed by Dicer to produce an siRNA and at least one of the following properties: (i) the dsRNA is asymmetric, e.g., has a 3' overhang on the sense strand and (ii) the dsRNA has a modified 3' end on the antisense strand to direct orientation of Dicer binding and processing of the dsRNA to an active siRNA. According to this embodiment, the sense strand has 24-30 nucleotides and the antisense strand has 22-28 nucleotides. In one embodiment, the dsRNA has an overhang on the 3' end of the sense strand. In another embodiment, the antisense strand is modified for Dicer binding and processing by suitable modifiers located at the 3' end of the antisense strand. Suitable modifiers include nucleotides such as deoxyribonucleotides, acyclonucleotides and the like and sterically hindered molecules, such as fluorescent molecules and the like. When nucleotide modifiers are used, they replace ribonucleotides in the dsRNA such that the length of the dsRNA does not change. In another embodiment, the dsRNA has an overhang on the 3' end of the sense strand and the antisense strand is modified for Dicer processing. In one embodiment, the antisense strand has a 5' phosphate. The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are adjacent to the 3' end of antisense strand and are sufficiently complementary to a nucleotide sequence of the RNA produced from the target gene. Further in accordance with this embodiment, the dsRNA, i.e., the precursor RNAi molecule, may also have one or more of the following additional properties: (a) the antisense strand has a left shift from the typical 21-mer (i.e., the antisense strand includes nucleotides on the left side of the molecule when compared to the typical 21-mer) and (b) the strands may not be completely complementary, i.e., the strands may contain simple mismatch pairings.

The present invention provides a precursor RNAi molecule capable of mediating the expression of a respiratory virus-specific mRNA to which it corresponds. The precursor RNAi molecule contains a first oligonucleotide strand that is 22-30 nucleotides in length; and a second oligonucleotide strand that is 22-30 nucleotides in length, and has a nucleotide sequence that is sufficiently complementary to a sequence of an RNA of the target gene to direct target-specific RNAi, wherein the second oligonucleotide strand anneals to the first oligonucleotide strand under biological conditions, wherein at least one of the first and second oligonucleotide strands is modified on the 3' end to direct Dicer processing of the RNAi molecule and wherein the RNAi molecule, is a substrate for a Dicer.

In one embodiment, the present invention provides a precursor RNAi molecule capable of mediating the expression of a respiratory virus-specific mRNA to which the precursor RNAi molecule corresponds, following cleavage by Dicer having a first oligonucleotide strand that is 22-30 nucleotides in length; and a second oligonucleotide strand that is 22-30 nucleotides in length, and has a nucleotide sequence that is sufficiently complementary to a sequence of an RNA of the target gene to direct target-specific RNAi and wherein the second oligonucleotide strand anneals to the first oligonucleotide strand under biological conditions, wherein the first and second oligonucleotide strands have a different length, wherein one of the first and second oligonucleotide strands has a 3' overhang that enhances Dicer processing of the precursor RNAi molecule, and wherein the precursor RNAi is a substrate for a Dicer.

The precursor RNAi molecules described above may be specific for a respiratory syncytial virus (RSV). In particular, the target gene for the RNAi molecule may be an RSV A2 strain NS1, P, N or L gene. Alternatively, the RNAi molecule may be specific for an Influenza A virus, or may be specific for a Coronavirus. Exemplary Coronavirus sequences are provided in FIG. 3.

In one embodiment, the present invention provides a precursor RNAi molecule is capable of mediating the expression of an RSV-specific mRNA to which it corresponds having a first oligonucleotide strand that is 22-30 nucleotides in length; and a second oligonucleotide strand that is 22-30 nucleotides in length and has a nucleotide sequence that is sufficiently complementary to a sequence of an RNA of the target gene to direct target-specific RNAi; wherein the second oligonucleotide strand anneals to the first oligonucleotide strand under biological conditions; wherein the first strand of RNA comprises SEQ ID NO:279 and the second strand of RNA comprises SEQ ID NO:280, wherein the first strand of RNA comprises SEQ ID NO:283 and the second strand of RNA comprises SEQ ID NO:284, or wherein the first strand of RNA comprises SEQ ID NO:296 and the second strand of RNA comprises SEQ ID NO:297; and wherein the RNAi molecule is a substrate for a Dicer.

In another embodiment, the present invention provides a precursor RNAi molecule capable of mediating the expression of an Influenza A-specific mRNA to which it corresponds having a first oligonucleotide strand that is 22-30 nucleotides in length; and a second oligonucleotide strand that is 22-30 nucleotides in length and has a nucleotide sequence that is sufficiently complementary to a sequence of an RNA of the target gene to direct target-specific RNAi; wherein the second oligonucleotide strand anneals to the first oligonucleotide strand under biological conditions, wherein the first strand of RNA comprises SEQ ID NO:304, SEQ ID NO:305, SEQ ID NO:306, SEQ ID NO:307, SEQ ID NO:308, SEQ ID NO:309, SEQ ID NO:310, or SEQ ID NO:312; and wherein the RNAi molecule is a substrate for a Dicer.

In certain embodiments, the present invention provides a precursor RNAi molecule capable of mediating the expression of a Coronavirus virus-specific mRNA to which it corresponds having a first oligonucleotide strand that is 15-30 nucleotides in length; and a second oligonucleotide strand that is 15-30 nucleotides in length and has a nucleotide sequence that is sufficiently complementary to a sequence of an RNA of the target gene to direct target-specific RNAi and wherein the second oligonucleotide strand anneals to the first oligonucleotide strand under biological conditions; wherein the RNAi molecule mediates RNA interference of a Coronavirus virus-specific mRNA to which it corresponds. In one embodiment, the precursor RNAi molecule targets the gene that encodes angiotensin converting enzyme 2 (ACE2). Exemplary ACE2 sequences are provided in FIG. 17.

The present invention also provides a precursor RNAi molecule capable of mediating the expression of a mRNA for a gene product that contributes to inflammation in a mammal to which it corresponds having a first oligonucleotide strand that is 15-30 nucleotides in length; and a second oligonucleotide strand that is 15-30 nucleotides in length and has a nucleotide sequence that is sufficiently complementary to a sequence of an RNA of the target gene to direct target-specific RNAi; wherein the second oligonucleotide strand anneals to the first oligonucleotide strand under biological conditions; and wherein the RNAi molecule mediates RNA interference of the mRNA for the gene product that contributes to inflammation in a mammal. In one embodiment, the target gene is IL-8. Exemplary IL-8 sequences are provided in FIG. 14A.

In certain embodiments, the first oligonucleotide strand and the second oligonucleotide strand of the precursor RNAi molecules anneal to form a duplex that is 27 base pairs in length. Alternatively, they may anneal to a duplex that is between 21 to 23 base pairs in length. In certain embodiments, at least one of the first and second oligonucleotide strands is modified on the 3' end to direct Dicer processing of the RNAi molecule. In certain embodiments, the first and second oligonucleotide strands have different lengths and wherein one of the first and second oligonucleotide strands has a 3' overhang that enhances Dicer processing of the precursor RNAi molecule, such as a one to three nucleotide-long overhang (e.g., two nucleotides).

In certain embodiments, at least one of the first and second oligonucleotide strands of the precursor RNAi molecule is modified on the 3' end to direct Dicer processing of the RNAi molecule. Exemplary modifications include deoxyribonucleotides, dideoxyribonucleotides, acyclonucleotides, 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T), a monophosphate nucleotide of 3'-azido-3'-deoxythymidine (AZT), 2',3'-dideoxy-3'-thiacytidine (3TC), an a monophosphate nucleotide of 2',3'-didehydro-2',3'-dideoxythymidine (d4T). In certain embodiments, the modification is 1-3 deoxynucleotides substituted for ribonucleotides at the 3' end of the first oligonucleotide strand.

In certain embodiments, the first and second oligonucleotide strands of the precursor RNAi molecule are linked by a linker, wherein the strands anneal under biological conditions. The linker may be a chemical linker and/or an oligonucleotide.

In certain embodiments, a ribonucleotide of the first or second strand of the precursor RNAi molecule is modified, such as a ribonucleotide is substituted by a locked nucleic acid (LNA). The LNA may be in the 5' region of the first strand.

In certain embodiments, the first strand and the second strand are operably linked by means of an RNA loop strand to form a hairpin structure having a duplex structure and a loop structure. The loop strand in some embodiments contains from 4 to 10 nucleotides (e.g., 4, 5 or 6 nucleotides).

The target respiratory virus may be an RSV or a Coronavirus. For example, the Coronavirus may be Coronavirus 229E, OC43, NL63, or SARS CoV. As used herein, the term "specific for" refers to an RNA wherein in a 21 base pair region of the RNA, at least 20 of the nucleotides of one strand of the nucleic acid composition are identical to a corresponding respiratory viral mRNA. In one embodiment of the present invention, the RNA is a duplex of two molecules of RNA. In an alternative embodiment of the present invention, the RNA is a single strand of RNA, and forms a hairpin structure having a duplex structure and a loop structure (shRNAi). The present invention provides a composition of a polymer or excipient and the nucleic acid composition. It should further be noted that full complementarity between the target sequence and the antisense siRNA is not required. That is, the resultant antisense siRNA is sufficiently complementary with the target sequence. The sense strand is substantially complementary with the antisense strand to anneal to the antisense strand under biological conditions.

In one embodiment of the present invention, the antisense siRNA is modified to include 1-9 ribonucleotides on the 5' end to give a length of 22-28 nucleotides. When the antisense strand has a length of 21 nucleotides, then 1-7 ribonucleotides, or 2-5 ribonucleotides and or 4 ribonucleotides are added on the 3' end. The added ribonucleotides may have any sequence. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has 24-30 nucleotides. The sense strand is substantially complementary with the antisense strand to anneal to the antisense strand under biological conditions. In one embodiment, the antisense strand is synthesized to contain a modified 3' end to direct Dicer processing. In another embodiment, the sense strand of the dsRNA has a 3' overhang. In a further embodiment, the antisense strand is synthesized to contain a modified 3' end for Dicer binding and processing and the sense strand of the dsRNA has a 3' overhang.

The present invention provides an expression cassette containing a nucleic acid encoding at least one strand of the precursor RNAi molecule described above. The expression cassette may further contain a promoter, such as regulatable promoter or a constitutive promoter. In certain embodiments the promoter may be a CMV, RSV, pol II or pol III promoter. In certain embodiments, the expression cassette further contains a polyadenylation signal, such as a synthetic minimal polyadenylation signal. In certain embodiments, the expression cassette further contains a marker gene. The present invention also provides a cell containing the expression cassette. Such a cell may be a mammalian cell. The present invention further provides a non-human mammal containing the expression cassette.

The present invention also provides a vector containing the expression cassette described above. The vector, in some embodiments, may contain two expression cassettes: a first expression cassette having a nucleic acid encoding the first strand of the RNA duplex, and a second expression cassette having a nucleic acid encoding the second strand of the RNA duplex. The present invention further provides a vector containing an expression cassette having (1) a nucleic acid sequence encoding a first portion of RNA, (2) a second portion of RNA located immediately 3' of the first portion of RNA, and (3) a third portion of RNA located immediately 3' of the second portion of RNA, wherein the first and third portions of RNA are each less than 30 nucleotides in length and each more than 15 nucleotides in length, and wherein the sequence of the third portion of RNA is the complement of the sequence of the first portion of RNA to form an RNA duplex, and wherein the RNA duplex mediates RNA interference of a respiratory virus-specific messenger RNA (mRNA) to which it corresponds. The vectors described above may further contain a polyadenylation signal and/or a marker gene. The vector may be, in certain embodiments an adenoviral, lentiviral, adeno-associated viral (AAV), poliovirus, HSV, or murine Moloney-based viral vector. Alternatively, the vector may be a plasmid vector. The present invention provides a composition of a polymer or excipient and the vector.

The present invention provides a method of inducing RNA interference in an airway epithelia cell by contacting the airway epithelial cell with an agent, wherein the agent is (a) one or more of the precursor RNAi molecules described above, or (b) one or more vectors described above, wherein the agent mediates RNA interference of an mRNA to which it corresponds.

The present invention also provides a method of disrupting expression of a nucleic acid sequence that contributes to genesis or perpetuation of a pulmonary disease by administering an agent, wherein the agent is (a) one or more of the precursor RNAi molecules described above, or (b) one or more vectors described above, wherein the agent mediates RNA interference of an mRNA to which it corresponds.

The present invention provides a method of degrading mRNA involved in onset and perpetuation of inflammatory signaling in a respiratory epithelial cell by delivering to the epithelial cell an agent, wherein the agent is (a) one or more of the precursor RNAi molecules described above, or (b) one or more vectors described above, wherein the agent mediates RNA interference of an mRNA to which it corresponds.

The present invention provides a method of targeting the destruction of mRNA encoding proteins that stimulate inflammatory response in an airway epithelial cell comprising delivering to the airway epithelial cell an agent, wherein the agent is (a) one or more of the precursor RNAi molecules described above, or (b) one or more vectors described above, wherein the agent mediates RNA interference of an mRNA to which it corresponds. In certain embodiments, the proteins that stimulate inflammatory response are associated with pro-inflammatory processes, viral pathogens, and other agents involved in respiratory diseases. Examples of such respiratory diseases include asthma, COPD, cystic fibrosis, or interstitial lung disease.

In certain embodiments of the above methods, the mRNA is of a respiratory virus-specific mRNA. Examples of such respiratory viruses are RSV and Coronavirus (e.g., Coronavirus 229E, OC43, NL63, or SARS CoV).

In the above methods, the respiratory epithelial cell may be located in a patient in need of such treatment. The agents used in these methods may be delivered to nasal or intrapulmonary epithelia by direct topical application, aerosol, dry powder, electroporation, lipofection, or a polymer or excipient. The polymer or excipient may be a viscoelastic, bioadhesive, or mucoadhesive polymer or excipient. In certain embodiments, the polymer or excipient is a viscoelastic polymer or excipient, such as a methylcellulose, carboxymethylcellulose or a poloxamer polymer. In certain embodiments, the agent further contains a calcium chelator, such as ethylene glycol-bis -(2-aminoethyl)-N,N,N', N'-tetraacetic acid (EGTA), ethylenedioxy-diethylene-dinitrilo -tetraacetic acid (EDTA) or 1,2-bis(aminophenoxy)ethane-N,N,N', N'-tetra-acetic acid (BAPTA).

The present invention further provides compositions of containing a polymer or excipient viscoelastic gel and a precursor RNAi molecule or vector described above. The polymer or excipient may be bioadhesive, mucoadhesive or viscoelastic. In certain embodiments, the polymer or excipient is a gel. In certain embodiments, the gel is a viscoelastic gel. Examples of viscoelastic gels are methylcellulose, carboxymethylcellulose or a poloaxamer polymer. In the present invention, the composition may further contain a calcium chelator. Examples of suitable calcium chelators are ethylene glycol-bis-(2-aminoethyl)-N,N,N', N'-tetraacetic acid (EGTA), ethylenedioxy-diethylene-dinitrilo-tetraacetic acid (EDTA) and 1,2-bis(aminophenoxy)ethane-N,N,N', N'-tetra-acetic acid (BAPTA).

In another aspect, the present invention provides pharmaceutical compositions containing the disclosed dsRNA compositions.

The present invention also provides methods for selectively reducing the expression of a gene product from a desired target gene in a cell, as well as for treating diseases caused by the expression of the gene. In one embodiment, the method involves introducing into the environment of a cell an amount of a dsRNA of the present invention such that a sufficient portion of the dsRNA can enter the cytoplasm of the cell to cause a reduction in the expression of the target gene.

The compositions and methods have an unanticipated level of potency of the RNAi effect. Although the invention is not intended to be limited by the underlying theory on which it is believed to operate, it is thought that this level of potency and duration of action are caused by the fact the dsRNA serves as a substrate for Dicer, which appears to facilitate incorporation of one sequence from the dsRNA into the RISC complex that is directly responsible for destruction of the RNA from the target gene.

BRIEF DESCRIPTION OF THE FIGURES

This patent or application file contains at least one drawing executed in color. Copies of this patent or patent application publication with color drawing(s) will be provided by the Office upon request and payment of the necessary fee.

FIG. 4. Specific RNAi oligonucleotides were designed against Respiratory Syncytial Virus A2 strain, N (nucteocapsid) gene; L (long polymerase) gene, and P (phosphoprotein) gene (SEQ ID NOS 166-198).

FIG. 5. Specific RNAi oligonucleotides were designed against Coronavirus 229E genes (L: 5 leader sequence; NP: nucleocapsid protein; P: polymerase), (SEQ ID NOS 199-246 are shown with SEQ ID NO: 9 as T7), and SEQ ID NOS: 203-246 correspond to the listed antisense sequences.

FIG. 6. Gene transfer to the airway epithelium of mice with an adenoviral vector expressing firefly luciferase is enhanced by gel formulations. The vector was formulated with 1% methylcellulose (MC), 400 mM EGTA, or no excipient. Control animals received no vector. Five days later in vivo luminescence was measured by giving mice an intraperitoneal dose of luciferin and capturing photons released with a CCD camera in a light tight box (Xenogen system).

FIG. 10. 27-mer siRNA oligonucleotide knockdown of P, N, and L genes inhibit RSV A2 strain infection.

FIG. 13. Viscoelastic gel formulation of siRNA oligonucleotides facilitates delivery to respiratory epithelia in vivo. Cy3 labeled siRNA oligonucleotides were formulated with 1% methylcellulose gel and directly instilled into the trachea of Balb/c mice in a volume of 50 microliters/mouse. Four hours later the animals were killed and frozen sections of lung tissue examined by fluorescent microscopy. The animals receiving the gel formulated siRNA (left panel) had marked fluorescent signal in pulmonary epithelia. A control lung (untreated) is shown in right panel demonstrates low level background autofluorescence.

FIG. 14. Design of 27-mer siRNA oligonucleotides against viral and human genes. FIG. 14A provides the DNA sequence for human interteukin-8 (IL-8, SEQ ID NO: 247) and the 27-mer oligonucleotides targeting the sequence (SEQ ID NOS 248-256). Highlighted in bold are three regions targeted by 27-mer siRNA oligonucleotides (SEQ ID NOS 257-303). The double stranded oligonucleotides are indicated by #193, #717, and #880.

FIG. 16 provides shRNA oligonucleotides designed against human angiotensin converting enzyme 2 (ACE2), (SEQ ID NOS 322-331 are shown with SEQ ID NO:166 as the termination sequence, SEQ ID NO:174 as the loop sequence, and SEQ ID NO: 182 as the 23 nt mU6 sequence).

FIG. 17 shows the efficacy of RSV shRNAs in an in vitro assay using a plasmid that has a fusion transcript of the RSV N gene with renilla luciferase and measures luciferase as an indirect assay for knock down. shRen=positive control; shRen.mis=misdirected (negative control); SHAG=negative control; and N-X hairpin for screening. (n=4 replicates).

FIG. 20.

DETAILED DESCRIPTION OF THE INVENTION

I. RNA Interference (RNAi) of Airway Epithelial Cells
  A. RNA Interference (RNAi)

Figure 1:
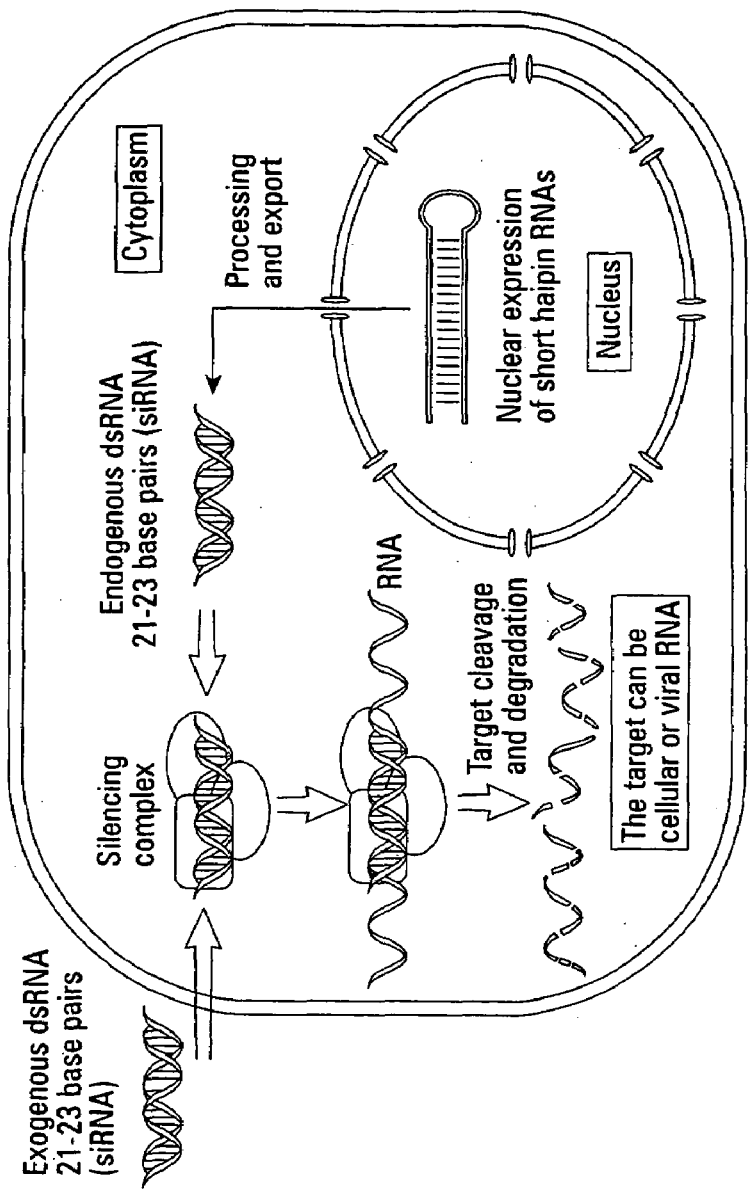
FIG. 1. A model for the mechanism of RNA interferences. (Carmichael et al., 2002).

Eukaryotic cells possess the capacity to respond to inhibition of gene expression by RNAi (FIG. 1). It has been demonstrated that dsRNA introduced into *Drosophila* cell lysates was degraded into 21-23 nucleotide long fragments with 3-prime overhangs. Subsequently, Tuschl and colleagues transfected small inhibitory (siRNAs; microRNAs; miRNA) into HEK293, NIH 3T3, COS-7, or HeLa cells, and found specific inhibition of gene expression. When dsRNA of greater than 50 and 500 bp were tested, both specific and nonspecific silencing was observed. They found specific siRNA interference with 9 out of 10 constructs tested, with inhibitory effects at concentrations well below that required for antisense oligonucleotides. There is now extensive evidence for the functional application of RNAi to modulate gene expression in mammalian cells. Recent work using dsRNA oligonucleotides or plasmid-based vectors also demonstrate the potential to target viral mRNAs including hepatitis B, HIV, respiratory syncytial virus, and influenzae A.

RNA interference is now established as an important biological strategy for gene silencing, but its application to mammalian cells has been limited by nonspecific inhibitory effects of long double-stranded RNA on translation. In one embodiment, in order to accomplish intracellular expression of the therapeutic siRNA, an RNA molecule is constructed containing a hairpin sequence (such as a 21-bp hairpin) representing sequences directed against the gene of interest. The siRNA, or a DNA sequence encoding the siRNA, is introduced to the target cell. The siRNA reduces target mRNA and gene protein expression.

In one embodiment of the present invention, the construct encoding the therapeutic siRNA is configured such that the hairpin is immediately contiguous to a promoter. The promoter used in a particular construct is selected from readily available promoters known in the art, depending on whether regulatable, inducible, tissue or cell-specific expression of the siRNA is desired. The construct is introduced into the target cell, such as by injection, allowing for diminished target-gene expression in the cell.

The present invention is directed to compositions that contain double stranded RNA ("dsRNA"), and methods for preparing them, that are capable of reducing the expression of target genes in eukaryotic cells. One of the strands of the dsRNA contains a region of nucleotide sequence that has a length that ranges from about 19 to about 30 nucleotides that can direct the destruction of the RNA transcribed from the target gene.

The phrase "duplex region" refers to the region in two complementary or substantially complementary oligonucleotides that form base pairs with one another, either by Watson-Crick base pairing or any other manner that allows for a duplex between oligonucleotide strands that are complementary or substantially complementary. For example, an oligonucleotide strand having 21 nucleotide units can base pair with another oligonucleotide of 21 nucleotide units, yet only 19 bases on each strand are complementary or substantially complementary, such that the "duplex region" consists of 19 base pairs. The remaining base pairs may, for example, exist as 5' and 3' overhangs. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well know in the art. Alternatively, two strands can be synthesized and added together under biological conditions to determine if they anneal to one another.

As used herein, an siRNA having a sequence "sufficiently complementary" to a target mRNA sequence means that the siRNA has a sequence sufficient to trigger the destruction of the target mRNA by the RNAi machinery (e.g., the RISC complex) or process. The siRNA molecule can be designed such that every residue of the antisense strand is complementary to a residue in the target molecule. Alternatively, substitutions can be made within the molecule to increase stability and/or enhance processing activity of said molecule. Substitutions can be made within the strand or can be made to residues at the ends of the strand.

In one embodiment of the first aspect of the present invention, the dsRNA, i.e., the precursor RNAi molecule, has a length sufficient such that it is processed by Dicer to produce an siRNA. According to this embodiment, a suitable dsRNA contains one oligonucleotide sequence, a first sequence that is at least 25 nucleotides in length and no longer than about 30 nucleotides. This sequence of RNA can be between about 26 and 29 nucleotides in length. This sequence can be about 27 or 28 nucleotides in length or 27 nucleotides in length. The second sequence of the dsRNA can be any sequence that anneals to the first sequence under biological conditions, such as within the cytoplasm of a eukaryotic cell. Generally, the second oligonucleotide sequence will have at least 19 complementary base pairs with the first oligonucleotide sequence, more typically the second oligonucleotides sequence will have about 21 or more complementary base pairs, or about 25 or more complementary base pairs with the first oligonucleotide sequence. In one embodiment, the second sequence is the same length as the first sequence, and the dsRNA is blunt ended. In another embodiment, the ends of the dsRNA have overhangs.

In certain aspects of this first embodiment, the first and second oligonucleotide sequences of the dsRNA exist on separate oligonucleotide strands that can be and typically are chemically synthesized. In some embodiments, both strands are between 26 and 30 nucleotides in length. In other embodiments, both strands are between 25 and 30 nucleotides in length. In one embodiment, both strands are 27 nucleotides in length, are completely complementary and have blunt ends. The dsRNA can be from a single RNA oligonucleotide that undergoes intramolecular annealing or, more typically, the first and second sequences exist on separate RNA oligonucleotides. In one embodiment, one or both oligonucleotide strands are capable of serving as a substrate for Dicer. In other embodiments, at least one modification is present that promotes Dicer to bind to the double-stranded RNA structure in an orientation that maximizes 12 the double-stranded RNA structure's effectiveness in inhibiting gene expression. The dsRNA can contain one or more deoxyribonucleic acid (DNA) base substitutions.

Suitable dsRNA compositions that contain two separate oligonucleotides can be chemically linked outside their annealing region by chemical linking groups. Many suitable chemical linking groups are known in the art and can be used. Suitable groups will not block Dicer activity on the dsRNA and will not interfere with the directed destruction of the RNA transcribed from the target gene. Alternatively, the two separate oligonucleotides can be linked by a third oligonucleotide such that a hairpin structure is produced upon annealing of the two oligonucleotides making up the dsRNA composition. The hairpin structure will not block Dicer activity on the dsRNA and will not interfere with the directed destruction of the RNA transcribed from the target gene.

The first and second oligonucleotides are not required to be completely complementary. In fact, in one embodiment, the 3'-terminus of the sense strand contains one or more mismatches. In one aspect, about two mismatches are incorporated at the 3'-terminus of the sense strand. In another embodiment, the dsRNA of the invention is a double stranded RNA molecule containing two RNA oligonucleotides each of which is 27 nucleotides in length and, when annealed to each other, have blunt ends and a two nucleotide mismatch on the 3'-terminus of the sense strand (the 5'-terminus of the antisense strand). The use of mismatches or decreased thermodynamic stability (specifically at the 3'-sense/5'-antisense position) has been proposed to facilitate or favor entry of the antisense strand into RISC (Schwarz et al., 2003; Khvorova et al., 2003), presumably by affecting some rate-limiting unwinding steps that occur with entry of the siRNA into RISC. Thus, terminal base composition has been included in design algorithms for selecting active 21-mer siRNA duplexes (Ui-Tei et al., 2004; Reynolds et al., 2004). With Dicer cleavage of the dsRNA of this embodiment, the small end-terminal sequence which contains the mismatches will either be left unpaired with the antisense strand (become part of a 3' overhang) or be cleaved entirely off the final 21-mer siRNA. These "mismatches", therefore, do not persist as mismatches in the final RNA component of RISC. It was surprising to find that base mismatches or destabilization of segments at the 3' end of the sense strand of Dicer substrate improved the potency of synthetic duplexes in RNAi, presumably by facilitating processing by Dicer.

In one embodiment, the therapeutic siRNA acts as a dsRNA precursor RNAi molecule with several properties which enhance its processing by Dicer. According to this embodiment, the dsRNA has at least the following properties: (i) the dsRNA has a length sufficient such that it is processed by Dicer to produce an siRNA and at least one of the following properties: (ii) the dsRNA is asymmetric, e.g., has a 3' overhang on the antisense strand and (iii) the dsRNA has a modified 3' end on the sense strand to direct orientation of Dicer binding and processing of the dsRNA to an active siRNA. According to this embodiment, the sense strand comprises 22-28 nucleotides and the antisense strand comprises 24-30 nucleotides. In one embodiment, the dsRNA has an overhang on the 3' end of the antisense strand. In another embodiment, the sense strand is modified for Dicer binding and processing by suitable modifiers located at the 3' end of the sense strand. Suitable modifiers include deoxyribonucleotides, acyclonucleotides, sterically hindered molecules, such as fluorescent molecules and the like. When nucleotide modifiers are used, they replace ribonucleotides in the dsRNA such that the length of the dsRNA does not change. In another embodiment, the dsRNA has an overhang on the 3' end of the antisense strand and the sense strand is modified for Dicer processing. In another embodiment, the 5' end of the sense strand has a phosphate. The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are in the 21-nucleotide region adjacent to the 3' end of the antisense strand and are sufficiently complementary to a nucleotide sequence of the RNA produced from the target gene. Further in accordance with this embodiment, the dsRNA, i.e., the precursor RNAi molecule, may also have one or more of the following additional properties: (a) the antisense strand has a right shift from the typical 21 mer (i.e., the antisense strand includes nucleotides on the right side of the molecule when compared to the typical 21-mer), (b) the strands may not be completely complementary, i.e., the strands may contain simple mismatch pairings and (c) base modification, such as locked nucleic acid(s) may be included in the 5' end of the sense strand.

It has been found empirically that these longer dsRNA species of from 25 to about 30 nucleotides give unexpectedly effective results in terms of potency and duration of action. Without wishing to be bound by the underlying theory of the invention, it is thought that the longer dsRNA species serve as a substrate for the enzyme Dicer in the cytoplasm of a cell. In addition to cleaving the dsRNA of the invention into shorter segments, Dicer is thought to facilitate the incorporation of a single-stranded cleavage product derived from the cleaved dsRNA into the RISC complex that is responsible for the destruction of the cytoplasmic RNA derived from the target gene. The studies described herein have shown that the cleavability of a dsRNA species by Dicer corresponds with increased potency and duration of action of the dsRNA species.

In one embodiment of the present invention, the dsRNA, i.e., the precursor RNAi molecule, has several properties that enhance its processing by Dicer. According to this embodiment, the dsRNA has a length sufficient such that it is processed by Dicer to produce an active siRNA and at least one of the following properties: (i) the dsRNA is asymmetric, e.g., has a 3' overhang on the antisense strand and (ii) the dsRNA has a modified 3' end on the sense strand to direct orientation of Dicer binding and processing of the dsRNA to an active siRNA. According to this embodiment, the longest strand in the dsRNA comprises 24-30 nucleotides. In one embodiment, the dsRNA is asymmetric such that the sense strand comprises 22-28 nucleotides and the antisense strand comprises 24-30 nucleotides. Thus, the resulting dsRNA has an overhang on the 3' end of the antisense strand. The overhang is one to three nucleotides, for example two nucleotides. The sense strand may also have a 5' phosphate.

In another embodiment, the sense strand is modified for Dicer processing by suitable modifiers located at the 3' end of the sense strand, i.e., the dsRNA is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotides modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxynucleotides are used as the modifiers. When nucleotide modifiers are utilized, one to three nucleotide modifiers, or two nucleotide modifiers are substituted for the ribonucleotides on the 3' end of the sense strand. When sterically hindered molecules are utilized, they are attached to the ribonucleotide at the 3' end of the antisense strand. Thus, the length of the strand does not change with the incorporation of the modifiers. In another embodiment, the invention contemplates substituting two DNA bases in the dsRNA to direct the orientation of Dicer processing of the antisense strand. In a further embodiment of the present invention, two terminal DNA bases are substituted for two ribonucleotides on the 3' end of the sense strand forming a blunt end of the duplex on the 3' end of the sense strand and the 5' end of the antisense strand, and a two-nucleotide RNA overhang is located on the 3' end of the antisense strand. This is an asymmetric composition with DNA on the blunt end and RNA bases on the overhanging end.

The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are in the 21-nucleotide region adjacent to the 3' end of the antisense strand and are sufficiently complementary to a nucleotide sequence of the RNA produced from the target gene.

The first and second oligonucleotides are not required to be completely complementary. They only need to be substantially complementary to anneal under biological conditions and to provide a substrate for Dicer that produces an siRNA sufficiently complementary to the target sequence. Locked nucleic acids (LNAs), are well known to a skilled artisan (Elman et al., 2005; Kurreck et al., 2002; Crinelli et al., 2002; Braasch and Corey, 2001; Bondensgaard et al., 2000; Wahlestedt et al., 2000). In one embodiment, an LNA is incorporated at the 5' terminus of the sense strand. In another embodiment, an LNA is incorporated at the 5' terminus of the sense strand in duplexes designed to include a 3' overhang on the antisense strand.

In one embodiment, the dsRNA has an asymmetric structure, with the sense strand having a 25-base pair length, and the antisense strand having a 27-base pair length with a two base 3' overhang. In another embodiment, this dsRNA having an asymmetric structure further contains two deoxynucleotides at the 3' end of the sense strand in place of two of the ribonucleotides.

Suitable dsRNA compositions that contain two separate oligonucleotides can be linked by a third structure. The third structure will not block Dicer activity on the dsRNA and will not interfere with the directed destruction of the RNA transcribed from the target gene. In one embodiment, the third structure may be a chemical linking group. Many suitable chemical linking groups are known in the art and can be used. Alternatively, the third structure may be an oligonucleotide that links the two oligonucleotides of the dsRNA is a manner such that a hairpin structure is produced upon annealing of the two oligonucleotides making up the dsRNA composition. The hairpin structure will not block Dicer activity on the dsRNA and will not interfere with the directed destruction of the RNA transcribed from the target gene.

In another embodiment of the first aspect of the present invention, the dsRNA, i.e., the precursor RNAi molecule, has several properties that enhance its processing by Dicer. According to this embodiment, the dsRNA has a length sufficient such that it is processed by Dicer to produce an siRNA and at least one of the following properties: (i) the dsRNA is asymmetric, e.g., has a 3' overhang on the sense strand and (ii) the dsRNA has a modified 3' end on the antisense strand to direct orientation of Dicer binding and processing of the dsRNA to an active siRNA. According to this embodiment, the longest strand in the dsRNA comprises 24-30 nucleotides. In one embodiment, the sense strand comprises 24-30 nucleotides and the antisense strand comprises 22-28 nucleotides. Thus, the resulting dsRNA has an overhang on the 3' end of the sense strand. The overhang is one to three nucleotides, such as two nucleotides. The antisense strand may also have a 5' phosphate.

In another embodiment, the antisense strand is modified for Dicer processing by suitable modifiers located at the 3' end of the antisense strand, i.e., the dsRNA is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxynucleotides are used as the modifiers. When nucleotide modifiers are utilized, one to three nucleotide modifiers, or two nucleotide modifiers are substituted for the ribonucleotides on the 3' end of the antisense strand. When sterically hindered molecules are utilized, they are attached to the ribonucleotide at the 3' end of the antisense strand. Thus, the length of the strand does not change with the incorporation of the modifiers. In another embodiment, the invention contemplates substituting two DNA bases in the dsRNA to direct the orientation of Dicer processing. In a further invention, two terminal DNA bases are located on the 3' end of the antisense strand in place of two ribonucleotides forming a blunt end of the duplex on the 5' end of the sense strand and the 3' end of the antisense strand, and a two-nucleotide RNA overhang is located on the 3' end of the sense strand. This is an asymmetric composition with DNA on the blunt end and RNA bases on the overhanging end.

The present invention provides, in certain embodiments, a viral or plasmid vector containing an expression cassette, wherein the expression cassette comprises an isolated nucleic acid sequence encoding a small interfering RNA molecule (siRNA) targeted against a gene of interest. The siRNA may form hairpin structure comprising a duplex structure and a loop structure. The loop structure may contain from 4 to 10 nucleotides, such as 4, 5 or 6 nucleotides. The duplex is less than 30 nucleotides in length, such as from 19 to 27 nucleotides. The siRNA may further comprise an overhang region. Such an overhang may be a 3' overhang region or a 5' overhang region. The overhang region may be, for example, from 1 to 6 nucleotides in length. The expression cassette may further comprise a promoter. Examples of promoters include regulatable promoters and constitutive promoters. For example, the promoter may be a CMV or RSV promoter. The expression cassette may further comprise a polyadenylation signal, such as a synthetic minimal polyadenylation signal. Other promoters, including pol II and pol III promoters, may be used. The nucleic acid sequence may further comprise a marker gene. The viral vector of the present invention may be an adenoviral, lentiviral, adeno-associated viral (AAV), poliovirus, herpes simplex virus (HSV) or murine Moloney-based viral vector. The gene of interest may be a gene associated with a condition amenable to siRNA therapy. Examples of such conditions include asthma, cystic fibrosis, or interstitial lung disease.

The present invention also provides a viral or plasmid vector comprising an expression cassette, wherein the expression cassette comprises a promoter operably-linked to an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment, and wherein the isolated nucleic acid sequence functions as a small interfering RNA molecule (siRNA) targeted against a gene of interest.

The present invention provides a method of reducing the expression of a gene product in a cell by contacting a cell with a viral or plasmid vector described above. It also provides a method of treating a patient by administering to the patient a composition comprising a viral or plasmid vector described above.

The present invention further provides a method of reducing the expression of a gene product in a cell, comprising contacting a cell with viral or plasmid vector comprising an expression cassette, wherein the expression cassette comprises a promoter operably-linked to an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment, and wherein the isolated nucleic acid sequence functions as a small interfering RNA molecule (siRNA) targeted against a gene of interest.

In another aspect, the present invention provides for a pharmaceutical composition comprising the dsRNA of the present invention. The dsRNA sample can be suitably formulated and introduced into the environment of the cell by any means that allows for a sufficient portion of the sample to enter the cell to induce gene silencing, if it is to occur. Many formulations for dsRNA are known in the art and can be used so long as dsRNA gains entry to the target cells so that it can act. See, e.g., U.S. published patent application Nos. 2004/0203145 A1 and 2005/0054598 A1, each incorporated herein by reference. For example, dsRNA can be formulated in buffer solutions such as phosphate buffered saline solutions, liposomes, micellar structures, and capsids. Formulations of dsRNA with cationic lipids can be used to facilitate transfection of the dsRNA into cells. For example, cationic lipids, such as lipofectin (U.S. Pat. No. 5,705,188, incorporated herein by reference), cationic glycerol derivatives, and polycationic molecules, such as polylysine (published PCT International Application WO 97/30731, incorporated herein by reference), can be used. Suitable lipids include Oligofectamine, Lipofectamine (Life Technologies), NC388 (Ribozyme Pharmaceuticals, Inc., Boulder, Co.), or FuGene 6 (Roche) all of which can be used according to the manufacturer's instructions.

The present method also provides a method of treating a patient, comprising administering to the patient a composition comprising a viral or plasmid vector, wherein the viral vector comprises an expression cassette, wherein the expression cassette comprises a promoter operably-linked to an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment, and wherein the isolated nucleic acid sequence functions as a small interfering RNA molecule (siRNA) targeted against a gene of interest.

Suitable amounts of dsRNA must be introduced and these amounts can be empirically determined using standard methods. Typically, effective concentrations of individual dsRNA species in the environment of a cell will be about 50 nanomolar or less 10 nanomolar or less, or compositions in which concentrations of about 1 nanomolar or less can be used. In other embodiment, methods utilize a concentration of about 200 picomolar or less and even a concentration of about 50 picomolar or less can be used in many circumstances.

B. Respiratory Diseases That Can Be Targeted By RNAi

The airway epithelium represents an important barrier between the host and the environment. It is a first site of contact with pathogens, particulates, and other stimuli, and has evolved the means to dynamically respond to these challenges. Thus, a number of human pulmonary diseases primarily involve the respiratory epithelium. Because of its intimate contact with the external environment, it is the first site of entry for many common respiratory viral and bacterial pathogens. It is also one of the first tissues to manifest disease in response to such exposures. In addition, it is a primary tissue affected in pulmonary diseases such as asthma, COPD and cystic fibrosis.

The present invention delivers RNAi molecules to the respiratory epithelium as a means to disrupt gene expression contributing to the genesis or perpetuation of several pulmonary diseases, such as viral infections, asthma, chronic obstructive pulmonary disease (COPD), cystic fibrosis, and inflammation from respiratory bacteria. For example, RNA viruses that replicate in the cytoplasm of the airway epithelium are targets. RNA viruses that replicate the cytoplasm of respiratory epithelial cells are particularly attractive targets for inhibition using RNAi technology. By specific targeting of the RNAs required for viral replication and assembly, it is possible to inhibit respiratory viruses. Exemplary respiratory virus targets for RNAi include the following:

Paramyxoviruses—Respiratory syncytial virus (RSV), Parainfluenzae virus, Measles virus, metapneumovirus
Orthomyxoviruses—Influenzae viruses
Coronaviruses—229E, OC43, SARS-CoV, NL63
Picornaviruses—Rhinovirus
Arenavirus—LCMV
Retrovirus—HIV
Bunyaviridae—Hantavirus
Filovirus—Ebola, Marburg As another example, many lung diseases have a component of inflammation as a common denominator in their disease pathogenesis (e.g., cystic fibrosis, asthma, COPD). RNAi provides a means to specifically target the degradation of mRNAs that are involved in the onset and perpetuation of inflammatory signaling in the airway epithelium and may thereby modify the disease state. In cystic fibrosis, production of interleukin 8 (IL-8) contributes to the influx of neutrophils in the airway and contributes to inflammation and lung destruction.

As a third example, asthma, a disease afflicting 5-10% of the population, is also characterized by airway inflammation. Targeting the destruction of mRNAs of proteins that stimulate inflammatory responses is another application of this invention. The signaling cascade mediated by the transcription factor nuclear factor kappa B (NF-kB) is central to a host of inflammatory processes in airway epithelia. Components of this signaling system, such as p50, p65, IKK-alpha, IKK-beta, and the upstream kinase TAK, IRAK and MyD88, all represent targets for degradation by RNAi.

C. Delivery of siRNA to Airway Epithelial Cells In Vitro And In Vivo

Application of siRNA has been accomplished by transfection-based systems using synthetic siRNAs and more recently using viral and non-viral vector systems. The present studies with recombinant DNA vectors and synthetic oligonucleotides expressing siRNA specific for eGFP and respiratory syncytial virus genes serve as a springboard for further analyses on the utility of siRNA respiratory viral infections. The delivery of RNAi to a specialized tissue such as the airway epithelium presents significant challenges. The inventors have determined that it is feasible to present RNAi to the airway epithelium by one of the following formats: in a viral vector (e.g., adenovirus or retrovirus), as a plasmid expressing a DNA hairpin, or as a dsRNA oligonucleotide with or without lipofection or electroporation to enhance uptake.

RNAi can be delivered to the airway epithelium by one of several techniques, such as by aerosol, bronchoscopic instillation, lipid complexation or in combination with polymers or excipients, or by electroporation. Polymers that can be used in the present invention include bioadhesive, mucoadhesive, and viscoelastic polymers or excipients. Suitable excipients in the case of liquid compositions include natural polymeric materials, such as sodium alginate, xanthan, gellan gum, welan, rhamsan, agar, carageenan, dextran sulphate, keratan, dermatan, pectin, hyaluronic acid and salts thereof. Natural polymers or gums include heparin, fucoidin, gelatin, gum acacia, tragacanth, zein and modified zein, keratin, chondroitin sulfate, proteoglycans, collagen, alginate/alginic acid, galactomannan, glucomannan, and chitosan (and salts thereof).

The polymer may also be a cellulosic. Examples of suitable cellulosics include modified polysaccharide materials such as carboxymethylcellulose calcium, carboxymethylcellulose sodium, ethylcellulose, hydroxyethylcellulose, hydroxypropylcellulose, hydroxypropylmethycellulose phthalate, and noncrystalline cellulose. Synthetically modified natural polymers include cellulose derivatives such as alkyl celluloses, hydroxyalkyl celluloses, cellulose ethers, cellulose esters, and nitrocelluloses. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt.

Other polymers that may be used in the present invention include polyvinylpyrrolidone, block copolymers containing one or more blocks made up of repeating ethylene oxide units (such as Poloxamer/Pluronic and Tetronic polymers), polyoxyethylene alkyl ethers, polyoxyethylene castor oil derivatives, polyoxyethylene sorbitan fatty acid esters, polyethylene glycols, polyoxyethylene stearates (PEGs). Other polymers that may be used as an excipient include PLA-PEG copolymers, which can be synthesized by the methods described in EP-A-0166596 or by the methods described by Deng et al. (1988), Zhu et al. (1989), Gref et al. (1994), or PCT/WO95/03357. Water soluble linear tri-block copolymers of PLA-PEG that gel when the temperature is raised may be used. Other polymers include polyacrylamides (Carbomers/Carbopol), polycarbophil, and pemulen.

The concentration of excipient material needed is dependent on the type of material used but is typically between 0.01% w/v and 50% w/v, by which is meant from 0.01 to 50 g of excipient per 100 mls of the liquid, e.g., water. In certain embodiments the concentration of the excipient material is in the range 0.1% w/v to 50% w/v, i.e. 0.1 to 50 g of excipient per 100 mls of the liquid. In certain embodiments the concentration of the excipient material is in the range 0.5% w/v to 50% w/v, such as in the range 1.0% W/V to 30% w/v. These materials are given as examples and the list is not to be taken as exhaustive.

It has recently been shown that electroporation can be effectively used in vivo as a means to assist in gene therapy, i.e., as a means for introducing naked DNA into an organ, such as a lung, in a living animal (U.S. Pat. No. 6,593,130).

In one embodiment, the RNAi construct can be aerosolized to enhance delivery to the lung. In another embodiment, bronchoscopy can be used to directly apply the RNAi to the epithelium.

D. Methods For Identifying Inhibitory Sequences To Target Viral Pathogens

There are a variety of strategies known in the field for designing therapeutic RNAi molecules for target mRNA degradation. These include computational approaches (web-based and proprietary, e.g., See Ambion website or GenScript), and following basic principles (Amarzguioui 2004; Reynolds 2004). However, not every candidate siRNA sequence will be capable of directing effective target gene silencing. In many cases, no freely available algorithm works any better than random selection for predicting the effectiveness of shRNA. Anecdotal evidence from our laboratories suggests that the ease that a target transcript is silenced can vary greatly depending upon the target mRNA or the context in which the target sequence is placed. As a result, the gene silencing capability of each shRNA must be tested empirically, and many candidates may have to be screened to identify one that effectively silences the gene of interest. Efficacy of a candidate RNAi is confirmed through a variety of assays including: 1) Northern blot, 2) quantitative RT-PCR, 3) immunofluorescence, 4) flurorescent detection of target proteins with GFP fusions (or other fluorophores), 5) western blot, 6) functional protein assays (e.g., beta-galactosidase assays).

E. Examples of Specific RNAi Molecules and Their Targets.

The following siRNA molecules were generated. For all siRNAs discussed below, the 5' nucleotide in the targeted cDNA sequence is referred to as position 1 and each subsequent nucleotide is numbered in ascending order from 5' to 3'.

Figure 3:
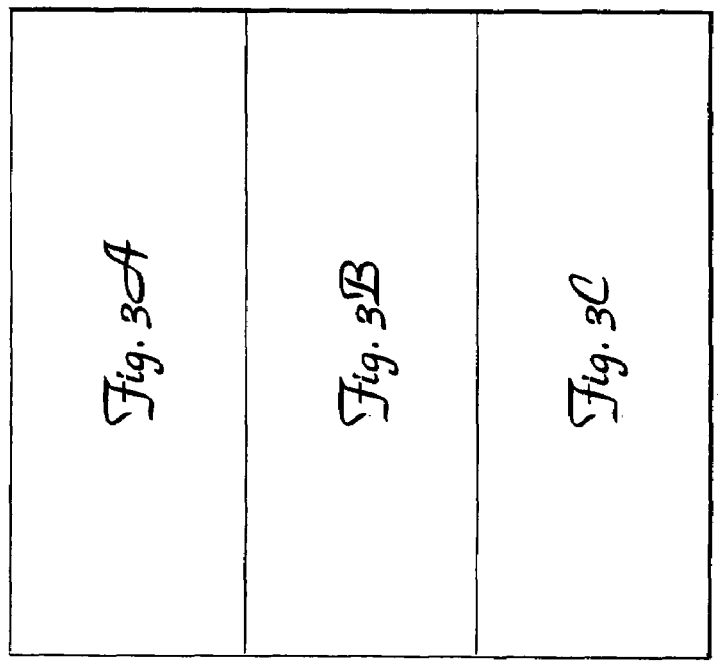
FIG. 3. Specific RNAi oligonucleotides were designed against the indicated genes and common sequences of the SARS Coronavirus (Urbani strain) (SEQ ID NOS 1-165). All sequences listed under the columns headed "T7" are SEQ ID NO: 9.

Specific RNAi oligonucleotides were designed against the SARS Coronavirus, as indicated in FIG. 3.

Specific short hairpin RNAi oligonucleotides were designed against Respiratory Syncytial Virus A2 strain, N (nucleoprotein) gene; L (polymerase) gene, as indicated in FIG. 4.

Specific short hairpin RNAi oligonucleotides were designed against Coronavirus 229E (L: leader sequence; NP: nucleocapsid protein; P: polymerase), as indicated in FIG. 5.

Specific 27-mer RNAi oligonucleotides were designed against human interleukin-8 gene, as indicated in FIG. 14A.

Figure 14B:
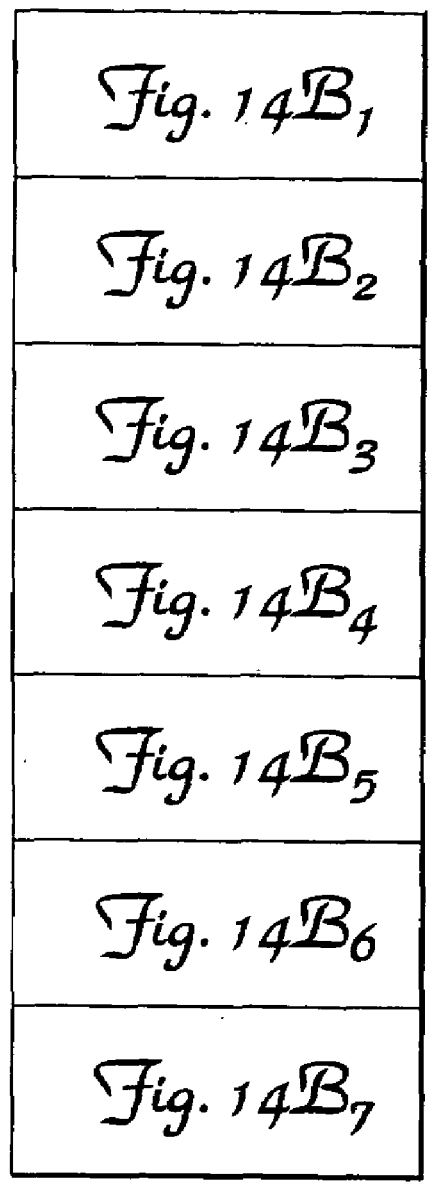
FIG. 14B provides the DNA sequences for RSV strain A2 and the 27-mer oligonucleotides targeting specific genes. The double stranded oligonucleotides targeting RSV genes NS1, N, P. and L are indicated at the end of each gene sequence FIG. 15 provides a table indicating shRNA sequences to influenza strain A/puerto rico/8/34, H1N1 (SEQ ID NOS 304-321 are shown with SEQ ID NO:166 as the termination sequence, SEQ ID NO: 174 as the ioop sequence, and SEQ ID NO:182 as the 23 nt mU6 sequence). The genes targeted are indicated.
Figure 18:
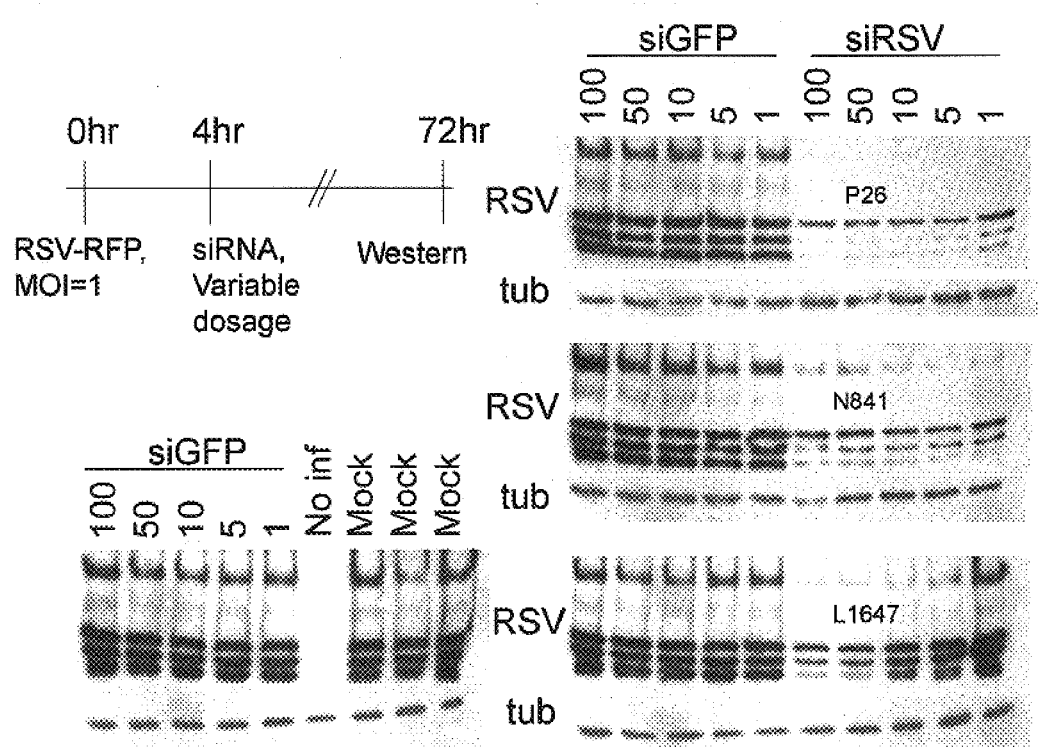

Specific 27-mer RNAi oligonucleotides were designed against RSV, A2 strain genes, as indicated in FIG. 14B.

Specific short hairpin RNAi oligonucleotides were designed against influenza A strain genes, as indicated in FIG. 15.

Specific short hairpin RNAi oligonucleotides were designed against human angiotensin converting enzyme 2 (ACE2) gene, as indicated in FIG. 16.

F. Methods for Enhancing Delivery of RNAi, shRNA to Pulmonary Epithelia.

Advances in gene transfer to the conducting airways for the treatment of pulmonary diseases such as cystic fibrosis and asthma have resulted in the identification of vectors which are capable of successful gene transfer to the airway epithelium both in vitro and in animal models. While most viral vector therapies show far superior efficacy to the non-viral systems under investigation, the efficiency of the current viral vector formulations is still far too low to provide effective treatment clinically in humans. One of the major limitations to efficient gene transfer in human airways is the rapid removal (<60 min.) of materials from the surface of the airways to the gastrointestinal tract via mucociliary clearance. This short time period does not allow gene transfer to take place in sufficient numbers of airway epithelial cells. The ability to transiently slow mucociliary clearance in order to provide a longer epithelial exposure time for the vector might improve the extent of gene transfer. Preliminary studies have shown that an adenovirus vector (Ad-betagal) has significantly improved gene transfer following formulation in a series of viscoelastic gels designed to slow mucociliary clearance. Surprisingly, several of the viscoelastic gels even showed the ability to target gene transfer to the conducting airways rather than the alveolar compartment, which is the desired treatment site for diseases such as cystic fibrosis and asthma.

One hurdle to the use of gene transfer approaches for the treatment of airway disease such as cystic fibrosis (CF) and asthma is the inefficient delivery achieved following mucosal administration. Several host defense mechanisms, including cellular barriers, immunologic responses, and mucociliary clearance act in concert to inhibit gene transfer. Preliminary experiments have demonstrated that targeted delivery to the conducting airways in the lung can be achieved using adenovirus vectors formulated in polymeric solutions (gels) designed to interact with the mucosal surface and delay mucociliary clearance. These results suggest that these formulation strategies, which may be applicable to several vector systems, dramatically improve gene transfer efficiency to the conducting airways.

II. Definitions

The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

The term "nucleotide sequence" refers to a polymer of DNA or RNA which can be single- stranded or double-stranded, optionally containing synthetic, non-natural or altered nucleotide bases capable of incorporation into DNA or RNA polymers.

The terms "nucleic acid," "nucleic acid molecule," or "polynucleotide" are used interchangeably and may also be used interchangeably with gene, cDNA, DNA and RNA encoded by a gene.

The invention encompasses isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include nonexpressed DNA segments that, for example, form recognition sequences for other proteins. "Genes" can be obtained from a variety of sources, including cloning from a source of interest or synthesizing from known or predicted sequence information, and may include sequences designed to have desired parameters.

"Naturally occurring" is used to describe a composition that can be found in nature as distinct from being artificially produced. For example, a nucleotide sequence present in an organism (including a virus), which can be isolated from a source in nature and which has not been intentionally modified by a person in the laboratory, is naturally occurring.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. It also may include sequences required for proper translation of the nucleotide sequence. The coding region usually codes for a protein of interest but may also code for a functional RNA of interest, for example an antisense RNA, a nontranslated RNA in the sense or antisense direction, or a siRNA. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of an regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Functional RNA" refers to sense RNA, antisense RNA, ribozyme RNA, siRNA, or other RNA that may not be translated but yet has an effect on at least one cellular process.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters. Examples of promoters that may be used in the present invention include CMV, RSV, polII and polIII promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

"Altered levels" refers to the level of expression in transgenic cells or organisms that differs from that of normal or untransformed cells or organisms.

"Antisense inhibition" refers to the production of antisense RNA transcripts capable of suppressing the expression of protein from an endogenous gene or a transgene.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm. Non-limiting examples of such mathematical algorithms are the algorithm of Myers and Miller (1988); the local homology algorithm of Smith et al. (1981); the homology alignment algorithm of Needleman and Wunsch (1970); the search-for-similarity-method of Pearson and Lipman (1988); the algorithm of Karlin and Altschul (1990), modified as in Karlin and Altschul (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988); Higgins et al. (1989); Corpet et al. (1988); Huang et al. (1992); and Pearson et al. (1994). The ALIGN program is based on the algorithm of Myers and Miller, supra. The BLAST programs of Altschul et al. (1990), are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by inspection.

For purposes of the present invention, comparison of nucleotide sequences for determination of percent sequence identity to the promoter sequences disclosed herein may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, 79%, 80%, 81%, 82%, 83%, 84%, 85%, 86%, 87%, 88%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, 80%, 90%, or even at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 93%, or 94%, or even 95%, 96%, 97%, 98% or 99%, sequence identity to the reference sequence over a specified comparison window. In certain embodiments, optimal alignment is conducted using the homology alignment algorithm of Needleman and Wunsch (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point (Tm) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the Tm; moderately stringent conditions can utilize a hybridization and/or wash at 6, 7, 8, 9, or 10° C. lower than the Tm; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), the SSC concentration is increased so that a higher temperature can be used. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. For short nucleotide sequences (e.g., about 10 to 50 nucleotides), stringent conditions typically involve salt concentrations of less than about 1.5 M, less than about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids that have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

"Gene silencing" refers to the suppression of gene expression, e.g., transgene, heterologous gene and/or endogenous gene expression. Gene silencing may be mediated through processes that affect transcription and/or through processes that affect post-transcriptional mechanisms. In some embodiments, gene silencing occurs when siRNA initiates the degradation of the mRNA of a gene of interest in a sequence-specific manner via RNA interference. In some embodiments, gene silencing may be allele-specific. "Allele-specific" gene silencing refers to the specific silencing of one allele of a gene.

"Knock-down" or "knock-down technology" refers to a technique of gene silencing in which the expression of a target gene is reduced as compared to the gene expression prior to the introduction of the siRNA, which can lead to the inhibition of production of the target gene product. The term "reduced" is used herein to indicate that the target gene expression is lowered by 1-100%. For example, the expression may be reduced by 10, 20, 30, 40, 50, 60, 70, 80, 90, 95, or even 99%. Knock-down of gene expression can be directed by the use of dsRNAs or siRNAs. For example, "RNA interference (RNAi)," which can involve the use of siRNA, has been successfully applied to knockdown the expression of specific genes in plants, *D. melanogaster, C. elegans*, trypanosomes, planaria, hydra, and several vertebrate species including the mouse and zebrafish.

"RNA interference (RNAi)" is the process of sequence-specific, posttranscriptional gene silencing initiated by siRNA. RNAi is seen in a number of organisms such as *Drosophila*, nematodes, fungi and plants, and is believed to be involved in anti-viral defense, modulation of transposon activity, and regulation of gene expression. During RNAi, siRNA induces degradation of target mRNA with consequent sequence-specific inhibition of gene expression.

A "small interfering" or "short interfering RNA" or "siRNA" is a RNA duplex of nucleotides that is targeted to a gene interest. A "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

In one embodiment, the therapeutic siRNA acts as a dsRNA precursor RNAi molecule with several properties which enhance its processing by Dicer. According to this embodiment, the dsRNA has at least the following properties: (i) the dsRNA has a length sufficient such that it is processed by Dicer to produce an siRNA and at least one of the following properties: (ii) the dsRNA is asymmetric, e.g., has a 3' overhang on the antisense strand and (iii) the dsRNA has a modified 3' end on the sense strand to direct orientation of Dicer binding and processing of the dsRNA to an active siRNA. According to this embodiment, the sense strand comprises 22-28 nucleotides and the antisense strand comprises 24-30 nucleotides. In one embodiment, the dsRNA has an overhang on the 3' end of the antisense strand. In another embodiment, the sense strand is modified for Dicer binding and processing by suitable modifiers located at the 3' end of the sense strand. Suitable modifiers include deoxyribonucleotides, acyclonucleotides, sterically hindered molecules, such as fluorescent molecules and the like. When nucleotide modifiers are used, they replace ribonucleotides in the dsRNA such that the length of the dsRNA does not change. In another embodiment, the dsRNA has an overhang on the 3' end of the antisense strand and the sense strand is modified for Dicer processing. In another embodiment, the 5' end of the sense strand has a phosphate. The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are in the 21-nucleotide region adjacent to the 3' end of the antisense strand and are sufficiently complementary to a nucleotide sequence of the RNA produced from the target gene. Further in accordance with this embodiment, the dsRNA, i.e., the precursor RNAi molecule, may also have one or more of the following additional properties: (a) the antisense strand has a right shift from the typical 21-mer (i.e., the antisense strand includes nucleotides on the right side of the molecule when compared to the typical 21-mer), (b) the strands may not be completely complementary, i.e., the strands may contain simple mismatch pairings and (c) base modification, such as locked nucleic acid(s) may be included in the 5' end of the sense strand.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadelylation signal.

"Treating" as used herein refers to ameliorating at least one symptom of, curing and/or preventing the development of a disease or a condition.

III. Nucleic Acid Molecules of the Invention

Sources of nucleotide sequences from which the present nucleic acid molecules can be obtained include any vertebrate, such as a mammalian, cellular source.

As discussed above, the terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. For example, "isolated nucleic acid" is DNA containing less than 300, and or less than 100 sequential nucleotide bases that comprise a DNA sequence that encodes a siRNA that forms a hairpin structure with a duplex 21 base pairs in length, or a variant thereof, that is complementary or hybridizes to a sequence in a gene of interest and remains stably bound under stringent conditions as defined by methods well known in the art. Thus, the RNA or DNA is "isolated" in that it is free from at least one contaminating nucleic acid with which it is normally associated in the natural source of the RNA or DNA and may be substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

In addition to a DNA sequence encoding a siRNA, the nucleic acid molecules of the invention include double-stranded interfering RNA molecules, which are also useful to inhibit expression of a target gene.

As used herein, the term "recombinant nucleic acid", e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome that has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Oligonucleotide-mediated mutagenesis is a method for preparing substitution variants. Briefly, nucleic acid encoding a siRNA can be altered by hybridizing an oligonucleotide encoding the desired mutation to a DNA template, where the template is the single-stranded form of a plasmid or bacteriophage containing the unaltered or native gene sequence. After hybridization, a DNA polymerase is used to synthesize an entire second complementary strand of the template that will thus incorporate the oligonucleotide primer, and will code for the selected alteration in the nucleic acid encoding siRNA. Generally, oligonucleotides of about 21 nucleotides in length are used. An optimal oligonucleotide will have about 10 nucleotides that are completely complementary to the template on either side of the nucleotide(s) coding for the mutation. This ensures that the oligonucleotide will hybridize properly to the single-stranded DNA template molecule.

The DNA template can be generated by those vectors that are either derived from bacteriophage M13 vectors (the commercially available M13 mp 18 and M13 mp 19 vectors are suitable), or those vectors that contain a single-stranded phage origin of replication. Thus, the DNA that is to be mutated may be inserted into one of these vectors to generate single-stranded template. Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the DNA, and the other strand (the original template) encodes the native, unaltered sequence of the DNA. This heteroduplex molecule is then transformed into a suitable host cell, usually a prokaryote such as *E. coli* JM101. After the cells are grown, they are plated onto agarose plates and screened using the oligonucleotide primer radiolabeled with $^{32}$-phosphate to identify the bacterial colonies that contain the mutated DNA. The mutated region is then removed and placed in an appropriate vector, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(*S) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(*S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101.

IV. Expression Cassettes of the Invention

To prepare expression cassettes, the recombinant DNA sequence or segment may be circular or linear, double-stranded or single-stranded. Generally, the DNA sequence or segment is in the form of chimeric DNA, such as plasmid DNA or a vector that can also contain coding regions flanked by control sequences that promote the expression of the recombinant DNA present in the resultant transformed cell.

A "chimeric" vector or expression cassette, as used herein, means a vector or cassette including nucleic acid sequences from at least two different species, or has a nucleic acid sequence from the same species that is linked or associated in a manner that does not occur in the "native" or wild type of the species.

Aside from recombinant DNA sequences that serve as transcription units for a peptide, or portions thereof, a portion of the recombinant DNA may be untranscribed, serving a regulatory or a structural function. For example, the recombinant DNA may itself have a promoter that is active in mammalian cells, or may utilize a promoter already present in the genome that is the transformation target. Such promoters include the CMV promoter, as well as the RSV promoter, SV40 late promoter and retroviral LTRs (long terminal repeat elements), although many other promoter elements well known to the art, such as tissue specific promoters or regulatable promoters may be employed in the practice of the invention.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the siRNA, or the like. Such elements may be included in the DNA as desired to obtain the optimal performance of the siRNA in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of transformed cells from the population of cells sought to be transformed. In other embodiments, the selectable marker may be carried on a separate piece of DNA and used in a co-transformation procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transformed cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of *E. coli* and the luciferase gene from firefly *Photinus pyralis*. Expression of the reporter gene is assayed at a suitable time after the DNA has been introduced into the recipient cells.

The general methods for constructing recombinant DNA that can transform target cells are well known to those skilled in the art, and the same compositions and methods of construction may be utilized to produce the DNA useful herein.

The recombinant DNA can be readily introduced into the host cells, e.g., mammalian, bacterial, yeast or insect cells by transfection with an expression vector composed of DNA encoding the siRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. The DNA may be introduced into host cells via a vector. The host cell is may be of eukaryotic origin, e.g., plant, mammalian, insect, yeast or fungal sources, but host cells of non-eukaryotic origin may also be employed.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. For mammalian gene therapy, as described hereinbelow, it is desirable to use an efficient means of inserting a copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like. See, for example, U.S. Pat. Nos. 5,350,674 and 5,585,362.

A "transfected," "transformed" or "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the siRNA.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

The present invention provides a cell expression system for expressing exogenous nucleic acid material in a mammalian recipient. The expression system, also referred to as a "genetically modified cell," comprises a cell and an expression vector for expressing the exogenous nucleic acid material. The genetically modified cells are suitable for administration to a mammalian recipient, where they replace the endogenous cells of the recipient. Thus, the genetically modified cells may be non-immortalized and are non-tumorigenic.

According to one embodiment, the cells are transformed or otherwise genetically modified ex vivo. The cells are isolated from a mammal (such as a human), transformed (i.e., transduced or transfected in vitro) with a vector for expressing a heterologous (e.g., recombinant) gene encoding the therapeutic agent, and then administered to a mammalian recipient for delivery of the therapeutic agent in situ. The mammalian recipient may be a human and the cells to be modified are autologous cells, i.e., the cells are isolated from the mammalian recipient.

According to another embodiment, the cells are transformed or otherwise genetically modified in vivo. The cells from the mammalian recipient are transduced or transfected in vivo with a vector containing exogenous nucleic acid material for expressing a heterologous (e.g., recombinant) gene encoding a therapeutic agent and the therapeutic agent is delivered in situ.

As used herein, "exogenous nucleic acid material" refers to a nucleic acid or an oligonucleotide, either natural or synthetic, which is not naturally found in the cells; or if it is naturally found in the cells, is modified from its original or native form. Thus, "exogenous nucleic acid material" includes, for example, a non-naturally occurring nucleic acid that can be transcribed into an anti-sense RNA, a siRNA, as well as a "heterologous gene" (i.e., a gene encoding a protein that is not expressed or is expressed at biologically insignificant levels in a naturally-occurring cell of the same type). To illustrate, a synthetic or natural gene encoding human erythropoietin (EPO) would be considered "exogenous nucleic acid material" with respect to human peritoneal mesothelial cells since the latter cells do not naturally express EPO. Still another example of "exogenous nucleic acid material" is the introduction of only part of a gene to create a recombinant gene, such as combining an regulatable promoter with an endogenous coding sequence via homologous recombination.

V. Methods for Introducing the Expression Cassettes of the Invention into Cells

The condition amenable to gene inhibition therapy may be a prophylactic process, i.e., a process for preventing disease or an undesired medical condition. Thus, the instant invention embraces a system for delivering siRNA that has a prophylactic function (i.e., a prophylactic agent) to the mammalian recipient.

The inhibitory nucleic acid material (e.g., an expression cassette encoding siRNA directed to a gene of interest) can be introduced into the cell ex vivo or in vivo by genetic transfer methods, such as transfection or transduction, to provide a genetically modified cell. Various expression vectors (i.e., vehicles for facilitating delivery of exogenous nucleic acid into a target cell) are known to one of ordinary skill in the art.

As used herein, "transfection of cells" refers to the acquisition by a cell of new nucleic acid material by incorporation of added DNA. Thus, transfection refers to the insertion of nucleic acid into a cell using physical or chemical methods. Several transfection techniques are known to those of ordinary skill in the art including: calcium phosphate DNA co-precipitation, DEAE-dextran, electroporation, cationic liposome-mediated transfection, tungsten particle-facilitated microparticle bombardment, and strontium phosphate DNA co-precipitation.

In contrast, "transduction of cells" refers to the process of transferring nucleic acid into a cell using a DNA or RNA virus. An RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The exogenous nucleic acid material can include the nucleic acid encoding the siRNA together with a promoter to control transcription. The promoter characteristically has a specific nucleotide sequence necessary to initiate transcription. The exogenous nucleic acid material may further include additional sequences (i.e., enhancers) required to obtain the desired gene transcription activity. For the purpose of this discussion an "enhancer" is simply any non-translated DNA sequence that works with the coding sequence (in cis) to change the basal transcription level dictated by the promoter. The exogenous nucleic acid material may be introduced into the cell genome immediately downstream from the promoter so that the promoter and coding sequence are operatively linked so as to permit transcription of the coding sequence. An expression vector can include an exogenous promoter element to control transcription of the inserted exogenous gene. Such exogenous promoters include both constitutive and regulatable promoters.

Naturally-occurring constitutive promoters control the expression of essential cell functions. As a result, a nucleic acid sequence under the control of a constitutive promoter is expressed under all conditions of cell growth. Constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the beta-actin promoter, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others.

Nucleic acid sequences that are under the control of regulatable promoters are expressed only or to a greater degree in the presence of an inducing agent (e.g., transcription under control of the metallothionein promoter is greatly increased in presence of certain metal ions). Regulatable promoters include responsive elements (REs) that stimulate transcription when their inducing factors are bound. For example, there are REs for serum factors, steroid hormones, retinoic acid and cyclic AMP. Promoters containing a particular RE can be chosen in order to obtain an regulatable response and in some cases, the RE itself may be attached to a different promoter, thereby conferring regulatability to the encoded nucleic acid sequence. Thus, by selecting the appropriate promoter (constitutive versus regulatable; strong versus weak), it is possible to control both the existence and level of expression of a nucleic acid sequence in the genetically modified cell. If the nucleic acid sequence is under the control of an regulatable promoter, delivery of the therapeutic agent in situ is triggered by exposing the genetically modified cell in situ to conditions for permitting transcription of the nucleic acid sequence, e.g., by intraperitoneal injection of specific inducers of the regulatable promoters which control transcription of the agent. For example, in situ expression of a nucleic acid sequence under the control of the metallothionein promoter in genetically modified cells is enhanced by contacting the genetically modified cells with a solution containing the appropriate (i.e., inducing) metal ions in situ.

Accordingly, the amount of siRNA generated in situ is regulated by controlling such factors as the nature of the promoter used to direct transcription of the nucleic acid sequence, (i.e., whether the promoter is constitutive or regulatable, strong or weak) and the number of copies of the exogenous nucleic acid sequence encoding a siRNA sequence that are in the cell.

In addition to at least one promoter and at least one heterologous nucleic acid sequence encoding the siRNA, the expression vector may include a selection gene, for example, a neomycin resistance gene, for facilitating selection of cells that have been transfected or transduced with the expression vector.

Cells can also be transfected with two or more expression vectors, at least one vector containing the nucleic acid sequence(s) encoding the siRNA(s), the other vector containing a selection gene. The selection of a suitable promoter, enhancer, selection gene and/or signal sequence is deemed to be within the scope of one of ordinary skill in the art without undue experimentation.

The following discussion is directed to various utilities of the instant invention. For example, the instant invention has utility as an expression system suitable for silencing the expression of gene(s) of interest. The instant invention also provides various methods for making and using the above-described genetically-modified cells. The instant invention also provides methods for genetically modifying cells of a mammalian recipient in vivo. According to one embodiment, the method comprises introducing an expression vector for expressing a siRNA sequence in cells of the mammalian recipient in situ into the recipient.

VI. Delivery Vehicles for the Expression Cassettes of the Invention

The selection and optimization of a particular expression vector for expressing a specific siRNA in a cell can be accomplished by obtaining the nucleic acid sequence of the siRNA, possibly with one or more appropriate control regions (e.g., promoter, insertion sequence); preparing a vector construct comprising the vector into which is inserted the nucleic acid sequence encoding the siRNA; transfecting or transducing cultured cells in vitro with the vector construct; and determining whether the siRNA is present in the cultured cells.

Vectors for cell gene therapy include viruses, such as replication-deficient viruses (described in detail below). Exemplary viral vectors are derived from Harvey Sarcoma virus, ROUS Sarcoma virus, (MPSV), Moloney murine leukemia virus, lentiviruses (HIV, FIV) and DNA viruses (e.g., adenovirus).

Replication-deficient retroviruses are capable of directing synthesis of all virion proteins, but are incapable of making infectious particles. Accordingly, these genetically altered retroviral expression vectors have general utility for high-efficiency transduction of nucleic acid sequences in cultured cells, and specific utility for use in the method of the present invention. Such retroviruses further have utility for the efficient transduction of nucleic acid sequences into cells in vivo. Retroviruses have been used extensively for transferring nucleic acid material into cells. Standard protocols for producing replication-deficient retroviruses (including the steps of incorporation of exogenous nucleic acid material into a plasmid, transfection of a packaging cell line with plasmid, production of recombinant retroviruses by the packaging cell line, collection of viral particles from tissue culture media, and infection of the target cells with the viral particles) are known in the art.

An advantage of using retroviruses for gene therapy is that the viruses insert the nucleic acid sequence encoding the siRNA into the host cell genome, thereby permitting the nucleic acid sequence encoding the siRNA to be passed on to the progeny of the cell when it divides. Promoter sequences in the LTR region have been reported to enhance expression of an inserted coding sequence in a variety of cell types. Some disadvantages of using a retrovirus expression vector are (1) insertional mutagenesis, i.e., the insertion of the nucleic acid sequence encoding the siRNA into an undesirable position in the target cell genome which, for example, leads to unregulated cell growth and (2) the need for target cell proliferation in order for the nucleic acid sequence encoding the siRNA earned by the vector to be integrated into the target genome.

Another viral candidate useful as an expression vector for transformation of cells is the adenovirus, a double-stranded DNA virus. The adenovirus is infective in a wide range of cell types, including, for example, muscle and endothelial cells. The adenovirus also has been used as an expression vector in muscle cells in vivo.

Adenoviruses (Ad) are double-stranded linear DNA viruses with a 36 kb genome. Several features of adenovirus have made them useful as transgene delivery vehicles for therapeutic applications, such as facilitating in vivo gene delivery. Recombinant adenovirus vectors have been shown to be capable of efficient in situ gene transfer to parenchymal cells of various organs, including the lung, brain, pancreas, gallbladder, and liver. This has allowed the use of these vectors in methods for treating inherited genetic diseases, such as cystic fibrosis, where vectors may be delivered to a target organ. In addition, the ability of the adenovirus vector to accomplish in situ tumor transduction has allowed the development of a variety of anticancer gene therapy methods for non-disseminated disease. In these methods, vector containment favors tumor cell-specific transduction.

Like the retrovirus, the adenovirus genome is adaptable for use as an expression vector for gene therapy, i.e., by removing the genetic information that controls production of the virus itself. Because the adenovirus functions in an extrachromosomal fashion, the recombinant adenovirus does not have the theoretical problem of insertional mutagenesis.

Several approaches traditionally have been used to generate the recombinant adenoviruses. One approach involves direct ligation of restriction endonuclease fragments containing a nucleic acid sequence of interest to portions of the adenoviral genome. Alternatively, the nucleic acid sequence of interest may be inserted into a defective adenovirus by homologous recombination results. The desired recombinants are identified by screening individual plaques generated in a lawn of complementation cells.

Most adenovirus vectors are based on the adenovirus type 5 (Ad5) backbone in which an expression cassette containing the nucleic acid sequence of interest has been introduced in place of the early region 1 (E1) or early region 3 (E3). Viruses in which E1 has been deleted are defective for replication and are propagated in human complementation cells (e.g., 293 or 911 cells), which supply the missing gene E1 and pIX in trans.

Thus, as will be apparent to one of ordinary skill in the art, a variety of suitable viral expression vectors are available for transferring exogenous nucleic acid material into cells. The selection of an appropriate expression vector to express a therapeutic agent for a particular condition amenable to gene silencing therapy and the optimization of the conditions for insertion of the selected expression vector into the cell, are within the scope of one of ordinary skill in the art without the need for undue experimentation.

In another embodiment, the expression vector is in the form of a plasmid, which is transferred into the target cells by one of a variety of methods: physical (e.g., microinjection, electroporation, scrape loading, microparticle bombardment) or by cellular uptake as a chemical complex (e.g., calcium or strontium co-precipitation, complexation with lipid, complexation with ligand). Several commercial products are available for cationic liposome complexation including Lipofectin™ (Gibco-BRL, Gaithersburg, Md.) and Transfectam™ (ProMega, Madison, Wis.). However, the efficiency of transfection by these methods is highly dependent on the nature of the target cell and accordingly, the conditions for optimal transfection of nucleic acids into cells using the above-mentioned procedures must be optimized. Such optimization is within the scope of one of ordinary skill in the art without the need for undue experimentation.

VII. Diseases and Conditions Amendable to the Methods of the Invention

In the certain embodiments of the present invention, a mammalian recipient to an expression cassette of the invention has a condition that is amenable to gene silencing therapy. As used herein, "gene silencing therapy" refers to administration to the recipient exogenous nucleic acid material encoding a therapeutic siRNA and subsequent expression of the administered nucleic acid material in situ. Thus, the phrase "condition amenable to siRNA therapy" embraces conditions such as genetic diseases (i.e., a disease condition that is attributable to one or more gene defects), acquired pathologies (i.e., a pathological condition that is not attributable to an inborn defect), cancers, diseases and prophylactic processes (i.e., prevention of a disease or of an undesired medical condition). A gene "associated with a condition" is a gene that is either the cause, or is part of the cause, of the condition to be treated. Examples of such genes include genes associated with a disease. Also siRNA expressed from viral vectors may be used for in vivo antiviral therapy using the vector systems described.

Accordingly, as used herein, the term "therapeutic siRNA" refers to any siRNA that has a beneficial effect on the recipient. Thus, "therapeutic siRNA" embraces both therapeutic and prophylactic siRNA.

A number of diseases caused by gene defects have been identified. For example, this strategy can be applied to disorders, such as asthma, COPD, cystic fibrosis, or interstitial lung disease. The methods of the present invention can be used to treat genetic disorders of the airway epithelia. Alternatively, the present invention can be used to treat acquired pathologies. As used herein, "acquired pathology" refers to a disease or syndrome manifested by an abnormal physiological, biochemical, cellular, structural, or molecular biological state. For example, the disease could be a viral disease, such as hepatitis or AIDS.

The condition amenable to gene silencing therapy alternatively can be a genetic disorder or an acquired pathology that is manifested by abnormal cell proliferation, e.g., cancer. According to this embodiment, the instant invention is useful for silencing a gene involved in neoplastic activity.

The present invention can also be used to inhibit overexpression of one or several genes that impart differentiation.

VIII. Dosages, Formulations and Routes of Administration of the Agents of the Invention The agents of the invention may be administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

Administration of siRNA may be accomplished through the administration of the nucleic acid molecule encoding the siRNA. Pharmaceutical formulations, dosages and routes of administration for nucleic acids are known in the art.

The present invention envisions treating a disease, for example, an airway epithelial disease, in a mammal by the administration of an agent, e.g., a nucleic acid composition, an expression vector, or a viral particle of the invention.

Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they may be combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, dilutent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for aerosol administration and may be presented in unit dose form in ampules, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions, saline solutions and water.

The invention will now be illustrated by the following non-limiting examples.

EXAMPLES

Example 1

Delivery of RNA to Pulmonary Epithelium In Vitro

Figure 20A:
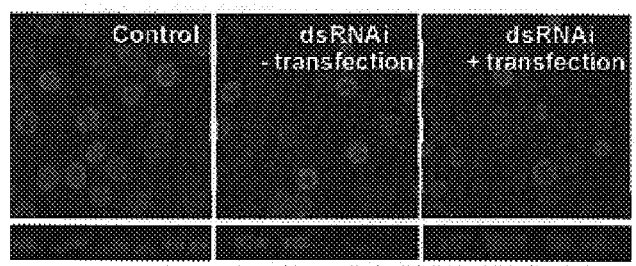
FIG. 20A shows the delivery of RNA to pulmonary epithelium in vitro.

An issue of significant importance for successful mRNA targeting is the ability to efficiently deliver double stranded siRNA, or siRNA expression vectors, to the cytoplasm of airway epithelia. The polarized epithelial model presents more challenges for delivery and more closely represents the in vivo epithelium. The inventors asked if synthetic double stranded siRNA oligonucleotides could also be delivered to well-differentiated airway epithelial cells in vitro. The inventors evaluated the efficiency of siRNA uptake in airway epithelia using Cy3-fluorescently tagged double stranded 21-mer RNAi oligonucleotides (Dharmacon). The reagent was delivered to the polarized primary human epithelia with or without a commercial transfection reagent optimized for dsRNAi (TransIT-TKO, cat#MIR 2154, Mirus). Cytoplasmic staining was observed, indicating delivery of the labeled RNAi following apical application of 100 µl of the reagent at a final concentration of 100 nM (FIG. 20A). The Cy3 labeled double-stranded oligonucleotide 21-mer was applied with Mirus transfection reagent. The cells were observed as en face and Z series confocal images. DAPI (blue) stains the nuclei. The abundance of fluorescent signal was greater when the transfection reagent was used. A similar method was also applied to deliver the labeled oligonucleotides to polarized primary cultures of human airway epithelia and visualized the cells using confocal microscopy. These studies document the feasibility of delivering RNAi oligonucleotides to airway epithelia.

Figure 20B:
FIG. 20B shows that siRNA against eGFP leads to specific diminution of eGFP expression in A549 cells.

To demonstrate the feasibility of functional RNAi machinery in respiratory epithelia, plasmids expressing eGFP and eGFP RNAi (Xia et al., 2002) were co-transfected into A549 cells using lipofectamine. The plasmid expressing eGFP RNAi used in these studies was previously published by Davidson et al (Xia et al., 2002). Specifically, siRNA against eGFP leads to specific diminution of eGFP expression in A549 cells. Plasmids expressing eGFP and eGFP RNAi were co-transfected into A549 cells (at a ratio of 2:1 or 8:1, RNAi:plasmid). Both concentrations of RNAi knocked down eGFP expression. (FIG. 20B) Photomicrographs were taken 48 hours following siRNA delivery by lipofectamine transfection. Thus, siRNA resulted in specific diminution of eGFP expression in A549 cells. This result documents the feasibility of applying RNAi approaches in the respiratory epithelia.

Example 2

In vivo Delivery of RNAi to the Lungs of Mice.

Mucociliary clearance and other pulmonary innate defense mechanisms pose significant barriers to gene transfer vectors. The inventors previously demonstrated that $Ca^{2+}$ chelators such as EGTA enhance gene transfer to well differentiated airway epithelia. U.S. patent application Ser. No. 09/448,613, which issued as U.S. Pat. No. 6,855,549. This effect may result from the combined effects of cilia stasis and the opening of epithelial tight junctions. Furthermore, viscoelastic agents enhance gene transfer to airway epithelia when formulated with adenoviral vectors.

Methods of in vivo delivery of RNAi in mice were developed. These include the following approaches: 1) Delivery as a viral gene transfer vector encoding the shRNA sequence (e.g, adenovirus or retrovirus), 2) Delivery as a non-viral vector encoding the RNAi sequence, such as plasmid DNA, and 3) Delivery of 21-mer to 23-mer dsRNA oligonucleotides (with or without a lipofection agent or electroporation).

Figure 7:
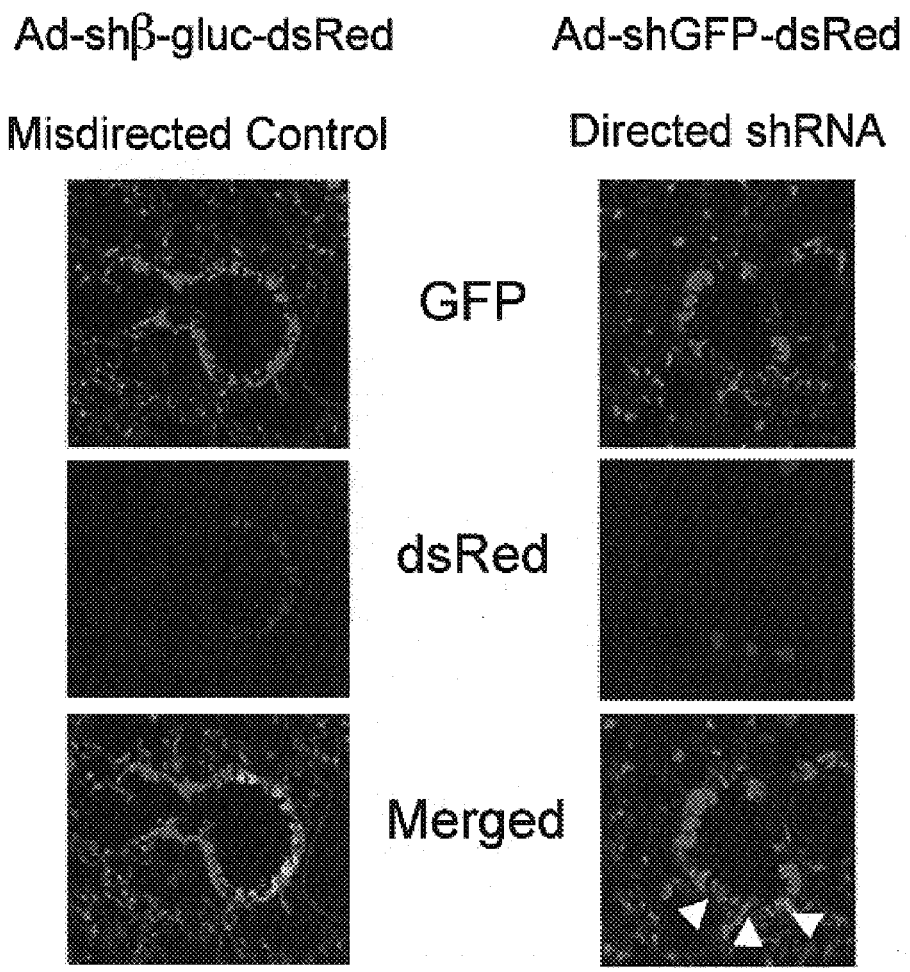
FIG. 7. Gene transfer to the airways with 1% carboxymethylcellulose formulated adenoviral vector expressing shRNA against GFP and a second reporter (dsRed) causes knock-down of GFP expression in the airway epithelia of GFP mice. GFP mice were transduced with adenoviral vectors expressing shRNA against beta-glucuronidase or GFP. Vectors also expressed dsRed (red fluorescent protein). Virus was formulated with 1% carboxymethylcellulose gel and delivered to the airways of GFP transgenic mice by direct tracheal instillation in a volume of 50 microliters. Five days later mice were sacrificed and lung tissue examined under fluorescence microscopy. Cells receiving the misdirected control vector showed predominantly yellow cells in merged image consistent with co-expression of GFP and dsRed. In contrast, in mice receiving shGFP, cells expressing only dsRed (arrowheads) were more abundant, consistent with knock down of GFP. Vector knock down of GFP expression is demonstrated by a loss of green staining in cells that maintain the dsRed expression.

The inventors tested the gene transfer enhancing properties of gels containing methylcellulose, carboxymethylcellulose, and pluronic F127 by formulating them with an adenoviral vector expressing nuclear targeted beta-galactosidase. These formulations were compared to 400 mM EGTA, Flonase, and no formulation controls. The inventors delivered the formulations to mice via tracheal intubation via a 24 gauge catheter and four days later measured beta-galactosidase expression by enzyme activity assay or X-gal staining. With each of the gels tested, gene transfer equaled or exceeded the gene transfer observed with the positive controls. The gel formulations markedly enhanced the delivery of the vector to the respiratory epithelium. Gene expression was largely confined to the conducting airways. As added conformation of the results, the gels were formulated with an adenoviral vector expressing firefly luciferase. Specifically, the inventors delivered an adenoviral vector expressing luciferase in a 1% methylcellulose gel formulation to the airways of mice. Five days following gene transfer in a living mouse diffuse photon release from airway epithelia was detected using a CCD camera. See, FIG. 6. The quantity of light emitted was greater from the animals receiving the vector formulated with the MC gel than that with EGTA or no excipient. In another proof of principle experiment the investigators used GFP mice as a model and an adenoviral vector expressing shRNA against GFP to knock down GFP. The vector also expressed dsRed as a marker (a red fluorescent protein). In this experiment the adenoviral vector expressing the shRNA was formulated with 1% CMC gels. Five days following gene transfer, cells expressing the dsRed were visible in the airway epithelium. See, FIG. 7. It is important to note that cells expressing dsRed also showed diminished GFP expression, consistent with knock down by the shRNA against GFP. This is consistent with efficient uptake and expression of the shRNA. These data indicate that such formulations of vector or nucleic acid in viscoelastic gels can be used to greatly enhance efficiency of siRNA delivery to the epithelial cells.

Example 3

Gene Transfer Formulated with Viscoelastic Gels

A. Formulating an Adenoviral Vector in Viscoelastic Gels Markedly Enhances Gene Transfer to the Conducting Airways.

Figure 21:
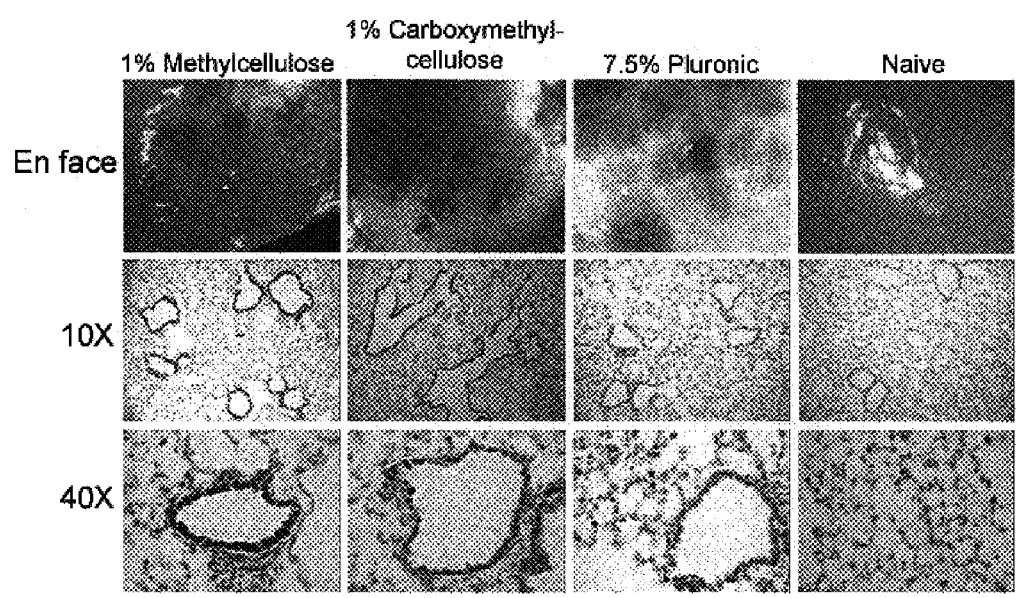
FIG. 21 shows gene transfer enhancing effects of an adenoviral vector formulated with viscoelastic gels in mice in vivo.

The gene transfer enhancing effects of an adenoviral vector formulated with viscoelastic gels was tested in mice in vivo. A nuclear targeted beta-galactosidase expressing adenoviral serotype 5-based vector (AdbetaGal, as a marker for shRNA) was formulated with 1% methycellulose A4C, 1% carboxymethylcellulose, or 7.5% Pluronic-brand polaxamer polymer F127. Approximately $2.5 \times 10^8$ pfu of vector/gel formulation in a 50 microliter volume was delivered via direct oro-tracheal intubation to the airways of 3 month old male Balb/c mice under ketamine anesthesia. Four days following vector delivery, the mice were sacrificed, the lungs were removed, fixed in 2% formaldehyde/0.2% gluteraldehyde, and X-gal stained for 4 hours at 37° C. The appearance of beta-galactosidase positive cells was readily apparent to the naked eye in lungs that received gel formulated viral vector, but not in naive animals or control animals receiving the adenovirus without the gel. Following X-gal staining, the lungs were paraffin embedded, sectioned and counterstained with nuclear fast red. Upon microscopic examination, the transduction of the conducting airway epithelium with AdbetaGal formulated with 1% methycellulose or 1% carboxymethycellulose was striking (i.e., noticeably higher), while the conducting airway cell transduction achieved by the Pluronic-brand polaxamer polymer vehicle or the no vehicle control was significantly lower (FIG. 21).

These studies demonstrate that two of the evaluated gel formulations, used in a single concentration, dramatically improve the efficiency of gene transfer. It is important to note that gene delivery is concentrated in the conducting airways, with little gene transfer to the alveoli. This is a very novel result that has important implications for the future pulmonary applications as the cells of the conducting airway epithelium are a key target population for correction in diseases such as asthma, COPD and cystic fibrosis. By restricting gene transfer to the airway epithelium and avoiding delivery to the large alveolar surface area, the inventors also effectively increased the concentrations of RNAi that can be delivered to the target cells.

B. Viscoelastic Gels do not Affect Tight Junction Permeability.

Figure 2:
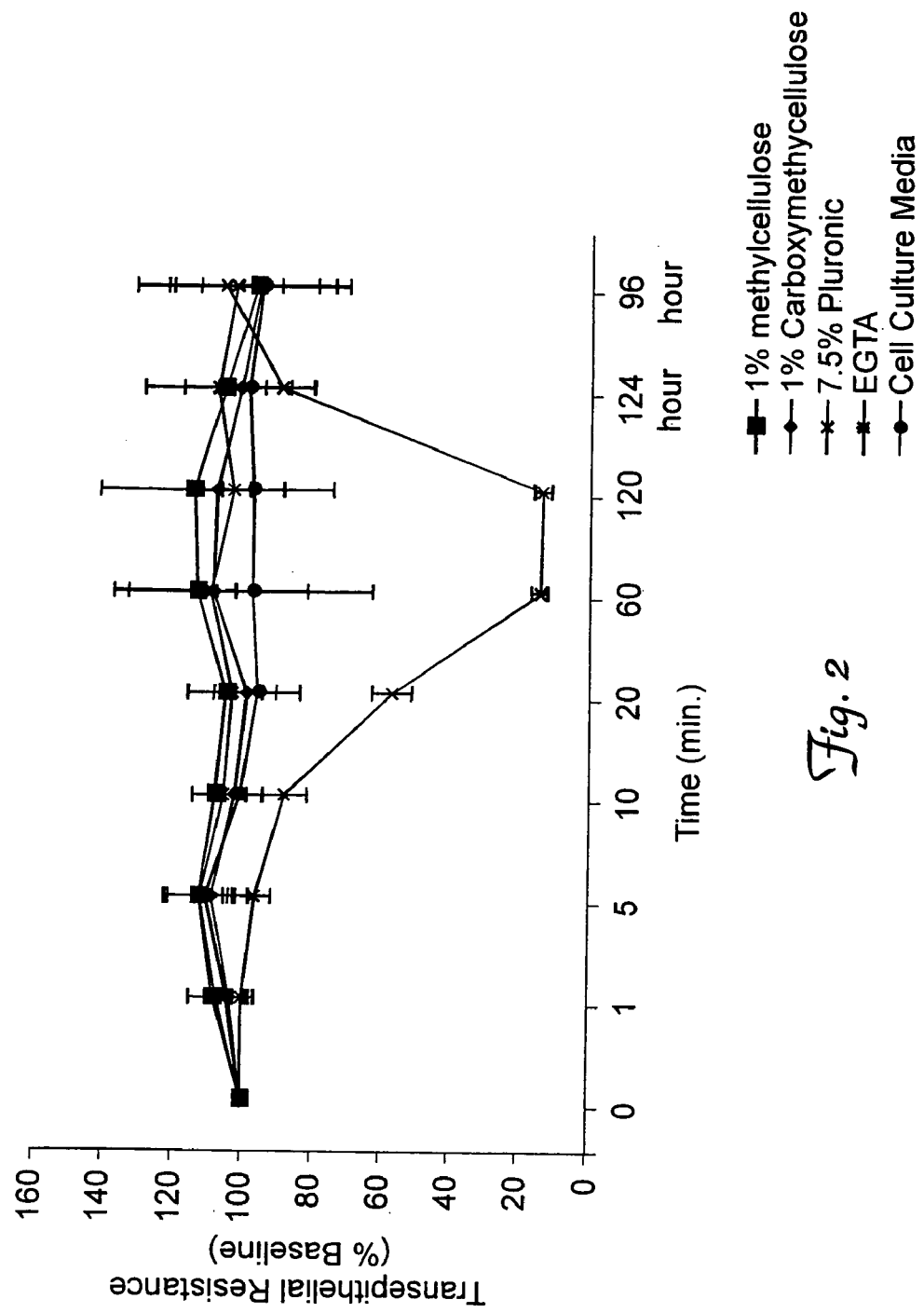
FIG. 2. Effects of viscoelastic gels and EGTA on the barrier properties of airway epithelia. Viscoelastic gels or EGTA (6 mM) were applied to the apical surface of primary cultures of human airway epithelia. The integrity of the epithelial sheet was monitored by measuring transepithelial resistance.

To determine if the viscoelastic gels disrupt tight junctions, formulations identical to those used in the in vivo experiment were applied to the apical surface of an immortalized human airway epithelial derived cell line, NuLi, that is grown at an air liquid interface (Zabner 2003). As shown in FIG. 2, the viscoelastic gels did not significantly affect the trans-epithelial resistance of the airway epithelia. In contrast, vector formulation with EGTA transiently disrupted the resistance. Viscoelastic gels do not disrupt tight junctions. Various gels were applied to well-differentiated primary cultures of human airway epithelia and epithelial integrity monitored by transepithelial resistance. EGTA caused a transient fall in transepithelial resistance, but the viscoelastic gels had caused no significant change.

C. Viscoelastic Gels Inhibit Mucociliary Clearance.

Mucociliary transport of the gel formulations was measured using a bovine tracheal explant model (Shah 2003). Full-thickness segments of bovine trachea obtained from local meatpackers were placed into Petri dishes containing sufficient Krebs-Ringer buffer to bathe the cartilaginous region of the tissue. These were placed into a humidified chamber and the clearance rate across the tissue is measured by following the movement of the formulation across the surface using a stereomicroscope. To assist with visualization, an insoluble particulate that is colored or fluorescent (i.e., charcoal, latex microspheres) was incorporated in the formulation. Initial control experiments were conducted with each tissue to measure its basal mucociliary transport rate (MTR). Gels were applied to acute preparations of intact bovine trachea and clearance measured visually by monitoring the movement of carbon particles.

TABLE 1

|  | Basal MTR (cm/min) | Formulation MTR (cm/min) | % decrease in MTR |
| --- | --- | --- | --- |
| Carboxymethylcellulose (1%) | 1.00 | 0.60 | 40% |
| Methylcellulose (1%) | 0.67 | 0.57 | 14% |
| Pluronic-brand polaxamer polymer F127 (7.5%) | 0.67 | 0.60 | 10% |

These data show that these polymeric gels are capable of slowing mucociliary clearance. It is hypothesized that the resulting increase in mucosal contact time allows for significantly improved uptake of the vectors via receptor independent mechanisms.

D. Formulation of lentiviral vectors in viscoelastic gels does not destabilize the vector.

Based on the in vivo data, it is clear that viscoelastic gel formulations have no significant deleterious effect on the titer of an encapsidated and intrinsically stable vector such as adenovirus. However, for the treatment of diseases of the respiratory epithelium, gene transfer with an integrating vector such as lentivirus could provide stable long term gene expression of shRNA. Such approaches may also enhance delivery of siRNA oligonucleotides.

To test if an enveloped lentivirus is stable in such a formulation, the inventors incubated each gel with VSV-G pseudotyped feline immunodeficiency virus (FIV)-based vector for 30 minutes at 37° C. and then titered the virus by limiting dilution on HT1080 cells (Wang 1999).

It is important to note that there was no significant drop in vector titer following incubation with any of the gels tested. Thus, formulating lentiviral vectors in viscoelastic gels does not inactivate these enveloped viruses. This result suggests that these and other related gel formulations can be used to enhance delivery of enveloped viral vectors expressing shRNA to respiratory epithelia.

TABLE 2

| Gel Formulation | Titer (TU/ml) |
| --- | --- |
| Carboxymethylcellulose (1%) | $6 \times 10^8$ |
| Methylcellulose (1%) | $4 \times 10^8$ |
| Pluronic-brand polaxamer polymer (7.25%) | $5 \times 10^8$ |
| Cultured Media Control | $4 \times 10^8$ |

Example 4

Use of 27-mer RNA/DNA Oligonucleotides in Respiratory Epithelia

The present inventors investigated the efficacy of novel 27-mer RNA/DNA oligonucleotides in respiratory epithelia. These 27-mers siRNAs are longer than conventional siRNAs, and are efficiently processed by Dicer and loaded into the RISC complex (Kim et al., *Nature Biotech* 23:222 (2005)). This technique of oligonucleotide design has been shown to improve potency of RNAi. The mechanism is not fully understood, but the use of chimeric DNA bases may bias strand loading for the antisense strand. The inventors have designed and evaluated a series of oligonucleotides against the following targets: respiratory RNA virus mRNAs (the N, NS1, P, and L genes of the A2 strain of RSV) and host gene products (interleukin 8, IL-8).

Figure 8:
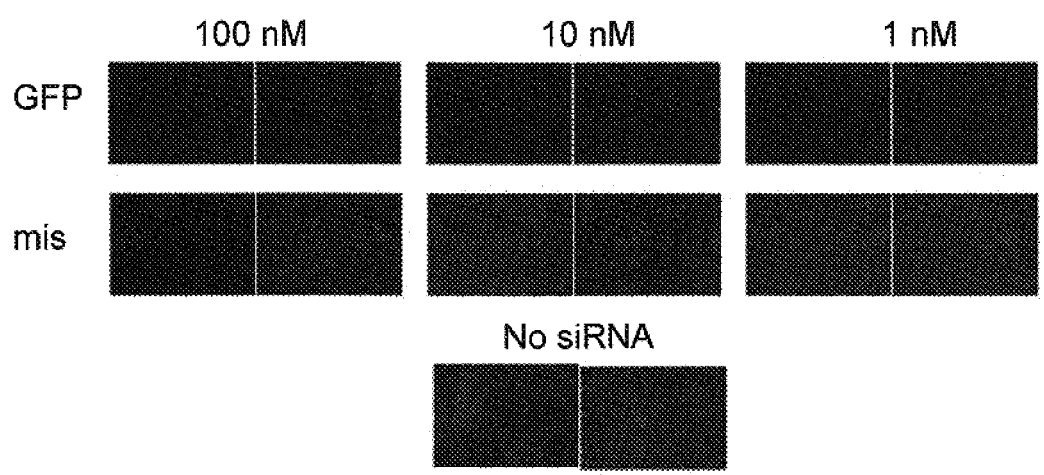
FIG. 8. 27-mer RNAi oligonucleotide designed against eGFP was transfected into 293 cells at concentrations of 100 nM, 10 nM, and 1 nM siGFP. An eGFP expressing plasmid, pAd5CMV-GFP, was transfected at the same time using Lipofectamine 2000 transfection reagent. A negative misdirected control siRNA was included. The media was changed after 4 hours, and knock down of eGFP was assessed at 24 hr by direct fluorescence microscopy.
Figure 9:
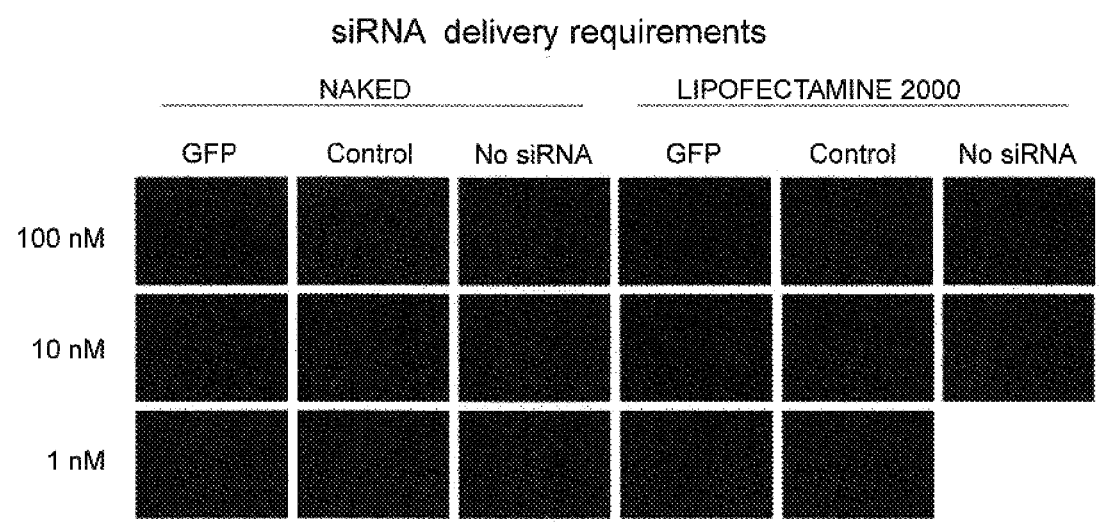
FIG. 9. Delivery of a 27-mer siRNA against eGFP is effective when delivered complexed with a lipofection reagent (lipofectamine 2000) or as uncomplexed, "naked" oligonucleotide.
Figure 10A:
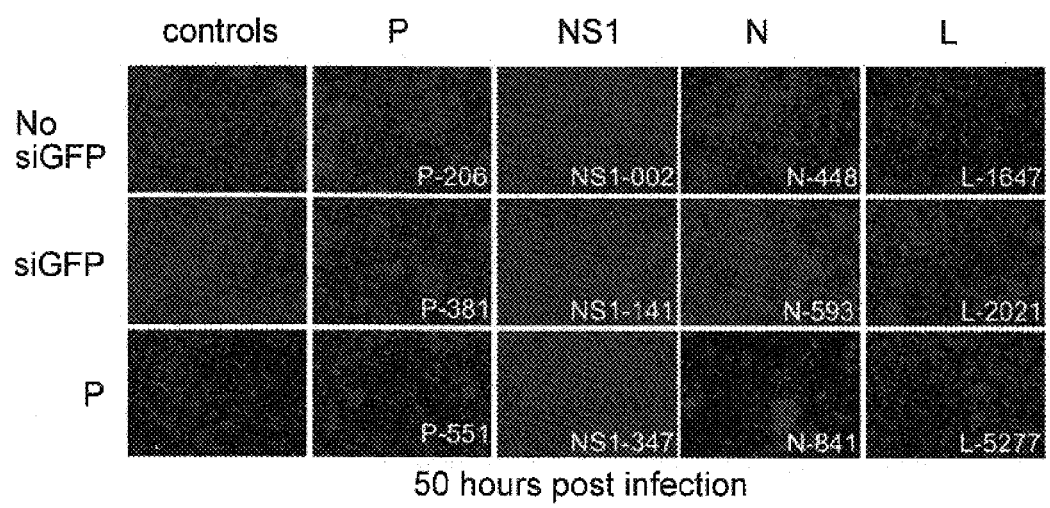
FIG. 10A shows RSV A2 strain expressing the red fluorescent protein (RFP) was used to infect 293 cells and infection monitored at 24 and 50 hrs and infection assessed by direct fluorescence microscopy. Oligos against P, N, and L genes (but not NS1) all demonstrated efficacy, as shown by decreased RFP expression. These direct fluorescence results were confirmed by western blots with polyclonal antisera recognizing RSV proteins.
Figure 10B:
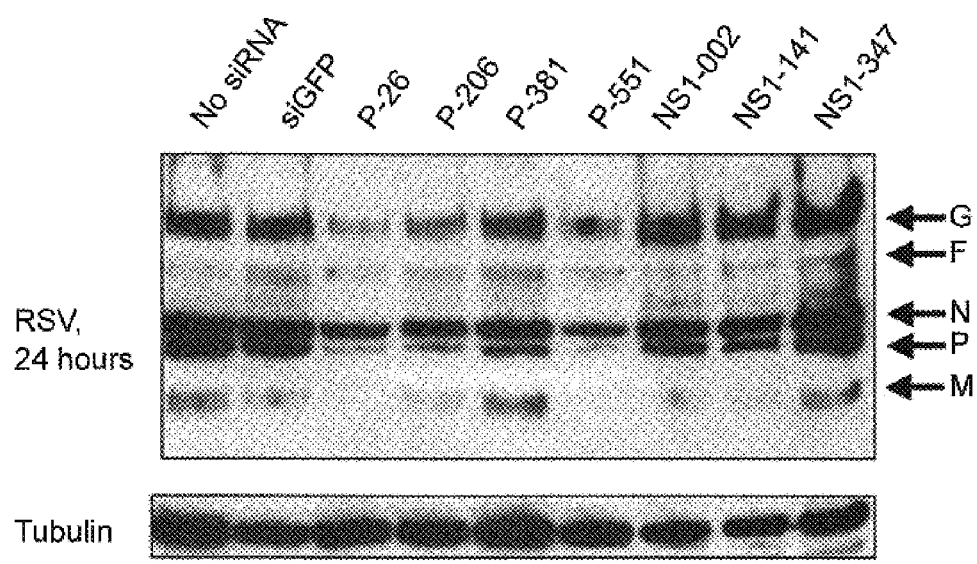
FIG. 10B shows that 27-mer siRNA oligonucleotides against the P gene (P1-4) diminish RSV protein abundance while 27-mer siRNA oligonucleotides targeting the NS1 gene did not inhibit RSV protein production. Beta-tubulin was used as a control protein for gel loading.
Figure 10C:
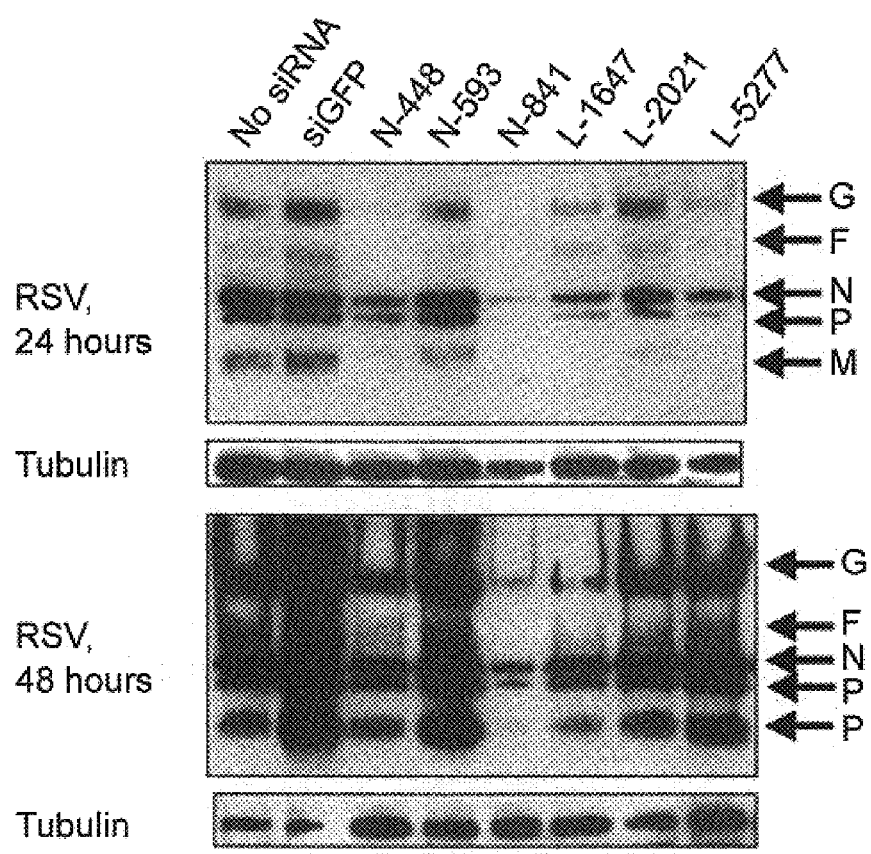
FIG. 10C shows that 27-mer siRNA oligonucleotides against the N and L genes also inhibit RSV protein expression. Controls include no siRNA and an irrelevant siRNA targeting eGFP (siGFP).

As shown in FIG. 8, the inventors first evaluated the efficacy of the 27-mer strategy using the oligonucleotides designed against the reporter gene eGFP in a co-transfection experiment. This experiment demonstrated the efficacy of the siRNA against eGFP at low nM and high pM concentrations. FIG. 9 shows that the 27-mer siRNA against GFP can be delivered using a lipofection agent or "naked" (uncomplexed) and that the 27-mer siRNA still retained efficacy. Lipofectamine 2000 increased potency of siRNAs, but measurable knockdown is attainable without transfection reagents. This result suggested that uncomplexed siRNA oligonucleotides might be delivered to epithelia to effect gene knockdown. To demonstrate the principle of siRNA inhibition of an RNA respiratory virus, the inventors designed a series of series of 27-mer oligonucleotides to the sequence of the RSV A2 strain NS 1, P, N and L genes (see FIG. 14B for details of oligonucleotide design). As shown in FIGS. 10A-C, 27-mer oligonucleotides against the RSV P, N, and L genes all effected inhibition of the virus, as demonstrated by decreased viral load in cultured cells and diminution of RSV proteins as assessed by western blot. P was shown previously to be an effective target for RNAi (Bitko et al. 2001). The inventors found that P-381 uses the reported sequence within a Dicer Substrate siRNA (FIG. 10B). They also found that siRNAs against N, L decreased viral protein at 24 and 48 hours (FIG. 10C). Western results correlated with microscopy data. Thus, N, L, and P are essential for replication of RSV.

Figure 11:
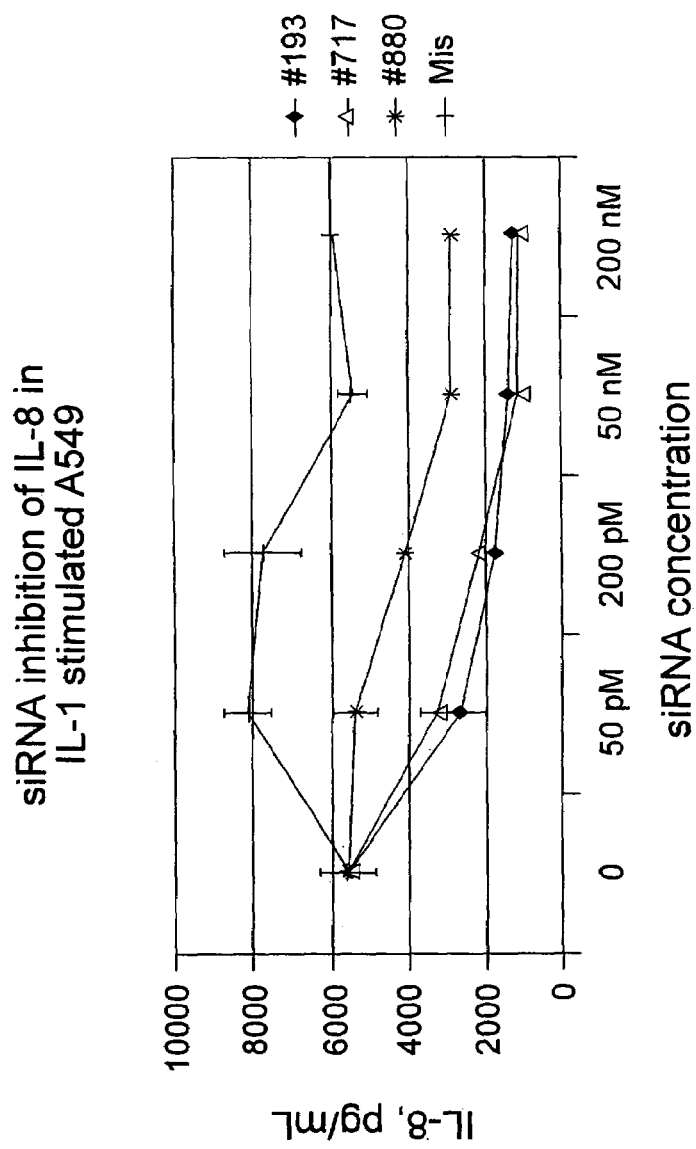
FIG. 11. 27-mer siRNA oligonucleotides against human IL-8 caused dose-dependent inhibition of IL-8 protein production in IL-1 stimulated A549 respiratory epithelial cells. IL-1 stimulated cells were transfected with the indicated concentrations of RNAi oligonucleotides and IL-8 protein was measured in cell culture media by ELISA XX hrs after stimulation. #193, #717, and #880 refer to the IL-8 27-mer oligonucleotides (as indicated in FIG. 14A). "Mis" indicates the effects of a mis-directed control oligonucleotide (siRNA against RSV NS1).

Another class of attractive targets in respiratory epithelia are host gene products that contribute to inflammation. The inventors designed 27-mer oligonucleotides against the human IL-8 gene (FIG. 14A) and evaluated their efficacy in A549 cells under resting or IL-1 stimulated conditions. An IL-8 ELISA assay was used to measure effects. As shown in FIG. 11, all three oligonucleotides caused a dose-dependent reduction in the IL-1 stimulated release of IL-8. IL-8 is induced by RSV and promotes influx of neutrophils. The inventors found that Dicer substrate siRNAs silenced IL-8 at 50 pM, and that siRNAs #193, #717, and #880 inhibited IL-8 in A549 cells as assessed by ELISA.

Figure 12:
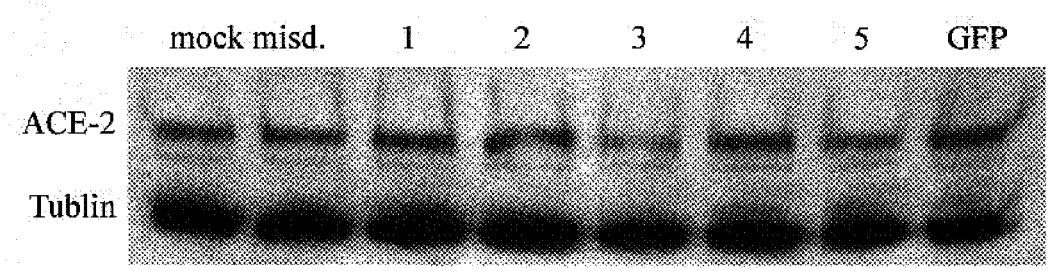
FIG. 12. shRNA against human ACE2. A 293T-ACE-2 expressing stable cell line was transfected with mU6-shRNAs (800 ng/well) using Lipofectamine 2000. Media was changed after 4 hours and cell lysates harvested at 48 hours post transfection. ACE2 knockdown was assessed by western blot. shRNA #3 resulted in knockdown of ACE2 protein.

The inventors also designed a series of short hairpin siRNAs against angiotensin converting enzyme 2 (ACE2), the cellular receptor for the SARS-Coronavirus (FIG. 16). As shown in FIG. 12, transfection of a plasmid expressing shRNA against human ACE2 stably expressed in 293 cells resulted in knockdown of ACE2 as assessed by western blot (shRNA #3 shows efficacy).

An important issue for the translation of RNAi to a useful therapeutic is the delivery of the shRNA or siRNA to the target cells, respiratory epithelia. To this end, the inventors evaluated the uptake of Cy3 labeled RNAi oligonucleotides by respiratory epithelia in vivo in mice. As shown in FIG. 13, formulating the siRNA with a carboxymethylcellulose viscoelastic gel resulted in significant delivery of the oligonucleotide to the cytoplasm of conducting airway epithelia and to alveolar epithelia.

Example 5

Validation of shRNA to RSV

Figure 17:
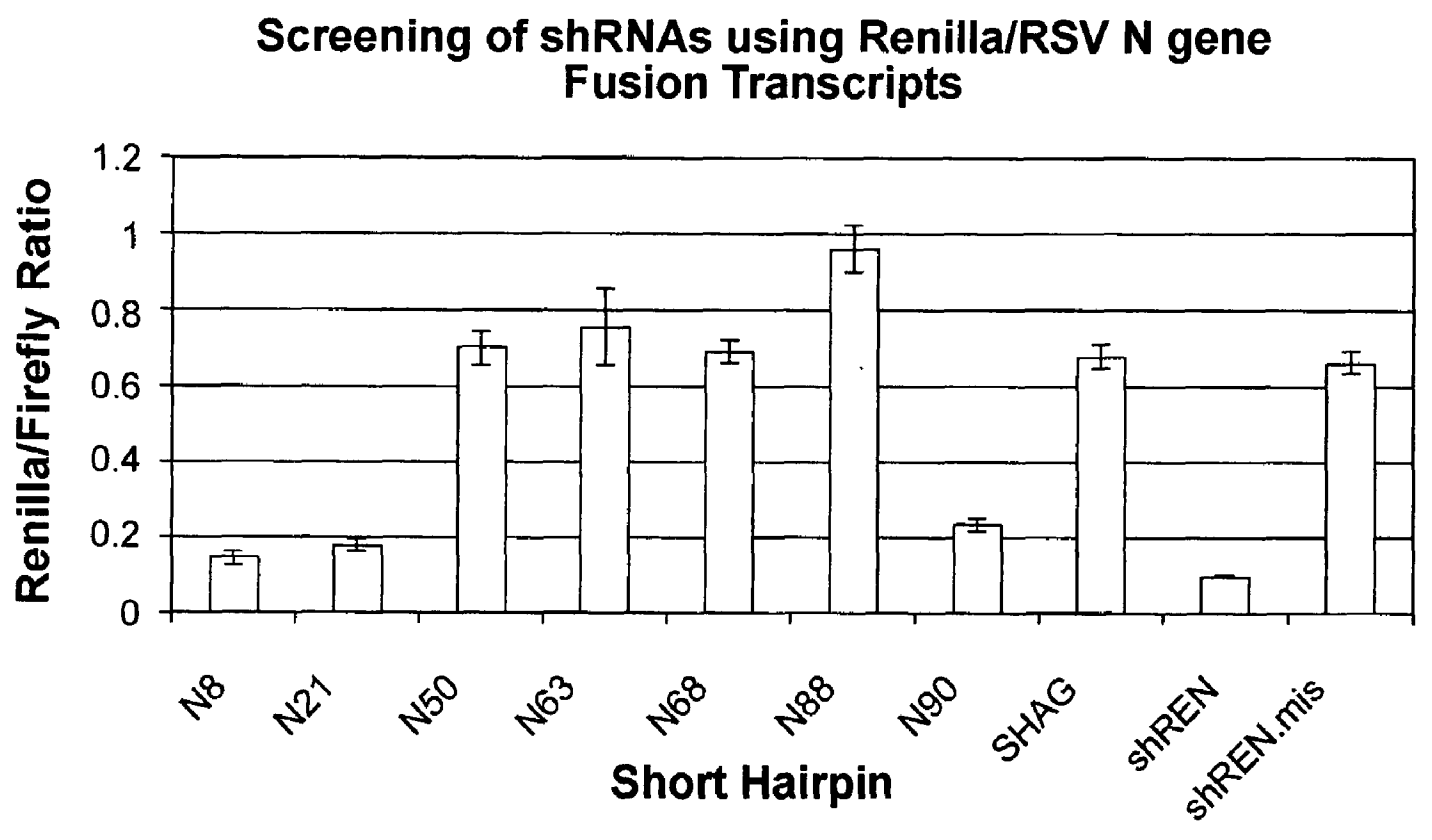

The inventors performed experiments to show the efficacy of the RSV shRNAs in an in vitro assay using a plasmid expressing a fusion transcript of the RSV N gene with renilla luciferase. In this method, luciferase is measured as an indirect assay for N gene product knock down. Briefly, the RSV A2 nucleocapsid cDNA was cloned into psiCheck2 plasmid (Promega), creating Renilla luciferase-nucleocapsid (N) fusion transcript. Firefly luciferase was placed on the same plasmid as an internal control. 293 cells were co-transfected with shRNA plasmid and psiCheck2:N at a 4:1 ratio. Cells were harvested at 48 hrs for dual luciferase assay. The results are shown in FIG. 17. The oligonucleotide shREN is a positive control RNAi targeting the renilla luciferase sequence. This shREN oligonucleotide is a misdirected, negative control RNAi. SHAG is a negative (inactive) control. N8-N90 are shRNAs targeting the N gene product. N8, N21, and N90 caused significant knockdown of the N gene in this assay.

Example 6

RSV Knockdown Post-infection

In this example, the inventors demonstrated that the addition of siRNA 27-mer oligonucleotides to epithelia after viral infection begins caused knockdown of RSV proteins.

Briefly, A549 cells were infected with RSV A2 (MOI=1). Four hours later cells were transfected with indicated 27-mer siRNAs (doses 100 nM to 1 nM) using lipofectamine 2000. The 27-mer oligonucleotides used in this study are shown in FIG. 14B. The RSV mRNA targets included the phosphoprotein gene (P-26), nucleocapsid gene (N-847), and long polymerase (L-1647). Seventy-two hours later, A549 cells were harvested and processed for western blot. Beta-tubulin (tub) was used as a control for protein loading.

Figure 18:
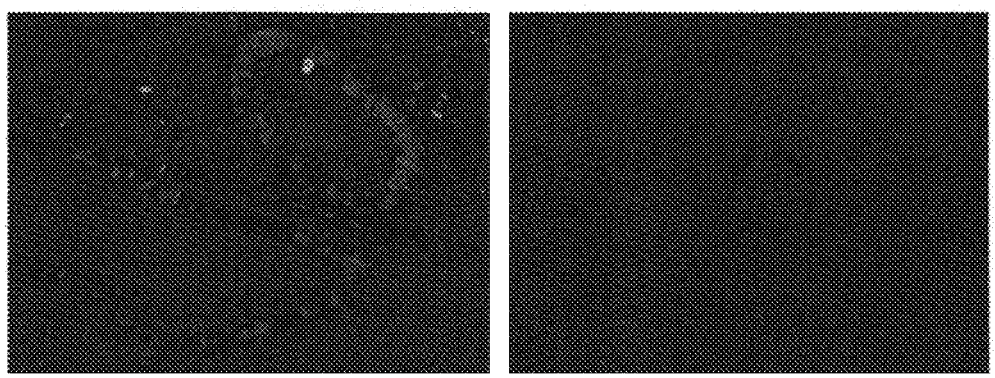
FIG. 18 shows that 27-mer siRNA oligonucleotides applied after RSV infection of A549 cells inhibit viral protein production.

The inventors compared the gene-specific oligonucleotides to findings with a non-specific control oligonucleotide (siGFP) and mock infected control cells (FIG. 18). A dose-dependent knockdown of all RSV targets was observed.

These data suggest that it is possible to have a beneficial effect on the course of a viral infection in airway epithelia, even if the siRNA oligonucleotide is added after the cells are infected. In addition, the data suggest that the possibility of using one or more efficacious oligonucleotides simultaneously as a therapeutic cocktail.

Example 7

Delivery of RNAi oligonucleotides to Mouse Respiratory epithelia In Vivo

Figure 19:
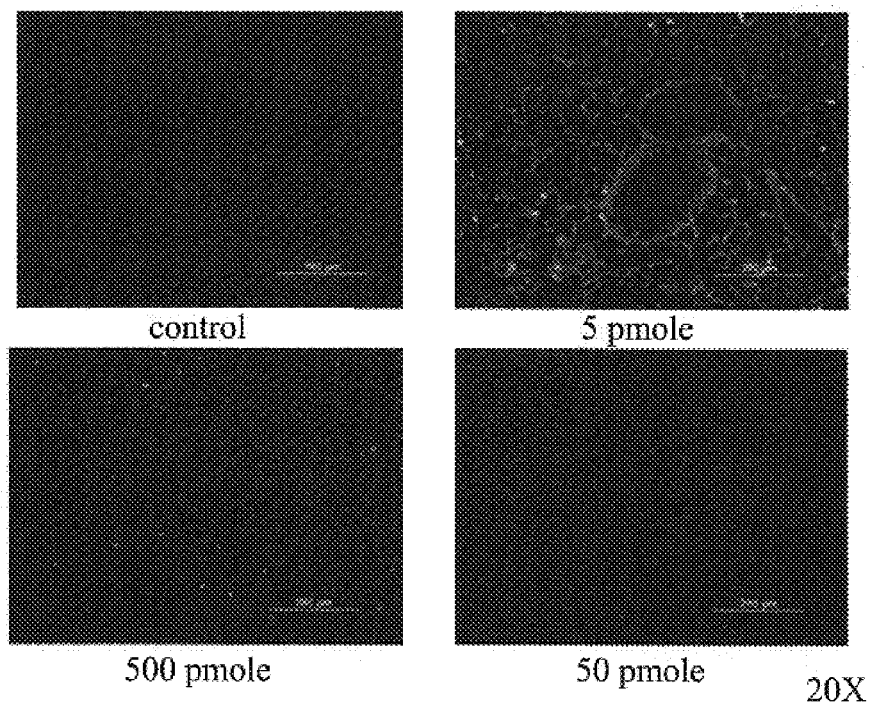
FIG. 19 demonstrates that Cy3 fluorescently labeled oligonucleotides are taken into the epithelial cells of the lung. Naked oligonucleotides at the indicated molar amounts were introduced into mouse lung by direct tracheal instillation. Tissues were examined by microscopy 4 hrs later. The uptake of fluorescent oligonucleotides in respiratory epithelia of the airways and alveolar regions is especially apparent at the highest concentrations.

The delivery of RNAi oligonucleotides to mouse respiratory epithelia in vivo was also studied. BALB/C mice received 50 microliters of Cy3 labeled siRNA oligonucleotide at the indicated concentrations (5 nmole, 500 pmole, 50 pmole) by direct tracheal intubation. Four hours later the animals were killed and the uptake of labeled oligonucleotide in respiratory epithelia was assessed in frozen sections under fluorescence microscopy. Control mice receive PBS only and show only background autofluorescence. FIG. 19 demonstrates that unformulated ('naked") oligonucleotides are also taken up by respiratory epithelia in a dose-dependent fashion. The photographs were all taken with 1/10 second exposure.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

CITATIONS

U.S. Pat. No. 6,593,130
U.S. patent application Ser. No. 09/448,613
PCT/WO95/03357
U.S. Patent Publication No. 2004/0203145 A1
U.S. Patent Publication No. 2005/0054598 A1
U.S. Pat. No. 5,705,188,
PCT International Application WO 97/30731
U.S. Pat. No. 5,350,674
U.S. Pat. No. 5,585,362.

Altschul et al., JMB, 215, 403 (1990).
Amarzguioui et al., Biochem Biophys Res Commun., 316(4):1050-8 (2004).
Bitko et al., BMC Microbiology 1:34 (2001).
Bitko et al., Nat. Med. 11:50-55 (2005).
Bondensgaard et al., Chemistry 6:2687-2695 (2000).
Braasch et al., Chem Biol. 8:1-7 (2001).
Cao et al., Cell Res. 15:111-119 (2005).
Carmichael et al., Nature, 418, 379 (2002).
Corpet et al., Nucl. Acids Res., 16, 10881 (1988).
Crinelli et al., Nucl. Acids Res. 30:2435-2443 (2002).
Deng et al., J. Polymer Sci. Part C Polymer letters, 24, 411 (1988).
Elman et al., Nuc. Acids Res. 33:439-447 (2005).
Gref et al., Science, 263, 1600 (1994) Higgins et al., Gene, 73, 237 (1988).
Higgins et al., CABIOS, 5, 151 (1989).
Holen et al., Nucl. Acids Res 30:1757-1766 (2003).
Huang et al., CABIOS, 8, 155 (1992).
Ji et al., FEBS Lett 552:247-252 (2003).
Karlin and Altschul, Proc. Natl. Acad. Sci. USA, 87, 2264 (1990).
Karlin and Altschul, Proc. Natl. Acad. Sci. USA 90, 5873 (1993)
Khvorova et al. Cell 115:209-216 (2003).
Kurreck et al., Nucl. Acids Res. 30:1911-1918 (2002).
Meinkoth and Wahl, Anal. Biochem., 138, 267 (1984).
Miller, et al., Mol. Cell. Biol., 10, 4239 (1990).
Murray, E. J., ed. Methods in Molecular Biology, Vol. 7, Humana Press Inc., Clifton, N.J., (1991).
Myers and Miller, CABIOS, 4, 11 (1988).
Needleman and Wunsch, JMB, 48, 443 (1970).
Pearson et al., Meth. Mol. Biol., 24, 307 (1994).
Pearson and Lipman, Proc. Natl. Acad. Sci. USA, 85, 2444 (1988).
Platz et al., Oligonucleotides 15:132-138 (2005).
Reynolds et al., Nat Biotechnol., 22(3):326-30 (2004).
Scherer et al., Nat. Biotechnology 21:1457-1465 (2003).
Schwarz et al., Cell 115:199-208 (2003).
Seiler et al., Am J. Respir. Cell Mol. Biol. 27:133-140 (2002).
Shah et al., AAPS PharmSci 5(4), R6144 (2003).
Sinn et al. Am J Respir Cell Mol Biol. 32:404-10 (2005).
Smith et al., Adv. Appl. Math., 2, 482 (1981).
Ui-Tei, et al., Nucl. Acids REs 32:936-948 (2004).
Wahlestedt et al., PNAS 97:5633-5638 (2000).
Wang et al., J Clin Invest. 104(11):R55-62 (1999).
Xia et al., Nat. Biotechnol., 19, 640 (2001).
Xia et al., Nat Biotechnol 20, 1006-10 (2002).
Zabner et al., Am J Physiol Lung Cell Mol Physiol. 284(5):L844-54 (2003).
Zhu et al., J. Polym. Sci. Polm. Chem., 27, 2151 (1989)

---

What is claimed is:

1. A precursor RNAi molecule capable of inhibiting the expression of a respiratory syncytial virus (RSV)-specific messenger RNA (mRNA) to which it corresponds comprising:

a first oligonucleotide strand that is 22-30 nucleotides in length; and a second oligonucleotide strand that is 22-30 nucleotides in length and comprises a nucleotide sequence that is sufficiently complementary to a sequence of an RNA of a target gene to direct target-specific RNAi and wherein the second oligonucleotide strand anneals to the first oligonucleotide strand under biological conditions, wherein the first strand of RNA comprises SEQ ID NO:279 and the second strand of RNA comprises SEQ ID NO:280, and wherein the precursor RNAi molecule is a substrate for a Dicer.

2. The precursor RNAi molecule of claim 1, wherein the first and second oligonucleotide strands have a different length and wherein one of the first and second oligonucleotide strands has a 3' overhang that enhances Dicer processing of the precursor RNAi molecule.

3. The precursor RNAi molecule of claim 2, wherein the overhang is one to three nucleotides.

4. The precursor RNAi molecule of claim 2, wherein the overhang is two nucleotides.

5. The precursor RiNAi molecule of claim 1, wherein at least one of the first and second oligonucleotide strands is modified on the 3' end to direct Dicer processing of the RNAi molecule.

6. The precursor RNAi molecule of claim 5, wherein the modification is a deoxyribonucleotide, dideoxyribonucleotide, acyclonucleotide, 3 '-deoxyadeno sine (cordycepin), 3'-azido-3'-deoxythymidine (AZT), 2',3'-dideoxyinosine (ddI), 2',3-dideoxy-3'-thiacytidine (3TC), 2',3'-didehydro-2',3'-dideoxythymidine (d4T), a monophosphate nucleotide of 3'-azido-3'-deoxythymidine (AZT), 2',3'-dideoxy-3'-thiacytidine (3TC) or a monophosphate nucleotide of 2',3'-didehydro-2',3'-dideoxythymidine (d4T).

7. The precursor RNAi molecule of claim 5, wherein the modification is 1-3 deoxynucleotides substituted for ribonucleotides at the 3' end of the first oligonucleotide strand.

8. The precursor RNAi molecule of claim 1, wherein the first and second oligonucleotide strands are linked by a linker, wherein the strands anneal under biological conditions.

9. The precursor RNAi molecule of claim 8, wherein the linker is an oligonucleotide.

10. The precursor RNAi molecule of claim 9, wherein the linker contains 4 to 10 nucleotides.

11. The precursor RiNAi molecule of claim 9, wherein the linker contains 4, 5 or 6 nucleotides.

12. The precursor RNAi molecule of claim 1, wherein a ribonucleotide of the first or second strand is modified.

13. The precursor RNAi molecule of claim 1, wherein a ribonucleotide is substituted by a locked nucleic acid (LNA).

14. The precursor RNAi molecule of claim 13, wherein the LNA is in the 5 'region of the first strand.

15. An isolated or purified expression cassette comprising
a nucleic acid encoding a first oligonucleotide strand that is 22-30 nucleotides in length, wherein the first strand of RNA comprises SEQ ID NO:279;
a second oligonucleotide strand that is 22-30 nucleotides in length, wherein the second strand of RNA comprises SEQ ID NO:280 and comprises a nucleotide sequence that is sufficiently complementary to a seciuence of an RNA of a target gene to direct target-specific RNAi;
an oligonucleotide linker positioned between the first oligonucleotide strand and the second oligonucleotide strand; and
a promoter operably linked to the first oligonucleotide strand.

16. The isolated or purified expression cassette of claim 15, wherein the promoter is a regulatable promoter.

17. The isolated or purified expression cassette of claim 15, wherein the promoter is a constitutive promoter.

18. The isolated or purified expression cassette of claim 17, wherein the promoter is a CMV, RSV, pol II or pol III promoter.

19. The isolated or purified expression cassette of claim 15, wherein the expression cassette further comprises a polyadenylation signal.

20. The isolated or purified expression cassette of claim 15, further comprising a marker gene.

21. An isolated cell comprising the isolated or purified expression cassette of claim 15.

22. The cell of claim 21, wherein the cell is a mammalian cell.

23. A vector comprising the isolated or purified expression cassette of claim 15.

24. The vector of claim 23, wherein the vector is an adenoviral, lentiviral, adeno-associated viral (AAV), poliovirus, Herpes Simplex Virus (HSV), or murine Moloney-based viral vector.

25. The vector of claim 24, wherein the vector is an adenoviral vector.

26. The vector of claim 23, wherein the vector is a plasmid vector.

27. A composition comprising a polymer or excipient and the precursor RNAi molecule of claim 1.

28. The composition of claim 27, wherein the polymer or excipient is bioadhesive, mucoadhesive or viscoelastic.

29. The composition of claim 27, wherein the polymer or excipient is a gel.

30. The composition of claim 29, wherein the gel is a viscoelastic gel.

31. The composition of claim 30, wherein the viscoelastic gel is methylcellulose, carboxymethylcellulose or a poloxamer polymer.

32. The composition of claim 30, wherein the viscoelastic gel is methylcellulose or carboxymethylcellulose.

33. The composition of claim 27, further comprising a calcium chelator.

34. The composition of claim 33, wherein the calcium chelator is ethylene glycol -bis-(2-aminoethyl)-N,N,N', N'-tetraacetic acid (EGTA), ethylenedioxy-diethylene -dinitrilo-tetraacetic acid (EDTA) or 1,2-bis(aminophenoxy) ethane-N,N,N', N'-tetra-acetic acid (BAPTA).

35. The composition of claim 33, wherein the calcium chelator is ethylene glycol -bis-(2-aminoethyl)-N,N,N', N'-tetraacetic acid (EGTA).

36. A vector comprising two expression cassettes,
the first expression cassette comprising a first promoter operably linked to a nucleic acid encoding a first oligonucleotide strand that is 22-30 nucleotides in length, wherein the first oligonucleotide strand comprises SEQ ID NO:279 operably linked to a promoter; and
the second expression cassette comprising a second promoter operably linked to a second oligonucleotide strand that is 22-30 nucleotides in length, wherein the second oligonucleotide strand comprises SEQ ID NO:280 and comprises a nucleotide sequence that is sufficiently complementary to a sequence of an RNA of a target gene to direct target-specific RNAi.

37. The vector of claim 36, wherein the vector is an adenoviral, lentiviral, adeno-associated viral (AAV), poliovirus, HSV, or murine Moloney-based viral vector.

38. The vector of claim 37, wherein the vector is an adenoviral vector.

39. The vector of claim 36, wherein the vector is a plasmid vector.

40. A composition comprising a polymer or excipient and the vector of claim 23.

41. The composition of claim 40, wherein the polymer or excipient is bioadhesive, mucoadhesive or viscoelastic.

42. The composition of claim 40, wherein the polymer or excipient is a gel.

43. The composition of claim 42, wherein the gel is a viscoelastic gel.

44. The composition of claim 43, wherein the viscoelastic gel is methylcellulose, carboxymethylcellulose or a poloxamer polymer.

45. The composition of claim 43, wherein the viscoelastic gel is methylcellulose or carboxymethylcellulose.

46. The composition of claim 40, further comprising a calcium chelator.

47. The composition of claim 46, wherein the calcium chelator is ethylene glycol-bis -(2-aminoethyl)-N,N,N', N'-tetraacetic acid (EGTA), ethylenedioxy-diethylene-dinitrilo -tetraacetic acid (EDTA) or 1,2-bis(aminophenoxy) ethane-N,N,N', N'-tetra-acetic acid (BAPTA).

48. The composition of claim 47, wherein the calcium chelator is ethylene glycol-bis -(2-aminoethyl)-N,N,N', N'-tetraacetic acid (EGTA).

49. A composition comprising a polymer or excipient and the vector of claim 36.

50. The composition of claim 49, wherein the polymer or excipient is bioadhesive, mucoadhesive or viscoelastic.

51. The composition of claim 49, wherein the polymer or excipient is a gel.

52. The composition of claim 51, wherein the gel is a viscoelastic gel.

53. The composition of claim 51, wherein the viscoelastic gel is methylcellulose, carboxymethylcellulose or a poloxamer polymer.

54. The composition of claim 51, wherein the viscoelastic gel is methylcellulose or carboxymethylcellulose.

55. The composition of claim 49, further comprising a calcium chelator.

56. The composition of claim 55, wherein the calcium chelator is ethylene glycol-bis -(2-aminoethyl)-N,N,N', N'-tetraacetic acid (EGTA), ethylenedioxy-diethylene-dinitrilo -tetraacetic acid (EDTA) or 1 ,2-bis(aminophenoxy) ethane-N,N,N', N'-tetra-acetic acid (BAPTA).

57. The composition of claim 55, wherein the calcium chelator is ethylene glycol-bis -(2-aminoethyl)-N,N,N', N'-tetraacetic acid (EGTA).

* * * * *

UNITED STATES PATENT AND TRADEMARK OFFICE
CERTIFICATE OF CORRECTION

| | |
|---|---|
| PATENT NO. | : 7,297,786 B2 |
| APPLICATION NO. | : 11/179848 |
| DATED | : November 20, 2007 |
| INVENTOR(S) | : Paul B. McCray et al. |

It is certified that error appears in the above-identified patent and that said Letters Patent is hereby corrected as shown below:

Title Page;
On page 1, under (54), please change the title to --RNA INTERFERENCE IN RESPIRATORY EPITHELIAL CELLS--.

At Column 1, lines 19-20, please delete "may have" and insert therefor --has--.

Signed and Sealed this

Twelfth Day of August, 2008

JON W. DUDAS
*Director of the United States Patent and Trademark Office*

UNITED STATES PATENT AND TRADEMARK OFFICE
CERTIFICATE OF CORRECTION

PATENT NO. : 7,297,786 B2                                                                            Page 1 of 1
APPLICATION NO. : 11/179848
DATED : November 20, 2007
INVENTOR(S) : Paul B. McCray et al.

It is certified that error appears in the above-identified patent and that said Letters Patent is hereby corrected as shown below:

Title Page;
On page 1, under (54), and Column 1, lines 1 and 2, please change the title to --RNA INTERFERENCE IN RESPIRATORY EPITHELIAL CELLS--.

At Column 1, lines 19-20, please delete "may have" and insert therefor --has--.

This certificate supersedes the Certificate of Correction issued August 12, 2008.

Signed and Sealed this

Sixteenth Day of September, 2008

JON W. DUDAS
*Director of the United States Patent and Trademark Office*

SEQUENCE LISTING

<160> NUMBER OF SEQ ID NOS: 331

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aagccaacca acctcgatct c                                          21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ttgtagatct gttctctaaa c                                          21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtgtagctgt cgctcggctg c                                          21

<210> SEQ ID NO 4

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcggctgcat gcctagtgca c                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtgcacctac gcagtataaa c                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonuleotide

<400> SEQUENCE: 6
ttgacaagaa acgagtaact c                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tcgtccgtgt tgcagtcgat c                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
taggtttcgt ccgggtgtga c                                              21

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tatagtgagt cgtatta                                                   17

<210> SEQ ID NO 10
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aagagatcga ggttggttgg c                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tcgtttagag aacagatcta c                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
atgcagccga gcgacagcta c                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aggtgcacta ggcatgcagc c                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ttgtttatac tgcgtaggtg c                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
acgagttact cgtttcttgt c                                              21

<210> SEQ ID NO 16
<211> LENGTH: 21
<212> TYPE: DNA
```

<213> ORGANISM: Artificial Sequence
<220> FEATURE:
<223> OTHER INFORMATION: Description of Artificial Sequence: Synthetic
oligonucleotide

<400> SEQUENCE: 16
atgatcgact gcaacacgga c                                    21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 17
cggtcacacc cggacgaaac c                                    21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 18
tcggctgcat gcctagtgca c                                    21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
cagactgctt acggtttcgt c                                    21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20
ccgaaaggta agatggagag c                                    21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
aggttagaga cgtgctagtg c                                    21

<210> SEQ ID NO 22
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 22
tcggaggcac gtgaacacct c                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ctgccccagc ttgaacagcc c                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gagctggttg cagaaatgga c                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ttgcataccg caatgttctt c                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aagtcttatg acttaggtga c                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aagcatggca gtggtgcact c                                              21

<210> SEQ ID NO 28
<211> LENGTH: 21
<212> TYPE: DNA
<213> ORGANISM: Artificial Sequence
<220> FEATURE:
```

<223> OTHER INFORMATION: Description of Artificial Sequence: Synthetic
     oligonucleotide

<400> SEQUENCE: 28
aggtgcacta ggcatgcagc c                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 29
cggacgaaac cgtaagcagt c                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 30
aggctctcca tcttaccttt c                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 31
acgcactagc acgtctctaa c                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 32
ttgaggtgtt cacgtgcctc c                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 33
tagggctgtt caagctgggg c                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34
ccgtccattt ctgcaaccag c                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
aagaagaaca ttgcggtatg c                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tcgtcaccta agtcataaga c                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cggagtgcac cactgccatg c                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
aagtgcagcc cgtcttacac c                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
caggagaagg atgaggaagg c                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 40
gagtagatgg tgacatggta c                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gtgatacatt aaaagaaata c                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
aggtgagcgt gtacgccaat c                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tggtacgatt tcggtgattt c                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
agggcattgg ctgctgagtc c                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tgggaccaga cataccatcc c                                              21

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 46
ggtgttcctt tgttgtttc                                              20

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
atgctgctga tccagctatg c                                           21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
aggaaggaag ttctgttgaa c                                           21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gtggctgtat taatgccaac c                                           21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
atgtcatccc tactataact c                                           21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ctggcataat atgttaaaaa c                                           21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
```

```
tggcctctct tgttcttgct c                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gagatggtca tgtgtggcgg c                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ctgacaagta tgtccgcaat c                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
atgattcttt ctgatgatgc c                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ctgaccttac taaaggacct c                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ttgtcaaaac agatggtaca c                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
```
tggacatgta ttccgtaatg c                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
atgtacacac cacatacagt c                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
acggtgtaag acgggctgca c                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ttgccttcct catccttctc c                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tggtaccatg tcaccatcta c                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gagtatttct tttaatgtat c                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
atgattggcg tacacgctca c                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 65
acgaaatcac cgaaatcgta c                                          21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 66
tgggactcag cagccaatgc c                                          21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 67
ttgggatggt atgtctggtc c                                          21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 68
ttgaaacaac aaaggaaca c                                           21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 69
atgcatagct ggatcagcag c                                          21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 70
tagttcaaca gaacttcctt c                                          21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 71
ttggttggca ttaatacagc c                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 72
ttgagttata gtagggatga c                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 73 cagttttaa catattatgc c                                               21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 74
gcgagcaaga acaagagagg c                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 75
gagccgccac acatgaccat c                                              21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 76
tagattgcgg acatacttgt c                                              21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
acggcatcat cagaaagaat c                                              21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gtgaggtcct ttagtaaggt c                                              21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
aagtgtacca tctgttttga c                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tagcattacg gaatacatgt c                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
aagactgtat gtggtgtgta c                                              21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tagtgacctt gaccggtgca c                                              21

<210> SEQ ID NO 83

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cagggtttca tactattaat c                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gtgtgacaac cctttctttg c                                              21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
caggtaattt taaacactta c                                              21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
aagttgcctc ttggtattaa c                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ctgttgattg ttctcaaaat c                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
atgggagaga aaaaaaattt c                                              21

<210> SEQ ID NO 89
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ttgcttctcc aatgtctatg c                                           21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
atgatttcat gggttgtgtc c                                           21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gagagacata tctaatgtgc c                                           21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ttgtagtact ttcttttgaa c                                           21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ccgtgatgtt tctgatttca c                                           21

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ctgatgtttc tacagcaatt c                                           21

<210> SEQ ID NO 95
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 95
ctggcatttg tgctagttac c                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ctgaatgtgc taatttgctt c                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gtgacactcg ctgatgctgg c                                              21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
atggacattt ggtgctggcg c                                              21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
aagctgcaag acgttgttaa c                                              21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gaggcggagg tacaaattga c                                              21

<210> SEQ ID NO 101
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 101
atgtccttcc cacaagcagc c                                              21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
atgaaggcaa agcatacttc c                                              21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
atgatcctct gcaacctgag c                                              21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tggtatgttt ggctcggctt c                                              21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gggtgtcaaa ttacattaca c                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tggtgcaccg gtcaaggtca c                                              21

<210> SEQ ID NO 107
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 107
atgattaata gtatgaaacc c                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
cagcaaagaa agggttgtca c                                              21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
tcgtaagtgt ttaaaattac c                                              21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
atgttaatac caagaggcaa c                                              21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tggattttga gaacaatcaa c                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tagaaatttt ttttctctcc c                                              21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 113
ctgcatagac attggagaag c                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
aaggacacaa cccatgaaat c                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
aaggcacatt agatatgtct c                                              21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
aagttcaaaa gaaagtacta c                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cagtgaaatc agaaacatca c                                              21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
atgaattgct gtagaaacat c                                              21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 119
atggtaacta gcacaaatgc c                                              21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gagaagcaaa ttagcacatt c                                              21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
aagccagcat cagcgagtgt c                                              21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
cagcgccagc accaaatgtc c                                              21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tggttaacaa cgtcttgcag c                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ctgtcaattt gtacctccgc c                                              21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 125 gggggctgctt gtgggaagga c                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
agggaagtat gctttgcctt c                                               21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
aagctcaggt tgcagaggat c                                               21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
atgaagccga gccaaacata c                                               21

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
atgtgtaatg taatttgaca c                                               21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
atggacccca atcaaaccaa c                                               21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
```
gcgccgaccc caaggtttac c                                              21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
atgaccaaat tggctactac c                                              21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
aggaactggc ccagaagctt c                                              21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
atgctgccac cgtgctacaa c                                              21

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
cggtaattca agaaattcaa c                                              21

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
aagtttctgg taaaggccaa c                                              21

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137

```
aagcatttgg gagacgtggt c                                             21
```

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138

```
tggcatggaa gtcacacctt c                                             21
```

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139

```
ctgatgaagc tcagcctttg c                                             21
```

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140

```
tggatgattt ctccagacaa c                                             21
```

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141

```
gagcttctgc tgattcaact c                                             21
```

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142

```
acgttggttt gattggggtc c                                             21
```

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143

```
tgggtaaacc ttggggtcgg c                                             21
```

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
tcggtagtag ccaatttggt c                                              21

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gtgaagcttc tgggccagtt c                                              21

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
aagttgtagc acggtggcag c                                              21

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
gagttgaatt tcttgaatta c                                              21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ttgttggcct ttaccagaaa c                                              21

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
tggaccacgt ctcccaaatg c                                              21

```
<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
ccgaaggtgt gacttccatg c                                          21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
cggcaaaggc tgagcttcat c                                          21

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
aagttgtctg gagaaatcat c                                          21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ctgagttgaa tcagcagaag c                                          21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
atggacccca atcaaaccaa c                                          21

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
ccgcattaca tttggtggac c                                          21
```

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
gaggacgcaa tggggcaagg c                                              21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
aggtttaccc aataatactg c                                              21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
cagggcgttc caatcaacac c                                              21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
atgaccaaat tggctactac c                                              21

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
acgttggttt gattggggtc c                                              21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
tgggtccacc aaatgtaatg c                                              21

<210> SEQ ID NO 162

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
tggccttgcc ccattgcgtc c                                             21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
acgcagtatt attgggtaaa c                                             21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ttggtgttga ttggaacgcc c                                             21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
tcggtagtag ccaatttggt c                                             21

<210> SEQ ID NO 166
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
ctcgagaaaa aa                                                       12

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
aagttacata ttcaatggtc c                                             21

<210> SEQ ID NO 168
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
aatgcaacat cctccatcat g                                              21

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
aactgcatgg tgtacaatct c                                              21

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
aacggtgtat attacccagc t                                              21

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
aacagatatt gatagagcca c                                              21

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
aattccctgc atcaatacca g                                              21

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
aaagagtgtt gttagtggag a                                              21

<210> SEQ ID NO 174
<211> LENGTH: 10
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 174
tgacaggaag                                                          10

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ggaccattga atatgtaact t                                             21

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
catgatggag gatgttgcat t                                             21

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gagattgtac accatgcagt t                                             21

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
agctgggtaa tatacaccgt t                                             21

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
gtggctctat caatatctgt t                                             21

<210> SEQ ID NO 180
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 180
ctggtattga tgcagggaat t                                             21

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
tctccactaa caacactctt t                                             21

<210> SEQ ID NO 182
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
caaaacaagg cttttctcca agg                                           23

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
aacggagcac aggagatagt a                                             21

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
aaatactcag agatgcggga t                                             21

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
aatacaggca tgactctcct g                                             21

<210> SEQ ID NO 186
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 186
aaggacatag ccaacagctt c                                              21

<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
aatcttctac cagaggtggc a                                              21

<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
aatttcctca cttctccagt g                                              21

<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
aatgggagag tacagaggta c                                              21

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
tactatctcc tgtgctccgt t                                              21

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
atcccgcatc tctgagtatt t                                              21

<210> SEQ ID NO 192
<211> LENGTH: 21
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 192
caggagagtc atgcctgtat t                                              21

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
gaagctgttg gctatgtcct t                                              21

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
tgccacctct ggtagaagat t                                              21

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
cactggagaa gtgaggaaat t                                              21

<210> SEQ ID NO 196
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
gtacctctgt actctcccat t                                              21

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
aacgataata taacagcaag a                                              21

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 198
tcttgctgtt atattatcgt t                                              21

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
aggctttagt tggaattttg c                                              21

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
gagatttggc gccttggtgc c                                              21

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
tggcttgaca aggatctagt c                                              21

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
tggaagagcc agtcatttgt c                                              21

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
aagcaaaatt ccaactaaag c                                              21

<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 204
acggcaccaa ggcgccaaat c                                              21

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
aagactagat ccttgtcaag c                                              21

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
aagacaaatg actggctctt c                                              21

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
tggcctgcaa ccgtgtgaca c                                              21

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
ctgttctact attgcgcaag c                                              21

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
gggtctgcat ggcaatcaga c                                              21

<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
gaggaatttg atgttgtctt c                                                    21

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
aagtgtcaca cggttgcagg c                                                    21

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
cggcttgcgc aatagtagaa c                                                    21

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
acgtctgatt gccatgcaga c                                                    21

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
ccgaagacaa catcaaattc c                                                    21

<210> SEQ ID NO 215
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
tagaaaagtt gctttttaga c                                                    21

<210> SEQ ID NO 216
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
tggaagcaag tgctgtgtgt c        21

<210> SEQ ID NO 217
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
ttggcttact aagcgtaagc c        21

<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
ttgatggtga ctatgctatg c        21

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
ttggttacca agagttaagt c        21

<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
ttgttgcttt gtcactctgt c        21

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
tggatttgtg cttcgctctg c        21

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
gtgttacact tgggtgctgg c        21

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
aagtctaaaa agcaactttt c                                              21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
aggacacaca gcacttgctt c                                              21

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
agggcttacg cttagtaagc c                                              21

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
ctgcatagca tagtcaccat c                                              21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
ttgacttaac tcttggtaac c                                              21

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
aagacagagt gacaaagcaa c                                              21

```
<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
acgcagagcg aagcacaaat c                                              21

<210> SEQ ID NO 230
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
gagccagcac ccaagtgtaa c                                              21

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
tagaaaagtt gcttttaga c                                               21

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
atgggctgat gcatctgaac c                                              21

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
gtgacagaaa ccataacagt c                                              21

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
ctgtgcccaa agaccatcca c                                              21
```

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 235
ttgctactat gttactgaac c                                              21

<210> SEQ ID NO 236
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 236
aagtctaaaa agcaactttt c                                              21

<210> SEQ ID NO 237
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 237
gtggttcaga tgcatcagcc c                                              21

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 238
ctgactgtta tggtttctgt c                                              21

<210> SEQ ID NO 239
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 239
gtgtggatgg tctttgggca c                                              21

<210> SEQ ID NO 240
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 240
taggttcagt aacatagtag c                                              21

<210> SEQ ID NO 241

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
tagaaaagtt gcttttttaga c                                         21

<210> SEQ ID NO 242
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
tcgtagtgta attgaaattt c                                          21

<210> SEQ ID NO 243
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
gagattccat tctacaaacg c                                          21

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
aagtctaaaa agcaactttt c                                          21

<210> SEQ ID NO 245
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
atgaaatttc aattacacta c                                          21

<210> SEQ ID NO 246
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
aggcgtttgt agaatggaat c                                          21

<210> SEQ ID NO 247
<211> LENGTH: 1666
```

```
<212> TYPE: DNA
<213> ORGANISM: Homo sapiens

<400> SEQUENCE: 247
ctccataagg cacaaacttt cagagacagc agagcacaca agcttctagg acaagagcca       60
ggaagaaacc accggaagga accatctcac tgtgtgtaaa catgacttcc aagctggccg      120
tggctctctt ggcagccttc ctgatttctg cagctctgtg tgaaggtgca gttttgccaa      180
ggagtgctaa agaacttaga tgtcagtgca taaagacata ctccaaacct ttccacccca      240
aatttatcaa agaactgaga gtgattgaga gtggaccaca ctgcgccaac acagaaatta      300
ttgtaaagct ttctgatgga agagagctct gtctggaccc caaggaaaac tgggtgcaga      360
gggttgtgga gaagttttg aagagggctg agaattcata aaaaaattca ttctctgtgg       420
tatccaagaa tcagtgaaga tgccagtgaa acttcaagca aatctacttc aacacttcat      480
gtattgtgtg ggtctgttgt agggttgcca gatgcaatac aagattcctg gttaaatttg      540
aatttcagta acaatgaat agttttttcat tgtaccatga aatatccaga acatacttat       600
atgtaaagta ttatttattt gaatctacaa aaaacaacaa ataattttta aatataagga      660
ttttcctaga tattgcacgg gagaatatac aaatagcaaa attgaggcca agggccaaga      720
gaatatccga actttaattt caggaattga atgggtttgc tagaatgtga tatttgaagc      780
atcacataaa aatgatggga caataaattt tgccataaag tcaaatttag ctggaaatcc      840
tggatttttt tctgttaaat ctggcaaccc tagtctgcta gccaggatcc acaagtcctt      900
gttccactgt gccttggttt ctcctttatt tctaagtgga aaaagtatta gccaccatct      960
tacctcacag tgatgttgtg aggacatgtg gaagcacttt aagttttttc atcataacat     1020
aaattatttt caagtgtaac ttattaacct atttattatt tatgtattta tttaagcatc     1080
aaatatttgt gcaagaattt ggaaaaatag aagatgaatc attgattgaa tagttataaa     1140
gatgttatag taaatttatt ttatttaga tattaaatga tgttttatta gataaatttc      1200
aatcagggtt tttagattaa acaaacaaac aattgggtac ccagtaaat tttcatttca      1260
gataaacaac aaataatttt ttagtataag tacattattg tttatctgaa attttaattg     1320
aactaacaat cctagtttga tactcccagt cttgtcattg ccagctgtgt tggtagtgct     1380
gtgttgaatt acggaataat gagttagaac tattaaaaca gccaaaactc cacagtcaat     1440
attagtaatt tcttgctggt tgaaacttgt ttattatgta caaatagatt cttataatat     1500
tatttaaatg actgcatttt taaatacaag gctttatatt tttaaccttta agatgttttt    1560
atgtgctctc caaattttttt ttactgtttc tgattgtatg gaaatataaa agtaaatatg    1620
aaacatttaa aatataattt gttgtcaaag taaaaaaaaa aaaaaa                    1666

<210> SEQ ID NO 248
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
gcagttttgc caaggagtgc taaagaactt agatgtcagt g                          41

<210> SEQ ID NO 249
<211> LENGTH: 25
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 249
ccaaggagug cuaaagaacu uagat                                    25

<210> SEQ ID NO 250
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 250
aucuaaguuc uuuagcacuc cuuggca                                  27

<210> SEQ ID NO 251
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
aagggccaag agaatatccg aactttaatt tcaggaattg a                  41

<210> SEQ ID NO 252
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 252
gagaauaucc gaacuuuaau uucag                                    25

<210> SEQ ID NO 253
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 253
cugaaauuaa aguucggaua uucucuu                                  27

<210> SEQ ID NO 254
<211> LENGTH: 41
<212> TYPE: DNA
<213> ORGANISM: Artificial Sequence
<220> FEATURE:
<223> OTHER INFORMATION: Description of Artificial Sequence: Synthetic
```

-continued

```
                  oligonucleotide

<400> SEQUENCE: 254
gtctgctagc caggatccac aagtccttgt tccactgtgc c                41

<210> SEQ ID NO 255
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 255
ccaggaucca caaguccuug uucca                                  25

<210> SEQ ID NO 256
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 256
uggaacaagg acuuguggau ccuggcu                                27

<210> SEQ ID NO 257
<211> LENGTH: 420
<212> TYPE: DNA
<213> ORGANISM: Human respiratory syncytial virus

<400> SEQUENCE: 257
atgggcagca attcattgag tatgataaaa gttagattac aaaatttgtt t

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 259
ggcagcaauu cauugaguau gauaa                                           25

<210> SEQ ID NO 260
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 260
uuaucauacu caaugaauug cugccca                                         27

<210> SEQ ID NO 261
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
tacatacaat caaattgaat ggcattgtgt ttgtgc                               36

<210> SEQ ID NO 262
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 262
caaucaaauu gaauggcauu gugtt                                           25

<210> SEQ ID NO 263
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 263
aacacaaugc cauucaauuu gauugua                                         27

<210> SEQ ID NO 264
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 264
aaaaaactaa gtgattcaac aatgaccaat tatat                       35

<210> SEQ ID NO 265
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 265
cuaagugauu caacaaugac caatt                                  25

<210> SEQ ID NO 266
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 266
aauuggucau uguugaauca cuuaguu                                27

<210> SEQ ID NO 267
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ttatctgaat tacttggatt tgatcttaat ccata                       35

<210> SEQ ID NO 268
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 268
gaauuacuug gauuugaucu uaatc                                  25

<210> SEQ ID NO 269
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 269
gauuaagauc aaauccaagu aauucuu                                27

<210> SEQ ID NO 270
<211> LENGTH: 375
<212> TYPE: DNA
<213> ORGANISM: Human respiratory syncytial virus

<400> SEQUENCE: 270
atggacacaa cccacaatga taatacacca caaagactga tgatcacaga catgagaccg      60
ttgtcacttg agaccataat aacatcacta accagagaca tcataacaca caaatttata    120
tacttgataa atcatgaatg catagtgaga aaacttgatg aaagacaggc cacatttaca    180
ttcctggtca actatgaaat gaaactatta cacaaagtag gaagcactaa atataaaaaa    240
tatactgaat acaacacaaa atatggcact ttccctatgc caatattcat caatcatgat    300
gggttcttag aatgcattgg cattaagcct acaaagcata ctcccataat atacaagtat    360
gatctcaatc cataa                                                     375

<210> SEQ ID NO 271
<211> LENGTH: 1176
<212> TYPE: DNA
<213> ORGANISM: Human respiratory syncytial virus

<400> SEQUENCE: 271
atggctctta gcaaagtcaa gttgaatgat acactcaaca aagatcaact tctgtcatcc 60
agcaaataca ccatccaacg gagcacagga gatagtattg atactcctaa ttatgatgtg 120
cagaaacaca tcaataagtt atgtggcatg ttattaatca cagaagatgc taatcataaa 180
ttcactgggt taataggtat gttatatgcg atgtctaggt taggaagaga agacaccata 240
aaaatactca gagatgcggg atatcatgta aaagcaaatg gagtagatgt aacaacacat 300
cgtcaagaca ttaatggaaa agaaatgaaa tttgaagtgt taacattggc aagcttaaca 360
actgaaattc aaatcaacat tgagatagaa tctagaaaat cctacaaaaa aatgctaaaa 420
gaaatgggag aggtagctcc agaatacagg catgactctc ctgattgtgg gatgataata 480
ttatgtatag cagcattagt aataactaaa ttagcagcag gggacagatc tggtcttaca 540
gccgtgatta ggagagctaa taatgtccta aaaaatgaaa tgaaacgtta caaaggctta 600
ctacccaagg acatagccaa cagcttctat gaagtgtttg aaaaacatcc ccactttata 660
gatgtttttg ttcattttgg tatagcacaa tcttctacca gaggtggcag tagagttgaa 720
gggatttttg caggattgtt tatgaatgcc tatggtgcag ggcaagtgat gttacggtgg 780
ggagtcttag caaaatcaat taaaaatatt atgttaggac atgctagtgt gcaagcagaa 840
atggaacaag ttgttgaggt ttatgaatat gcccaaaaat tgggtggtga agcaggattc 900
taccatatat tgaacaaccc aaaagcatca ttattatctt tgactcaatt tcctcacttc 960
tccagtgtag tattaggcaa tgctgctggc ctaggcataa tgggagagta cagaggtaca 1020
ccgaggaatc aagatctata tgatgcagca aaggcatatg ctgaacaact caaagaaaat 1080
ggtgtgatta actacagtgt actagacttg acagcagaag aactagaggc tatcaaacat 1140
cagcttaatc caaaagataa tgatgtagag ctttga 1176

<210> SEQ ID NO 272
<211> LENGTH: 40
<212> TYPE: DNA
<213> ORGANISM: Artificial Sequence
<220> FEATURE:

-continued

<223> OTHER INFORMATION: Description of Artificial Sequence: Synthetic
      oligonucleotide

<400> SEQUENCE: 272
atacaggcat gactctcctg attgtgggat gataatatta                              40

<210> SEQ ID NO 273
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 273
gcaugacucu ccugauugug ggatg                                              25

<210> SEQ ID NO 274
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 274
caucccacaa ucaggagagu caugccu                                            27

<210> SEQ ID NO 275
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
tacaaaggct tactacccaa ggacatagcc aacagcttct a                            41

<210> SEQ ID NO 276
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 276
ggcuuacuac ccaaggacau agcca                                              25

<210> SEQ ID NO 277
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide -continued

<400> SEQUENCE: 277
uggcuauguc cuugggaugu aagccuu 27

<210> SEQ ID NO 278
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 278
agaaatggaa caagttgttg aggtttatga atatgcccaa a 41

<210> SEQ ID NO 279
<211> LENGTH: 25
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 279
ggaacaaguu guugagguuu augaa 25

<210> SEQ ID NO 280
<211> LENGTH: 27
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 280
uucauaaacc ucaacaacuu guuccau 27

<210> SEQ ID NO 281
<211> LENGTH: 726
<212> TYPE: DNA
<213> ORGANISM: Human respiratory syncytial virus

<400> SEQUENCE: 281
atggaaaagt ttgctcctga attccatgga gaagatgcaa acaacagggc tactaaattc 60
ctagaatcaa taaagggcaa attcacatca cccaaagatc ccaagaaaaa agatagtatc 120
atatctgtca actcaataga tatagaagta accaaagaaa gccctataac atcaaattca 180
actattatca acccaacaaa tgagacagat gatactgcag ggaacaagcc caattatcaa 240
agaaaacctc tagtaagttt caaagaagac cctacaccaa gtgataatcc cttttctaaa 300
ctatacaaag aaaccataga aacatttgat aacaatgaag aagaatccag ctattcatac 360
gaagaaataa atgatcagac aaacgataat ataacagcaa gattagatag gattgatgaa 420
aaattaagtg aaatactagg aatgcttcac acattagtag tggcaagtgc aggacctaca 480
tctgctcggg atggtataag agatgccatg gttggtttaa gagaagaaat gatagaaaaa 540
atcagaactg aagcattaat gaccaatgac agattagaag ctatggcaag actcaggaat 600
gaggaaagtg aaaagatggc aaaagacaca tcagatgaag tgtctctcaa tccaacatca 660

```
gagaaattga acaacctatt ggaagggaat gatagtgaca atgatctatc acttgaagat      720
ttctga                                                                 726
```

<210> SEQ ID NO 282
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282

```
ttccatggag aagatgcaaa caacagggct actaaa                                 36
```

<210> SEQ ID NO 283
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 283

```
ggagaagaug caaacaacag ggcta                                             25
```

<210> SEQ ID NO 284
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 284

```
augcccuguu guuugcaucu ucuccau                                           27
```

<210> SEQ ID NO 285
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285

```
aaagaagacc ctacaccaag tgataatccc ttttc                                  35
```

<210> SEQ ID NO 286
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 286

```
gacccuacac caagugauaa uccct                                             25
```

```
<210> SEQ ID NO 287
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 287
agggauuauc acuggugua gggucuu                                          27

<210> SEQ ID NO 288
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
gacaaacgat aatataacag caagattaga tagga                                35

<210> SEQ ID NO 289
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 289
cgauaauaua acagcaagau uagat                                           25

<210> SEQ ID NO 290
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 290
aucuaaucuu gcuguuauau uaucguu                                         27

<210> SEQ ID NO 291
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
actgaagcat taatgaccaa tgacagatta gaag                                 34

<210> SEQ ID NO 292
<211> LENGTH: 25
<212> TYPE: DNA
<213> ORGANISM: Artificial Sequence
```

-continued

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<400> SEQUENCE: 292
gcauuaauga ccaaugacag auuag 25

<210> SEQ ID NO 293
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<400> SEQUENCE: 293
cuaaucuguc auuggucauu aaugcuu 27

<210> SEQ ID NO 294
<211> LENGTH: 6498
<212> TYPE: DNA
<213> ORGANISM: Human respiratory syncytial virus
<400> SEQUENCE: 294
atggatccca ttattaatgg aaattctgct aatgtttatc taaccgatag ttatttaaaa 60
ggtgttatct ctttctcaga gtgtaatgct ttaggaagtt acatattcaa tggtccttat 120
ctcaaaaatg attataccaa cttaattagt agacaaaatc cattaataga acacatgaat 180
ctaaagaaac taaatataac acagtcctta atatctaagt atcataaagg tgaaataaaa 240
ttagaagaac ctacttattt tcagtcatta cttatgacat acaagagtat gacctcgtca 300
gaacagattg ctaccactaa tttacttaaa aagataataa gaagagctat agaaataagt 360
gatgtcaaag tctatgctat attgaataaa ctagggctta aagaaaagga caagattaaa 420
tccaacaatg gacaagatga agacaactca gttattacga ccataatcaa agatgatata 480
ctttcagctg ttaaagataa tcaatctcat cttaaagcag acaaaaatca ctctacaaaa 540
caaaaagaca caatcaaaac aacactcttg aagaaattga tgtgttcaat gcaacatcct 600
ccatcatggt taatacattg gtttaactta tacacaaaat taaacaacat attaacacag 660
tatcgatcaa atgaggtaaa aaaccatggg tttacattga tagataatca aactcttagt 720
ggatttcaat ttattttgaa ccaatatggt tgtatagttt atcataagga actcaaaaga 780
attactgtga caacctataa tcaattcttg acatggaaag atattagcct tagtagatta 840
aatgtttgtt taattacatg gattagtaac tgcttgaaca cattaaataa aagcttaggc 900
ttaagatgcg gattcaataa tgttatcttg acacaactat tcctttatgg agattatata 960
ctaaagctat ttcacaatga ggggttctac ataataaaag aggtagaggg atttattatg 1020
tctctaattt taaatataac agaagaagat caattcagaa aacgatttta taatagtatg 1080
ctcaacaaca tcacagatgc tgctaataaa gctcagaaaa atctgctatc aagagtatgt 1140
catacattat tagataagac agtgtccgat aatataataa atggcagatg gataattcta 1200
ttaagtaagt tccttaaatt aattaagctt gcaggtgaca ataaccttaa caatctgagt 1260
gaactatatt ttttgttcag aatatttgga cacccaatgg tagatgaaag acaagccatg 1320

-continued

```
gatgctgtta aaattaattg caatgagacc aaattttact tgttaagcag tctgagtatg    1380
ttaagaggtg cctttatata tagaattata aagggtttg taaataatta caacagatgg    1440
cctactttaa gaaatgctat tgttttaccc ttaagatggt taacttacta taaactaaac    1500
acttatcctt ctttgttgga acttacagaa agagatttga ttgtgttatc aggactacgt    1560
ttctatcgtg agtttcggtt gcctaaaaaa gtggatcttg aaatgattat aaatgataaa    1620
gctatatcac ctcctaaaaa tttgatatgg actagtttcc ctagaaatta catgccatca    1680
cacatacaaa actatataga acatgaaaaa ttaaaatttt ccgagagtga taaatcaaga    1740
agagtattag agtattattt aagagataac aaattcaatg aatgtgattt atacaactgt    1800
gtagttaatc aaagttatct caacaaccct aatcatgtgg tatcattgac aggcaaagaa    1860
agagaactca gtgtaggtag aatgtttgca atgcaaccgg gaatgttcag acaggttcaa    1920
atattggcag agaaaatgat agctgaaaac attttacaat tctttcctga aagtcttaca    1980
agatatggtg atctagaact acaaaaaata ttagaattga aagcaggaat aagtaacaaa    2040
tcaaatcgct acaatgataa ttacaacaat tacattagta agtgctctat catcacagat    2100
ctcagcaaat tcaatcaagc atttcgatat gaaacgtcat gtatttgtag tgatgtgctg    2160
gatgaactgc atggtgtaca atctctatttt cctggttac atttaactat tcctcatgtc    2220
acaataatat gcacatatag gcatgcaccc ccctatatag gagatcatat tgtagatctt    2280
aacaatgtag atgaacaaag tggattatat agatatcaca tgggtggcat cgaagggtgg    2340
tgtcaaaaac tatggaccat agaagctata tcactattgg atctaatatc tctcaaaggg    2400
aaattctcaa ttactgcttt aattaatggt gacaatcaat caatagatat aagcaaacca    2460
atcagactca tggaaggtca aactcatgct caagcagatt atttgctagc attaaatagc    2520
cttaaattac tgtataaaga gtatgcaggc ataggccaca aattaaaagg aactgagact    2580
tatatatcac gagatatgca atttatgagt aaaacaattc aacataacgg tgtatattac    2640
ccagctagta taaagaaagt cctaagagtg ggaccgtgga taaacactat acttgatgat    2700
ttcaaagtga gtctagaatc tataggtagt ttgacacaag aattagaata tagaggtgaa    2760
agtctattat gcagtttaat atttagaaat gtatggttat ataatcagat tgctctacaa    2820
ttaaaaaatc atgcattatg taacaataaa ctatatttgg acatattaaa ggttctgaaa    2880
cacttaaaaa cctttttttaa tcttgataat attgatacag cattaacatt gtatatgaat    2940
ttacccatgt tatttggtgg tggtgatccc aacttgttat atcgaagttt ctatagaaga    3000
actcctgact tcctcacaga ggctatagtt cactctgtgt tcatacttag ttattataca    3060
aaccatgact aaaagataaa acttcaagat ctgtcagatg atagattgaa taagttctta    3120
acatgcataa tcacgtttga caaaaacccct aatgctgaat tcgtaacatt gatgagagat    3180
cctcaagctt tagggtctga gagacaagct aaaattacta gcgaaatcaa tagactggca    3240
gttacagagg ttttgagtac agctccaaac aaaaatattct ccaaaagtgc acaacattat    3300
actactacag agatagatct aaatgatatt atgcaaaata tagaacctac atatcctcat    3360
gggctaagag ttgtttatga agtttaccc ttttataaag cagagaaaat agtaaatctt    3420
atatcaggta caaaatctat aactaacata ctggaaaaaa cttctgccat agacttaaca    3480
gatattgata gagccactga gatgatgagg aaaaacataa ctttgcttat aaggatactt    3540
ccattggatt gtaacagaga taaagagag atattgagta tggaaaacct aagtattact    3600
gaattaagca aatatgttag ggaaagatct tggtctttat ccaatatagt tggtgttaca    3660
tcacccagta tcatgtatac aatggacatc aaatatacta caagcactat atctagtggc    3720
```

-continued

| | |
|---|---|
| ataattatag agaaatataa tgttaacagt ttaacacgtg gtgagagagg acccactaaa | 3780 |
| ccatgggttg gttcatctac acaagagaaa aaaacaatgc cagtttataa tagacaagtc | 3840 |
| ttaaccaaaa aacagagaga tcaaatagat ctattagcaa aattggattg ggtgtatgca | 3900 |
| tctatagata acaaggatga attcatggaa gaactcagca taggaaccct tgggttaaca | 3960 |
| tatgaaaagg ccaagaaatt atttccacaa tatttaagtg tcaattattt gcatcgcctt | 4020 |
| acagtcagta gtagaccatg tgaattccct gcatcaatac cagcttatag aacaacaaat | 4080 |
| tatcactttg acactagccc tattaatcgc atattaacag aaaagtatgg tgatgaagat | 4140 |
| attgacatag tattccaaaa ctgtataagc tttggcctta gtttaatgtc agtagtagaa | 4200 |
| caatttacta atgtatgtcc taacagaatt attctcatac ctaagcttaa tgagatacat | 4260 |
| ttgatgaaac ctcccatatt cacaggtgat gttgatattc acaagttaaa acaagtgata | 4320 |
| caaaaacagc atatgttttt accagacaaa ataagtttga ctcaatatgt ggaattattc | 4380 |
| ttaagtaata aaacactcaa atctggatct catgttaatt ctaatttaat attggcacat | 4440 |
| aaaatatctg actattttca taatacttac attttaagta ctaatttagc tggacattgg | 4500 |
| attctgatta tacaacttat gaaagattct aaaggtattt ttgaaaaaga ttggggagag | 4560 |
| ggatatataa ctgatcatat gtttattaat ttgaaagttt tcttcaatgc ttataagacc | 4620 |
| tatctcttgt gttttcataa aggttatggc aaagcaaagc tggagtgtga tatgaacact | 4680 |
| tcagatcttc tatgtgtatt ggaattaata gacagtagtt attggaagtc tatgtctaag | 4740 |
| gtattttttag aacaaaaagt tatcaaatac attcttagcc aagatgcaag tttacataga | 4800 |
| gtaaaaggat gtcatagctt caaattatgg tttcttaaac gtcttaatgt agcagaattc | 4860 |
| acagtttgcc cttgggttgt taacatagat tatcatccaa cacatatgaa agcaatatta | 4920 |
| acttatatag atcttgttag aatgggattg ataaatatag atagaataca cattaaaaat | 4980 |
| aaaacacaaat tcaatgatga atttttatact tctaatctct tctacattaa ttataacttc | 5040 |
| tcagataata ctcatctatt aactaaatat ataaggattg ctaattctga attagaaaat | 5100 |
| aattacaaca aattatatca tcctacacca gaaaccctag agaatatact agccaatccg | 5160 |
| attaaaagta atgacaaaaa gacactgaat gactattgta taggtaaaaa tgttgactca | 5220 |
| ataatgttac cattgttatc taataagaag cttattaaat cgtctgcaat gattagaacc | 5280 |
| aattacagca aacaagattt gtataattta ttccctatgg ttgtgattga tagaattata | 5340 |
| gatcattcag gcaatacagc caaatccaac caactttaca ctactactc ccaccaaata | 5400 |
| tctttagtgc acaatagcac atcactttac tgcatgcttc cttggcatca tattaataga | 5460 |
| ttcaattttg tatttagttc tacaggttgt aaaattagta tagagtatat tttaaaagat | 5520 |
| cttaaaatta aagatcccaa ttgtatagca ttcataggtg aaggagcagg gaatttatta | 5580 |
| ttgcgtacag tagtggaact tcatcctgac ataagatata tttacagaag tctgaaagat | 5640 |
| tgcaatgatc atagtttacc tattgagttt ttaaggctgt acaatggaca tatcaacatt | 5700 |
| gattatggtg aaaatttgac cattcctgct acagatgcaa ccaacaacat tcattggtct | 5760 |
| tatttacata taaagtttgc tgaacctatc agtctttttg tctgtgatgc cgaattgtct | 5820 |
| gtaacagtca actggagtaa aattataata gaatggagca agcatgtaag aaagtgcaag | 5880 |
| tactgttcct cagttaataa atgtatgtta atagtaaaat atcatgctca agatgatatt | 5940 |
| gatttcaaat tagacaatat aactatatta aaaacttatg tatgcttagg cagtaagtta | 6000 |
| aagggatcgg aggtttactt agtccttaca ataggtcctg cgaatatatt cccagtattt | 6060 |

-continued

```
aatgtagtac aaaatgctaa attgatacta tcaagaacca aaaatttcat catgcctaag      6120
aaagctgata aagagtctat tgatgcaaat attaaaagtt tgatacccct tctttgttac      6180
cctataacaa aaaaggaat taatactgca ttgtcaaaac taaagagtgt tgttagtgga       6240
gatatactat catattctat agctggacgt aatgaagttt tcagcaataa acttataaat      6300
cataagcata tgaacatctt aaaatggttc aatcatgttt taaatttcag atcaacagaa      6360
ctaaactata accatttata tatggtagaa tctacatatc cttacctaag tgaattgtta     6420
aacagcttga caaccaatga acttaaaaaa ctgattaaaa tcacaggtag tctgttatac      6480
aactttcata atgaataa                                                    6498
```

<210> SEQ ID NO 295
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295

```
tgatatggac tagtttccct agaaattaca tgccatc                               37
```

<210> SEQ ID NO 296
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 296

```
ggacuaguuu cccugaaaau uacat                                            25
```

<210> SEQ ID NO 297
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 297

```
auguaauuuc uagggaaacu aguccau                                          27
```

<210> SEQ ID NO 298
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298

```
ttgaaagcag gaataagtaa caaatcaaat cgctacaatg                            40
```

<210> SEQ ID NO 299
<211> LENGTH: 25
<212> TYPE: DNA
<213> ORGANISM: Artificial Sequence

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 299
gcaggaauaa guaacaaauc aaatc                                        25

<210> SEQ ID NO 300
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 300
gauuugauuu guuacuuauu ccugcuu                                      27

<210> SEQ ID NO 301
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
ttagaaccaa ttacagcaaa caagatttgt ataattt                           37

<210> SEQ ID NO 302
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 302
ccaauuacag caaacaagau uugta                                        25

<210> SEQ ID NO 303
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 303
uacaaaucuu guuugcugua auugguu                                      27

<210> SEQ ID NO 304
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
oligonucleotide

<400> SEQUENCE: 304
aagaccagtc gggatatcca g                                              21

<210> SEQ ID NO 305
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
aaagaggagt tcactgagat c                                              21

<210> SEQ ID NO 306
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
aactgaagac ccagatgaag g                                              21

<210> SEQ ID NO 307
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
aattgggcaa ggagacgtgg t                                              21

<210> SEQ ID NO 308
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
aaccgaggtc gaaacgtacg t                                              21

<210> SEQ ID NO 309
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
aaatggctgg atcgagtgag c                                              21

<210> SEQ ID NO 310
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 310
aacagcagaa tgctgtggat g                                          21

<210> SEQ ID NO 311
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
aagcaattga ggagtgcctg a                                          21

<210> SEQ ID NO 312
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
aactccttcc tcacacatgc a                                          21

<210> SEQ ID NO 313
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
ctggatatcc cgactggtct t                                          21

<210> SEQ ID NO 314
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
gatctcagtg aactcctctt t                                          21

<210> SEQ ID NO 315
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
ccttcatctg ggtcttcagt t                                          21

<210> SEQ ID NO 316
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 316
accacgtctc cttgcccaat t                                           21

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
acgtacgttt cgacctcggt t                                           21

<210> SEQ ID NO 318
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
gctcactcga tccagccatt t                                           21

<210> SEQ ID NO 319
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
catccacagc attctgctgt t                                           21

<210> SEQ ID NO 320
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
tcaggcactc ctcaattgct t                                           21

<210> SEQ ID NO 321
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
tgcatgtgtg aggaaggagt t                                           21

<210> SEQ ID NO 322
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
```
aagtcattca gtggatgtga tct                                              23

<210> SEQ ID NO 323
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
atgaggacta tggggattat tgg                                              23

<210> SEQ ID NO 324
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
cagccacacc taagcattta aaa                                              23

<210> SEQ ID NO 325
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
atgaatggaa cgacaatgaa atg                                              23

<210> SEQ ID NO 326
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
ggctgttcag ggataatcta aat                                              23

<210> SEQ ID NO 327
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
agatcacatc cactgaatga ctt                                              23

<210> SEQ ID NO 328
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328

```
ccaataatcc ccatagtcct cat                                              23

<210> SEQ ID NO 329
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329 tttttaaatgc ttaggtgtgg ctg                                             23

<210> SEQ ID NO 330
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
catttcattg tcgttccatt cat                                              23

<210> SEQ ID NO 331
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
atttagatta tccctgaaca gcc                                              23
```